US012606588B2

(12) United States Patent
Matray et al.

(10) Patent No.: US 12,606,588 B2
(45) Date of Patent: Apr. 21, 2026

(54) NUCLEOTIDE PROBES

(71) Applicant: Sony Group Corporation, Tokyo (JP)

(72) Inventors: Tracy Matray, Snohomish, WA (US); Erin Kwang, New York, NY (US); Melissa Dominguez, New York, NY (US)

(73) Assignee: SONY GROUP CORPORATION, Tokyo (JP)

( * ) Notice: Subject to any disclaimer, the term of this patent is extended or adjusted under 35 U.S.C. 154(b) by 1024 days.

(21) Appl. No.: 17/764,874

(22) PCT Filed: Sep. 30, 2020

(86) PCT No.: PCT/US2020/053609
§ 371 (c)(1),
(2) Date: Mar. 29, 2022

(87) PCT Pub. No.: WO2021/067483
PCT Pub. Date: Apr. 8, 2021

(65) Prior Publication Data

US 2022/0402963 A1 Dec. 22, 2022

Related U.S. Application Data

(60) Provisional application No. 62/908,509, filed on Sep. 30, 2019.

(51) Int. Cl.
*C07H 21/00* (2006.01)
*C12Q 1/6816* (2018.01)
*C12Q 1/6876* (2018.01)

(52) U.S. Cl.
CPC ........... *C07H 21/00* (2013.01); *C12Q 1/6816* (2013.01); *C12Q 1/6876* (2013.01)

(58) Field of Classification Search
CPC ..... C07H 21/00; C12Q 1/6816; C12Q 1/6876
USPC .......................................................... 536/22.1
See application file for complete search history.

(56) References Cited

U.S. PATENT DOCUMENTS

| | | | |
|---|---|---|---|
| 4,450,305 | A | 5/1984 | Kamhi |
| 4,476,229 | A | 10/1984 | Fino et al. |
| 4,778,753 | A | 10/1988 | Yamanishi et al. |
| 5,053,054 | A | 10/1991 | Kirchanski |
| 5,268,486 | A | 12/1993 | Waggoner et al. |
| 5,318,894 | A | 6/1994 | Pugia |
| 5,582,977 | A | 12/1996 | Yue et al. |
| 5,696,157 | A | 12/1997 | Wang et al. |
| 5,698,391 | A | 12/1997 | Cook et al. |
| 5,886,177 | A | 3/1999 | Cook et al. |
| 5,994,143 | A | 11/1999 | Bieniarz et al. |
| 6,005,093 | A | 12/1999 | Wood et al. |
| 6,140,480 | A | 10/2000 | Kool |
| 6,171,859 | B1 | 1/2001 | Herrnstadt et al. |
| 6,218,108 | B1 | 4/2001 | Kool |
| 6,365,730 | B1 | 4/2002 | Jennings et al. |
| 6,380,431 | B1 | 4/2002 | Whipple et al. |
| 6,479,650 | B1 | 11/2002 | Kool |
| 6,514,700 | B1 | 2/2003 | Singh |
| 6,534,041 | B1 | 3/2003 | Licha et al. |
| 6,627,400 | B1 | 9/2003 | Singh et al. |
| 6,670,193 | B2 | 12/2003 | Kool |
| 6,716,452 | B1 | 4/2004 | Piccariello et al. |
| 6,852,709 | B2 | 2/2005 | Leong et al. |
| 7,038,063 | B2 | 5/2006 | Lee et al. |
| 7,060,708 | B2 | 6/2006 | Piccariello et al. |
| 7,172,907 | B2 | 2/2007 | Chen et al. |
| 7,423,133 | B2 | 9/2008 | Kool et al. |
| 7,667,024 | B2 | 2/2010 | Mao et al. |
| 7,897,684 | B2 | 3/2011 | Bazan et al. |
| 8,008,522 | B2 | 8/2011 | Lukhtanov et al. |
| 8,101,776 | B2 | 1/2012 | Berens et al. |

(Continued)

FOREIGN PATENT DOCUMENTS

| | | | |
|---|---|---|---|
| CA | 2263671 | A1 | 2/1998 |
| CN | 101076537 | A | 11/2007 |

(Continued)

OTHER PUBLICATIONS

Meyer et al. Phthalimide-Oxy Derivatives for 3'- or 5'-Conjugation of Oligonucleotides by Oxime Ligation and Circularization of DNA by "Bis- or Tris-Click" Oxime Ligation. Eur. J. Org. Chem. 2017, 6931-6941. (Year: 2017).*
"What is an Analyte?," Google Search, dated Mar. 22, 2018, retrieved from https://www.google.com/search?q=what+is+an+analyte&rlz=ICIGCEB_enUS775US775&oq=what+is+an+analyte&aqs=chrome..69i57j0I5.3231j0j7&s . . . 2 pages.
Arian et al., "1,9-Dialkoxyanthracene as a 1O2-Sensitive Linker," *J. Am. Chem. Soc.* 133:3972-3980, 2011.
Avirah et al., "Infrared Absorbing Croconaine Dyes: Synthesis and Metal Ion Binding Properties," *J. Org. Chem.* 73(1):274-279, 2008.
Aviñó et al., "Solid-phase synthesis of oligomers carrying several chromophore units linked by phosphodiester backbones," *Bioorganic & Medicinal Chemistry Letters* 18:2306-2310, 2008.
Babitskaya et al., "Bromoacyl Analogues of Phosphatidycholine with Intramolecular Fluorescence Quenching and Their Use as Substrates for Continuous Monitoring of Phospholipase A2 Activity," *Applied Biochemistry and Microbiology* 40(4):351-356, 2004.
Bag et al., "Triazolyl-donor-acceptor chromophore-decorated unnatural amino acids and peptides: FRET events in a β-turn conformation," *Chem. Commun.* 50:433-435, 2014.

(Continued)

*Primary Examiner* — Yih-Horng Shiao

(74) *Attorney, Agent, or Firm* — Seed Intellectual Property Law Group LLP

(57) ABSTRACT

Compounds useful as nucleic acid probes are disclosed. In some embodiments, the compounds have the following structure (I) or a stereoisomer, tautomer or salt thereof, wherein M, $L^{1a}$, $L^2$, $L^8$, $L^{1b}$, $L^3$, $L^5$, $L^6$, $L^7$, $L^4$, $R^1$, $R^2$, $R^3$, $R^4$, $R^5$, $R_a$, $R_b$, $R_c$, $R_d$, m, n, q, and w are as defined herein. Methods associated with preparation and use of such compounds are also provided.

2 Claims, 12 Drawing Sheets

Specification includes a Sequence Listing.

(56) References Cited

U.S. PATENT DOCUMENTS

| | | | |
|---|---|---|---|
| 8,153,706 | B2 | 4/2012 | Vasudevan |
| 8,217,389 | B2 | 7/2012 | Nakano et al. |
| 8,293,700 | B2 | 10/2012 | Arranz |
| 8,349,308 | B2 | 1/2013 | Yurkovetskiy et al. |
| 8,354,515 | B2 | 1/2013 | Ueno et al. |
| 8,431,545 | B2 | 4/2013 | Kataoka et al. |
| 8,491,993 | B2 | 7/2013 | Nguyen et al. |
| 8,546,590 | B2 | 10/2013 | Gall |
| 8,632,947 | B2 | 1/2014 | Bentley et al. |
| 8,802,738 | B2 | 8/2014 | Emrick |
| 8,895,023 | B2 | 11/2014 | Rademacher et al. |
| 8,906,603 | B2 | 12/2014 | Castro et al. |
| 8,946,394 | B2 | 2/2015 | Na et al. |
| 9,029,537 | B2 | 5/2015 | Koch |
| 9,085,799 | B2 | 7/2015 | Bazan et al. |
| 9,150,782 | B2 | 10/2015 | Lee et al. |
| 9,400,273 | B1 | 7/2016 | Liu et al. |
| 9,545,447 | B2 | 1/2017 | Wooley et al. |
| 9,649,389 | B2 | 5/2017 | Groves et al. |
| 9,687,291 | B2 | 6/2017 | Shimizu et al. |
| 9,689,877 | B2 | 6/2017 | Matray et al. |
| 9,696,310 | B2 | 7/2017 | Margulies et al. |
| 9,714,946 | B2 | 7/2017 | Bradner et al. |
| 9,765,220 | B2 | 9/2017 | Matray et al. |
| 9,822,134 | B2 | 11/2017 | Segev |
| 9,851,359 | B2 | 12/2017 | Matray et al. |
| 9,884,070 | B2 | 2/2018 | Denardo et al. |
| 9,910,051 | B2 | 3/2018 | Beacham et al. |
| 9,913,992 | B2 | 3/2018 | Demarest et al. |
| 9,932,578 | B2 | 4/2018 | Feinstein et al. |
| 9,939,454 | B2 | 4/2018 | Dzubay et al. |
| 10,036,754 | B2 | 7/2018 | Matray et al. |
| 10,191,060 | B2 | 1/2019 | Chiu et al. |
| 10,435,563 | B2 | 10/2019 | Matray et al. |
| 10,617,670 | B2 | 4/2020 | Sapra et al. |
| 10,709,791 | B2 | 7/2020 | Stayton et al. |
| 10,834,091 | B2 | 11/2020 | Deninno et al. |
| 10,865,310 | B2 | 12/2020 | Matray et al. |
| 10,866,244 | B2 | 12/2020 | Matray et al. |
| 10,954,391 | B2 | 3/2021 | Matray et al. |
| 10,989,715 | B2 | 4/2021 | Matray et al. |
| 11,013,756 | B2 | 5/2021 | Haruta et al. |
| 11,084,932 | B2 | 8/2021 | Battrell et al. |
| 11,142,647 | B2 | 10/2021 | Matray et al. |
| 11,312,736 | B1 | 4/2022 | Matray et al. |
| 11,352,502 | B2 | 6/2022 | Matray et al. |
| 11,370,922 | B2 | 6/2022 | Matray et al. |
| 11,377,563 | B2 | 7/2022 | Matray et al. |
| 11,390,754 | B2 | 7/2022 | Singh et al. |
| 11,434,374 | B2 | 9/2022 | Matray et al. |
| 11,434,377 | B2 | 9/2022 | Matray et al. |
| 11,453,783 | B2 | 9/2022 | Matray et al. |
| 11,618,906 | B2 | 4/2023 | Steele et al. |
| 11,685,835 | B2 | 6/2023 | Matray |
| 11,827,661 | B2 | 11/2023 | Battrell et al. |
| 11,874,280 | B2 | 1/2024 | Jackson et al. |
| 11,931,419 | B2 | 3/2024 | Matray |
| 11,945,955 | B2 | 4/2024 | Matray et al. |
| 12,006,438 | B2 | 6/2024 | Singh et al. |
| 12,018,159 | B2 | 6/2024 | Matray et al. |
| 12,145,956 | B2 | 11/2024 | Matray et al. |
| 2001/0018503 | A1 | 8/2001 | Whipple et al. |
| 2002/0012947 | A1 | 1/2002 | Bevers et al. |
| 2002/0099013 | A1 | 7/2002 | Piccariello et al. |
| 2002/0142329 | A1 | 10/2002 | Matray et al. |
| 2003/0054361 | A1 | 3/2003 | Heller |
| 2003/0204075 | A9* | 10/2003 | Wang .................. C12Q 1/6883 536/24.3 |
| 2003/0207208 | A1 | 11/2003 | Uenishi |
| 2003/0207264 | A1 | 11/2003 | Packard et al. |
| 2004/0014981 | A1 | 1/2004 | Lugade et al. |
| 2004/0067498 | A1 | 4/2004 | Chenna et al. |
| 2004/0096825 | A1 | 5/2004 | Chenna et al. |
| 2004/0138467 | A1 | 7/2004 | French et al. |
| 2004/0224372 | A1 | 11/2004 | Li et al. |
| 2004/0241768 | A1 | 12/2004 | Whitten et al. |
| 2005/0054024 | A1 | 3/2005 | Lawrence |
| 2005/0123935 | A1 | 6/2005 | Haugland et al. |
| 2006/0008822 | A1 | 1/2006 | Manoharan et al. |
| 2006/0035302 | A1 | 2/2006 | Lee |
| 2006/0063186 | A1 | 3/2006 | Benson et al. |
| 2007/0042398 | A1 | 2/2007 | Peng et al. |
| 2007/0077549 | A1 | 4/2007 | Buller et al. |
| 2007/0148094 | A1 | 6/2007 | Uzgiris |
| 2007/0269902 | A1 | 11/2007 | Beechem et al. |
| 2008/0227939 | A1 | 9/2008 | Mizoshita et al. |
| 2009/0253792 | A1 | 10/2009 | Mickle et al. |
| 2009/0299070 | A1 | 12/2009 | Berens et al. |
| 2010/0021901 | A1 | 1/2010 | Yin et al. |
| 2010/0039684 | A1 | 2/2010 | Kolb et al. |
| 2010/0092386 | A1 | 4/2010 | Segev |
| 2010/0129800 | A1 | 5/2010 | Aymami Bofarull et al. |
| 2010/0192312 | A1 | 8/2010 | Cremer et al. |
| 2010/0248385 | A1 | 9/2010 | Tan |
| 2011/0014599 | A1 | 1/2011 | Akhavan-Tafti et al. |
| 2011/0224516 | A1 | 9/2011 | Romey et al. |
| 2012/0021454 | A1 | 1/2012 | Bikker et al. |
| 2012/0116079 | A1 | 5/2012 | Lukhtanov et al. |
| 2012/0126175 | A1 | 5/2012 | Ueno et al. |
| 2013/0059343 | A1 | 3/2013 | Cheung |
| 2013/0119363 | A1 | 5/2013 | Sasaki et al. |
| 2013/0137755 | A1 | 5/2013 | Segev |
| 2013/0202536 | A1 | 8/2013 | Mustaev et al. |
| 2013/0244891 | A1 | 9/2013 | Waggoner et al. |
| 2014/0023590 | A1 | 1/2014 | Gao et al. |
| 2014/0193504 | A1 | 7/2014 | Wooley et al. |
| 2014/0275508 | A1 | 9/2014 | Scarr et al. |
| 2015/0030541 | A1 | 1/2015 | Rogers |
| 2015/0110715 | A1 | 4/2015 | Eder et al. |
| 2015/0159198 | A1 | 6/2015 | McGall et al. |
| 2015/0232615 | A1 | 8/2015 | Kwiatkowski |
| 2015/0258217 | A1 | 9/2015 | Caravan |
| 2015/0362490 | A1* | 12/2015 | Margulies ............ C07D 417/14 506/18 |
| 2016/0039850 | A1 | 2/2016 | Segev |
| 2016/0176903 | A1 | 6/2016 | Segev |
| 2016/0264737 | A1 | 9/2016 | Bartholomew et al. |
| 2016/0327859 | A1 | 11/2016 | Idei et al. |
| 2016/0347907 | A1 | 12/2016 | Dose |
| 2017/0292957 | A1 | 10/2017 | Matray et al. |
| 2017/0326233 | A1 | 11/2017 | Demeule et al. |
| 2018/0065998 | A1 | 3/2018 | Battrell et al. |
| 2018/0092993 | A1 | 4/2018 | Desai et al. |
| 2018/0141935 | A1 | 5/2018 | Josel et al. |
| 2018/0312468 | A1 | 11/2018 | Zhang et al. |
| 2019/0136065 | A1 | 5/2019 | Singh et al. |
| 2019/0153232 | A1 | 5/2019 | Matray et al. |
| 2019/0177549 | A1 | 6/2019 | Matray et al. |
| 2019/0300716 | A1 | 10/2019 | Matray et al. |
| 2019/0378568 | A1 | 12/2019 | Robustelli |
| 2020/0032139 | A1 | 1/2020 | Behrendt et al. |
| 2020/0164085 | A1 | 5/2020 | Brandish et al. |
| 2020/0222554 | A1 | 7/2020 | Matray et al. |
| 2020/0330610 | A1 | 10/2020 | Desai et al. |
| 2020/0353089 | A1 | 11/2020 | Matray |
| 2020/0353094 | A1 | 11/2020 | Matray |
| 2020/0360526 | A1 | 11/2020 | Matray |
| 2021/0032277 | A1 | 2/2021 | Matray et al. |
| 2021/0032474 | A1 | 2/2021 | Matray et al. |
| 2021/0095130 | A1 | 4/2021 | Matray et al. |
| 2021/0096135 | A1 | 4/2021 | Matray et al. |
| 2021/0128591 | A1 | 5/2021 | Matray |
| 2021/0128739 | A1 | 5/2021 | Matray |
| 2021/0139440 | A1 | 5/2021 | Ramsden et al. |
| 2021/0253864 | A1 | 8/2021 | Matray et al. |
| 2021/0261782 | A1 | 8/2021 | Matray et al. |
| 2021/0285953 | A1 | 9/2021 | Matray et al. |
| 2021/0340380 | A1 | 11/2021 | Matray et al. |
| 2021/0395530 | A1 | 12/2021 | Matray et al. |
| 2022/0160887 | A1 | 5/2022 | Matray et al. |
| 2022/0168433 | A1 | 6/2022 | Matray et al. |
| 2022/0168435 | A1 | 6/2022 | Matray et al. |
| 2022/0175951 | A1 | 6/2022 | Boitano et al. |
| 2022/0220314 | A1 | 7/2022 | Singh et al. |

(56) References Cited

U.S. PATENT DOCUMENTS

| | | | |
|---|---|---|---|
| 2022/0227794 | A1 | 7/2022 | Matray et al. |
| 2022/0305127 | A1 | 9/2022 | Thomas et al. |
| 2022/0372297 | A1 | 11/2022 | Matray et al. |
| 2022/0380603 | A1 | 12/2022 | Matray et al. |
| 2023/0012304 | A1 | 1/2023 | Matray et al. |
| 2023/0129481 | A1 | 4/2023 | Matray et al. |
| 2024/0043455 | A1 | 2/2024 | Battrell et al. |
| 2024/0092820 | A1 | 3/2024 | Matray et al. |
| 2024/0132725 | A1 | 4/2024 | Sherif |
| 2024/0207423 | A1 | 6/2024 | Matray |
| 2024/0210408 | A1 | 6/2024 | Jackson et al. |
| 2024/0248094 | A1 | 7/2024 | Matray et al. |
| 2024/0255514 | A1 | 8/2024 | Matray et al. |
| 2024/0287313 | A1 | 8/2024 | Sherif |
| 2024/0287314 | A1 | 8/2024 | Matray et al. |
| 2024/0327440 | A1 | 10/2024 | Jackson et al. |

FOREIGN PATENT DOCUMENTS

| | | | |
|---|---|---|---|
| CN | 102174078 | A | 9/2011 |
| CN | 103319378 | A | 9/2013 |
| CN | 104072727 | A | 10/2014 |
| CN | 105377994 | A | 3/2016 |
| CN | 106589005 | A | 4/2017 |
| CN | 107106685 | A | 8/2017 |
| CN | 107454903 | A | 12/2017 |
| CN | 107580618 | A | 1/2018 |
| CN | 107709470 | A | 2/2018 |
| CN | 109153860 | A | 1/2019 |
| EP | 0708837 | B1 | 3/2006 |
| GB | 2 372 256 | A | 8/2002 |
| GB | 2 554 666 | A | 4/2018 |
| JP | S61207395 | A | 9/1986 |
| JP | H04282391 | A | 10/1992 |
| JP | 2000017183 | A | 1/2000 |
| JP | 2003532092 | A | 10/2003 |
| JP | 2011135823 | A | 7/2011 |
| JP | 2014527071 | A | 10/2014 |
| JP | 2016534107 | A | 11/2016 |
| JP | 2017504659 | A | 2/2017 |
| JP | 2017124994 | A | 7/2017 |
| JP | 2018507863 | A | 3/2018 |
| JP | 2018512167 | A | 5/2018 |
| JP | 2018515628 | A | 6/2018 |
| JP | 2019516807 | A | 6/2019 |
| JP | 2019516821 | A | 6/2019 |
| JP | 2021518410 | A | 8/2021 |
| JP | 2021527911 | A | 10/2021 |
| JP | 7069033 | B2 | 5/2022 |
| JP | 7239904 | B2 | 3/2023 |
| KR | 20030032939 | A | 4/2003 |
| KR | 20100138910 | A | 12/2010 |
| KR | 101041446 | B1 | 6/2011 |
| KR | 10-2015-0007795 | A | 1/2015 |
| KR | 20160022358 | A | 2/2016 |
| KR | 20180005650 | A | 1/2018 |
| KR | 10-2020-0133374 | A | 11/2020 |
| KR | 20210032434 | A | 3/2021 |
| KR | 102530707 | B1 | 5/2023 |
| SU | 1121931 | A1 | 4/1988 |
| WO | WO 9502700 | A1 | 1/1995 |
| WO | WO 9506731 | A2 | 3/1995 |
| WO | WO 9832463 | A2 | 7/1998 |
| WO | WO 0173123 | A2 | 10/2001 |
| WO | 0183502 | A1 | 11/2001 |
| WO | WO 0222883 | A1 | 3/2002 |
| WO | WO 02083954 | A1 | 10/2002 |
| WO | WO 2004007751 | A2 | 1/2004 |
| WO | WO 2007094135 | A1 | 8/2007 |
| WO | WO 2009113645 | A1 | 9/2009 |
| WO | WO 2010026957 | A1 | 3/2010 |
| WO | 2011088193 | A2 | 7/2011 |
| WO | WO 2013012687 | A2 | 1/2013 |
| WO | WO 2014102803 | A1 | 7/2014 |
| WO | WO 2014147642 | A1 | 9/2014 |
| WO | WO 2015091953 | A1 | 6/2015 |
| WO | WO 2015155753 | A2 | 10/2015 |
| WO | 2016168750 | A1 | 10/2016 |
| WO | WO 2016183185 | A1 | 11/2016 |
| WO | WO 2017003639 | A2 | 1/2017 |
| WO | WO 2017062271 | A2 | 4/2017 |
| WO | WO 2017089890 | A1 | 6/2017 |
| WO | WO 2017094897 | A1 | 6/2017 |
| WO | 2017173355 | A1 | 10/2017 |
| WO | 2017177065 | A2 | 10/2017 |
| WO | WO 2017197144 | A1 | 11/2017 |
| WO | WO 2018045278 | A1 | 3/2018 |
| WO | 2019071208 | A1 | 4/2019 |
| WO | WO 2019126691 | A1 | 6/2019 |
| WO | WO-2019140227 | A1 | 7/2019 |
| WO | WO 2019182765 | A1 | 9/2019 |
| WO | WO-2019182766 | A1 | 9/2019 |
| WO | 2020014634 | A1 | 1/2020 |
| WO | WO 2020219959 | A1 | 10/2020 |
| WO | 2021062176 | A2 | 4/2021 |
| WO | 2022125564 | A1 | 6/2022 |

OTHER PUBLICATIONS

Beaucage et al., "The Functionalization of Oligonucleotides Via Phosphoramidite Derivatives," *Tetrahedron* 49(10):1925-1963, 1993.

Becker et al., "New Thermotropic Dyes Based on Amino-Substituted Perylendicarboximides," *Chem. Eur. J.* 6(21):3984-3990, 2000.

Bergstrom et al., "A NaPi2b Antibody-Drug Conjugate Induces Durable Complete Tumor Regressions in Patient-Derived Xenograft Models of NSCLC," *IASLC 17th World Conference on Lung Cancer,* Vienna, Austria, Dec. 4-7, 2016 (8 pages).

Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015.

Bergstrom et al., "Potent Promise," *Innovations in Pharmaceutical Technology* 49:16-20, 2014.

Bergstrom et al., "XMT-1522 induces tumor regressions in pre-clinical models representing HER2-positive and HER2 low-expressing breast cancer," Mersana Therapeutics, Abstract P4-14-28, 2015, 1 page.

Boldyrev et al., "Synthesis and Characteristics of New Fluorescent Probes Based on Cardiolipin," *Russian Journal of Bioorganic Chemistry* 35(2):219-224, 2009.

Braeckmans et al., "Three-dimensional fluorescence recovery after photobleaching with the confocal scanning laser microscope," *Biophysical Journal* 85:2240-2252, 2003.

Braga et al., "Intracellular macromolecular mobility measured by fluorescence recovery after photobleaching with confocal laser scanning microscopes," *Molecular Biology of the Cell* 15:4749-4760, 2004.

Breul et al., "Fluorescent monomers as building blocks for dye labeled polymers: synthesis and application in energy conversion, biolabeling and sensors," Chem. Soc. Rev. 42(12):5366-5407, 2013.

Brinkley, "A brief survey of methods for preparing protein conjugates with dyes, haptens, and cross-linking reagents," *Bioconjugate Chem* 3:2-13, 1992.

Buckhout-White et al., "Assembling programmable FRET-based photonic networks using designer DNA scaffolds," *Nature Communications* 5:5615, Dec. 11, 2014. (16 pages).

CAPLUS Accession No. 1975: 171341, Holy, "Nucleic acid components and their analogs. CLXXII. Aliphatic analogs of nucleosides, nucleotides, and oligonucleotides," *Collection of Czechoslovak Chemical Communications* 40(1):187-214, 1975. (1 page).

CAS Registry No. 862288-26-4, American Chemical Society, 2021. (1 page).

Chang et al., "A General Approach for Generating Fluorescent Probes to Visualize Piconewton Forces at the Cell Surface," *J. Am. Chem. Soc.* 138:2901-2904, 2016. (4 pages).

Chattopadhyay et al., "Brilliant Violet Fluorophores: A New Class of Ultrabright Fluorescent Compounds for Immunofluorescence Experiments," *Cytometry Part A* 81A:456-466, 2012.

(56) References Cited

OTHER PUBLICATIONS

Chen et al., "Synthesis and properties of new segmented block poly(urethane-urea)s containing phosphatidylcholine analogues and polybutadienes," *Macro-Molecular Chemistry and Physics* 197(5):1587-1597, May 1996. (11 pages).
Chong et al., "Oxygen Quenching of Pyrene-Lipid Fluorescence in Phosphatidylcholine Vesicles—A Probe for Membrane Organization," *Biophys. J.* 47:613-621, 1985.
Ciccotelli et al., "Polyguanine-conjugated antigens for scavenger receptor targeting and self-adjuvanting vaccines (VAC13P.1125)," *The Journal of Immunology* 194(Suppl. 1):214.5, May 1, 2015 [Abstract]. (1 page).
Cuppoletti et al., "Oligomeric fluorescent labels for DNA," *Bioconjug. Chem.* 16(3):528- 534, 2005.
Dai et al., "DNA-polyfluorophore excimers as sensitive reporters for esterases and lipases," *Chem. Commun.* 46:1221-1223, 2010.
Damian et al., "Synthesis and DNA Interaction of Platinum Complex/Peptide Chimera as Potential Drug Candidates," *Eur. J. Org. Chem.* 6161-6170, 2010.
De Vos et al., "New Non Nucleosidic Phosphoramidites for the Solid Phase Multi-Labelling of Oligonucleotides: Comb- and Multifork-Like Structures," *Nucleosides & Nucleotides* 13(10):2245- 2265, 1994.
Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.
DiVittorio et al., "Synthetic peptides with selective affinity for apoptotic cells," *Org. Biomol. Chem.* 4:1966-1976, 2006.
Doi et al., "Hetero-Selective DNA-Like Duplex Stabilized by Donor-Acceptor Interactions," *Chem. Eur. J.* 21:15974-15980, 2015.
Drescher et al., "General Synthesis and Aggregation Behaviour of New Single-Chain Bolaphospholipids: Variations in Chain and Headgroup Structures," *Chemistry—A European Journal* 14(22):6796-6804, 2008.
Dropulic et al., "Update on New Antivirals Under Development for the Treatment of Double-Stranded DNA Virus Infections," Clinical Pharmacology & Therapeutics 88(5):610-619, Nov. 2010.
Dubrovsky, "Semiconductor nanoparticles as reporters in multiplexed immunoassay and cell analysis," *International Journal of Nanoscience* 8(1 & 2):163-167, 2009.
Finniss et al., "A versatile acid-labile linker for antibody-drug conjugates," Med. Chem, Commun; 5; Apr. 1, 2014, 4 pages.
Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem* 22:1309-1319, 2011.
Franzini et al., "Identification of Structure-Activity Relationships from Screening a Structurally Compact DNA-Encoded Chemical Library," *Angewandte Chemie International Edition* 54:3927-3931, Feb. 3, 2015 [with supporting information]. (41 pages).
Gao et al., "Libraries of Composite Polyfluors Built from Fluorescent Deoxyribosides," *Journal of the American Chemical Society* 124:11590-11591, 2002.
Gao et al., "Modified DNA Analogues That Sense Light Exposure with Color Changes," *Journal of the American Chemical Society* 126:12748-12749, 2004.
Gordon et al., "Analysis of simulated and experimental fluorescence recovery after photobleaching. Data for two diffusing components," *Biophysical Journal* 68:766-778, 1995.
Griesang et al., "Four-Color, Enzyme-Free Interrogation of DNA Sequences with Chemically Activated, 3'-Fluorphore-Labeled Nucleotides," *Angew. Chem. Int. Ed.* 45:6144-6148, 2006.
Gupta et al., "Dendrimers: Novel Polymeric Nanoarchitectures for Solubility Enhancement," *Biomacromolecules* 7(3):649-658, Mar. 2006 [Published online Feb. 15, 2006]. (10 pages).
Guryev et al., "Control of the Fluorescence of Dye-Antibody Conjugates by (2-Hydroxypropyl)-β-cyclodextrin in Fluorescence Microscopy and Flow Cytometry," *Analytical Chemistry* 83:7109-7114, Aug. 16, 2011.
Hanhela et al., "Synthesis and Evaluation of Fluorescent Materials for Colour Control of Peroxyoxalate Chemiluminescence. III. Yellow and Red Fluorescent Emitters," *Australian Journal of Chemistry* 34:1701-1717, 1981.
Haraguchi, "Live Cell Imaging: Approaches for Studying Protein Dynamics in Living Cells," *Cell Structure And Function* 27:333-334, 2002.
Hasegawa et al., "Cysteine, histidine and glycine exhibit anti-inflammatory effects in human coronary arterial endothelial cells," *Clinical and Experimental Immunology* 167:269-274, Jan. 11, 2012. (6 pages).
Irani et al., "Molecular properties of human IgG subclasses and their implications for designing therapeutic monoclonal antibodies against infectious diseases," *Molecular Immunology* 67:171-182, 2015.
Jain et al. "Current ADC Linker Chemistry," *Pharm. Res.* 32:3526-3540, 2015.
Johansson, "Choosing Reporter-Quencher Pairs for Efficient Quenching Through Formation of Intramolecular Dimers," *Methods in Molecular Biology* 335:17-29, 2006.
Kashida et al., "A Cationic Dye Triplet as a Unique "Glue" That Can Connect Fully Matched Termini of DNA Duplexes," *Chem. Eur. J.* 17:2614-2622, 2011.
Khandare et al., "Polymer-drug conjugates: Progress in polymeric prodrugs," *Progress in Polymer Science* 31(4):359-397, Apr. 2006. (39 pages).
Koo et al., "Fluorescent DNA chemosensors: identification of bacterial species by their volatile metabolites," *Chemical Communications* 47:11435-11437, 2011.
Kozma et al., "Fluorescent Ligands for Adenosine Receptors," *Bioorganic & Medicinal Chemistry Letters* 23: 26-36, 2013.
Krueger at al., "Fluorescent Amino Acids: Modular Building Blocks for the Assembly of New Tools for Chemical Biology," *ChemBioChem* 14:788-799, 2013.
Lapeyre et al., "Aryldithioethyloxycarbonyl (Ardec): A New Family of Amine Protecting Groups Removable under Mild Reducing Conditions and Their Applications to Peptide Synthesis," *Chem. Eur. J.* 12:3655-3671, 2006.
Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.
Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.
Lewis et al., "Orientation Control of Fluorescence Resonance Energy Transfer Using DNA as a Helical Scaffold," *J. Am. Chem. Soc.* 127(28):10002-10003, 2005.
Li et al., "Polymeric Drugs: Advances in the development of pharmacologically active polymers," *Journal of Controlled Release* 219:369-382, 2015.
Li et al., "Responsive nanogel-based dual fluorescent sensors for temperature and Hg2+ ions with enhanced detection sensitivity," *J. Mater. Chem.* 20:10716-10723, 2010.
Liu et al., "Detection of prostate-specific membrane antigen on HUVECs in response to breast tumor-conditioned medium," *International Journal of Oncology* 38:1349-1355, 2011.
Liu et al., "DNA-Based Micelles: Synthesis, Micellar Properties and Size-Dependent Cell Permeability," *Chem. Eur. J.* 16:3791-3797, 2010 (14 Pages).
Liu et al., "Increased Cytotoxicity and Decreased In Vivo Toxicity of FdUMP[10] Relative to 5-FU," *Nucleosides & Nucleotides* 18(8):1789-1802, Aug. 1999. (14 pages).
Liu et al., "Structure-based programming of lymph-node targeting in molecular vaccines," *Nature* 507:519-522, Mar. 27, 2014 [Published online Feb. 16, 2014]. (15 pages).
Luo et al., "Sensitive and rapid quantification of C-reactive protein using quantum dot-labeled microplate immunoassay," *Journal of Translational Medicine* 10(24):1-9, 2012.

(56) References Cited

OTHER PUBLICATIONS

Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem:* 1298-1307, 2004.
Masuko et al., "Fluorescence resonance energy transfer from pyrene to perylene labels for nucleic acid hybridization assays under homogenous solution conditions," *Nucleic Acids Research* 28(8):e34, 2000 (8 pages).
McKinlay et al., "Cell-Penetrating, Guanidinium-Rich Oligophosphoesters: Effective and Versatile Molecular Transporters for Drug and Probe Delivery," *J. Am. Chem. Soc.* 138:3510-3517, Feb. 22, 2016.
Mersana Therapeutics, URL= http://www.mersana.com, download date Jan. 3, 2019, 9 pages.
Midoux et al., "Chemical vectors for gene delivery: a current review on polymers, peptides and lipids containing histidine or imidazole as nucleic acids carriers," *British Journal of Pharmacology* 157:166-178, May 2009. (13 pages).
Molotkovsky et al., "Perylenoyl- and Anthrylvinyl-Labeled Lipids as Membrane Probes," *Biochimica et Biophysica Acta* 778:281-288, 1984.
Moss, "Nomenclature of Fused and Bridged Fused Ring Systems," *Pure & Appl. Chem.* 70(1):143-216, 1998.
Mthembu et al., "Breaking a Couple: Disulfide Reducing Agents," *ChemBioChem* 21, 2020. (10 pages).
Nolting, "Linker Technology for Antibody-Drug Conjugates," in Ducry (ed.), *Antibody-Drug Conjugates,* Humana Press, Totowa, NJ, 2013, Ch. 5, pp. 71-100.
Nussbaumer et al., "Amplification of Chirality by Supramolecular Polymerization of Pyrene Oligomers," *Angewandte Chemie International Edition* 50:5490-5494, 2011.
Oh et al., "Low-dose guanidine and pyridostigmine: relatively safe and effective long-term symptomatic therapy in Lambert-Eaton myasthenic syndrome," *Muscle & Nerve* 20:1146-1152, Sep. 1997. (7 pages).
Paris et al., "Probing DNA sequences in solution with a monomer-excimer fluorescence color change," *Nucleic Acids Research* 26(16):3789-3793, 1998.
Pelegrin et al., "Antiviral Monoclonal Antibodies: Can They Be More Than Simple Neutralizing Agents?" *Trends in Microbiology* 23(10):653-665, Oct. 2015.
Petersen et al., "Acyclic, achiral enamide nucleoside analogues. The importance of the C=C bond in the analogue for its ability to mimic natural nucleosides," *Organic & Biomolecular Chemistry* 1:3293-3296, Sep. 4, 2003. (4 pages).
Petreus et al., "Polyester imides containing main-chain phosphorus," *Revue Roumaine de Chimie* 34(8):971-978, 1994 (with English Abstract).
Phares et al., "Improving the Stability and Sensing of Electrochemical Biosensors by Employing Trithiol-Anchoring Groups in a Six-Carbon Self-Assembled Monolayer," *Anal. Chem.* 81(3):1095-1100, Feb. 1, 2009.
Poupart et al., "Aminopropargyl derivative of terpyridine-bis(methyl-enamine) tetraacetic acid chelate of europium (Eu (TMT)-AP3): a new reagent for fluorescent labelling of proteins and peptides," Org. Biomol. Chem. 4:4165-4177, Oct. 2006.
Pownall et al., "Kinetics of Spontaneous and Plasma-Stimulated Sphingomyelin Transfer," *Biochimica et Biophysica Acta* 712:169-176, 1982.
PubChem, "US20100012929A1-20100121-C00010_4," SID No. 140452858, retrieved Mar. 29, 2016 from URL https://pubchem.ncbi.nlm.nih.gov/substance/140452858#sectio . . . , 6 pages.
Ren et al., "An Antisense Oligodeoxynucleotide-Doxorubicin Conjugate: Preparation and Its Reversal Multidrug Resistance of Human Carcinoma Cell Line In Vitro," Nucleosides, Nucleotides & Nucleic Acids 23(10):1595-1607, 2004.
RN 230952-79-1, Registry Database Compound, 1999.
Rochat et al., "Water-Soluble Cationic Conjugated Polymers: Response to Electron-Rich Bioanalytes," *J. Am. Chem. Soc.* 135:17703-17706, 2013.
Rupcich et al., "Quenching of Fluorophore-Labeled DNA Oligonucleotides by Divalent Metal Ions: Implications for Selection, Design, and Applications of Signaling Aptamers and Signaling Deoxyribozymes," J. Am. Chem. Soc. 126(3):780-790, 2006.
Saito et al., "Dual-labeled oligonucleotide probe for sensing adenosine via FRET: A novel alternative to SNPs genotyping," Chem. Commun.:2133-2135, 2007.
Samal et al., "Cationic polymers and their therapeutic potential," *Chemical Society Reviews* 41:7147-7194, Aug. 2012. (48 pages).
Shuey et al., "Cyclohexanediol Bisphosphates as Models for Phospholipid-Metal Ion Binding Sites," *Bioorganic Chemistry* 21:95-108, Mar. 1993. (14 pages).
Shuman et al., "Bacterial DNA repair by non-homologous end joining," *Nature Reviews Microbiology* 5:852-861, Nov. 2007.
Singh et al., "Multiplexed measurement of membrane protein populations," *Caplus* 2003:769075, 2003. (2 pages).
Stewart et al., "The Fluorescence of a Chelating Two-Photon-Absorbing Dye is Enhanced with the Addition of Transition Metal Ions but Quenched in the Presence of Acid," *Proc. of SPIE* 9939:993904, 2016 (10 pages).
STIC Search Report from American Chemical Society, for U.S. Appl. No. 17/255,353, dated Sep. 7, 2023. (143 pages).
Striebel et al., "Enhancing sensitivity of human herpes virus diagnosis with DNA microarrays using dendrimers," *Experimental and Molecular Pathology* 77:89-97, Oct. 2004 [Published online Jul. 15, 2004]. (9 pages).
Stuart et al., "Site-Specific DNA-Doxorubicin Conjugates Display Enhanced Cytotoxicity to Breast Cancer Cells," *Bioconjugate Chemistry* 25:406-413, 2014.
Sun et al., "Dual-Color Fluorescence Imaging of Magnetic Nanoparticles in Live Cancer Cells Using Conjugated Polymer Probes," *Scientific Reports* 6:22368, 2016. (12 pages).
Sun et al., "High yield production of high molecular weight poly-(ethylene glycol)/ α-cyclodextrin polyrotaxanes by aqueous one-pot approach," *Polymer* 53:2884-2889, 2012.
Sun et al., "Self-assembled biodegradable micellar nanoparticles of amphiphilic and cationic block copolymer for siRNA delivery," *Biomaterials* 29:4348-4355, available online Aug. 2008. (8 pages).
Sun et al., "Ultrabright and Multicolorful Fluorescence of Amphiphilic Polyethyleneimine Polymer Dots for Efficiently Combined Imaging and Therapy," *Scientific Reports* 3:3036, 2013. (6 pages).
Tabujew et al., "Chapter One: Functionalization of Cationic Polymers for Drug Delivery Applications," *RSC Polymer Chemistry Series* 13, 2015. (29 pages).
Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, 2002.
Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).
Teyssot et al., "Aromatic Nitrogen Donors for Efficient Copper(1)-NHC CuAAC under Reductant-Free Conditions," *Eur. J. Org. Chem.* 3507-3515, 2010.
Tram et al., "Oligonucleotide Labeling Using BODIPY Phosphoramidite," *Nucleosides, Nucleotides & Nucleic Acids* 30(1):1-11, 2011.
Vinogradov et al., "Total synthesis and biochemical characterization of mirror image barnase," *Chem Sci.* 6: 2997-3002, 2015.
Vybornyi et al., "Formation of Two-Dimensional Supramolecular Polymers by Amphiphilic Pyrene Oligomers," *Angew. Chem. Int. Ed.* 52:114488-11493, 2013.
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Wang et al., "DNA Polyfluorophores for Real-Time Multicolor Tracking of Dynamic Biological Systems," *Angew. Chem. Int. Ed.* 51:7176-7180, 2012.

(56) References Cited

OTHER PUBLICATIONS

Wang et al., "Fluorescence-Based Evaluation of the Partitioning of Lipids and Lipidated Peptides into Liquid-Ordered Lipid Microdomains: A Model for Molecular Partitioning into Lipid Rafts," *Biophysical Journal* 79:919-933, Aug. 2000.
Wilson et al., "Efficient Quenching of Oligomeric Fluorophores on a DNA Backbone," *Journal of the American Chemical Society* 129(50):15426-15427, 2007.
Wilson et al., "Oligodeoxyfluorosides: Strong Sequence of Dependence of Fluorescence Emission," *Tetrahedron* 63(17):3427-3433, 2007 (18 Pages).
Winiger et al., "Long-Distance Electronic Energy Transfer in Light-Harvesting Supramolecular Polymers," *Angew. Chem. Int. Ed.* 53:13609-13613, 2014.
Wu Yi et al., "$^{Py}$ A-Modified Oligodeoxyadenylates: Expanded Fluorescence Phenomena and Structural Formation," *Chemistry—An Asian Journal* 7:60-63, Nov. 2011. (4 pages).
Yu et al., "Targeted Delivery of an Anti-Inflammatory PDE4 Inhibitor to Immune Cells via an Antibody-drug Conjugate," *Molecular Therapy* 24(12):2078-2089, Dec. 2016.
Yurkovetskiy et al., "Advantages of Polyacetal Polymer-based Antibody Drug Conjugates: Application to Low Expression Targets," Mersana Therapeutics, technical paper #2645, 2014, 1 page.
Zhang et al., "FRET Imaging of Enzyme-Responsive HPMA Copolymer Conjugate," *Macromol. Biosci.* 17:1600125, 2017 (8 pages).
Zhao et al., "Mussel-Inspired One-Pot Synthesis of a Fluorescent and Water-SolublePolydopamine-Polyethyleneimine Copolymer," Macromol. Rapid Commun. 36:909-915, 2015.
Dmitry M. Kolpashchikov: "Binary Probes for Nucleic Acid Analysis", Chemical Reviews, vol. 110, No. 8, Aug. 11, 2010 (Aug. 11, 2010), pp. 4709-4723,XP055459155.
Marras S A E et al: "Efficiencies of fluorescence resonance energy transfer and contact-mediated quenching in oligonucleotide probes", Nucleic Acids Research, Oxford University Press, GB, vol. 30, No. 21, Nov. 1, 2002 (Nov. 1, 2002), pp. e122-1, XP002298327.
Antos et al., "Site-Specific Protein Labeling via Sortase-Mediated Transpeptidation," Current Protocols in Protein Science, Chapter 15:15.3.1-15.3.9, Apr. 2009 (HHS Public Access Author Manuscript, available in PMC Aug. 10, 2017). (23 pages).
Doronina et al., "Development of potent monoclonal antibody auristatin conjugates for cancer therapy," Nature Biotechnology 21(7):778-784, Jul. 2003 [Published online Jun. 1, 2003] (with Erratum as published Nature Biotechnology 21(8):941, Aug. 2003). (8 pages).
Lee et al., "Targeted multimodal imaging modalities," Advanced Drug Delivery Reviews 76:60-78, Jul. 24, 2014. (19 pages).
Neidle et al. (Eds.), "Chapter 7: Acridine-based Anticancer Drugs," Molecular Aspects of Anticancer Drug-DNA Interactions, Topics in Molecule in Structural Biology, vol. 2, pp. 270-311, 1994. (52 pages).
Sousa et al., "Phenazines: Natural products for microbial growth control," hLife 2(3):100-112, Mar. 2024. (13 pages).
Wagenknecht, "Fluorescent DNA Base Modifications and Substitutes: Multiple Fluorophore Labeling and the DETEQ Concept," Annals of the New York Academy of Sciences 1130(1):122-130, May 2008. (9 pages).
Bargh et al., "Cleavable linkers in antibody-drug conjugates," *Chemical Society Reviews* 48(16):4361-4374, Aug. 21, 2019. (15 pages).
CAPLUS Accession No. 1991:467753, Mielewczyk et al., "5' end fluorescent labelling of oligonucleotides with riboflavin-derived phosphitylating reagent," *Acta Biochimica Polonica* 36(3-4):225-233, 1989. (1 page).
CAPLUS Accession No. 1995:665426, Chen et al., "Synthesis of Novel Phosphoramidite Reagents for the Attachment of Antisense Oligonucleotides to Various Regions of the Benzophenanthridine Ring System," *Bioconjugate Chemistry* 6(4):473-482, Jul. 1, 1995. (1 page).
CAPLUS Accession No. 1995:733249, WO9506731A2, filed Mar. 9, 1995. (1 page).
CAPLUS Accession No. 1995:849926, Reed et al., "Structure-Activity Relationships of Cytotoxic Cholesterol-Modified DNA Duplexes," *Journal of Medicinal Chemistry* 38(22):4587-4596, Oct. 27, 1995. (1 page).
CAPLUS Accession No. 1997:497709, Puri et al., "Synthesis of 5'-polyarene-tethered oligo-DNAs and the thermal stability and spectroscopic properties of their duplexes and triplexes," *Tetrahedron* 53(30):10409-10432, Jul. 28, 1997. (1 page).
Chen et al., "Synthesis of Novel Phosphoramidite Reagents for the Attachment of Antisense Oligonucleotides to Various Regions of the Benzophenanthridine Ring System," *Bioconjugate Chemistry* 6(4):473-482, Jul. 1, 1995. (10 pages).
Kozytska et al., "Discovery of the novel, homogenous payload platform Dolasynthen for Antibody-Drug Conjugates," Mersana Therapeutics, Abstract #272, 2018. (1 page).
Lee et al., "The spectroscopic analysis for binding of amphipathic and antimicrobial model peptides containing pyrenylalanine and tryptophan to lipid bilayer," *Biochimica et Biophysica Acta* 984:174-182, Sep. 4, 1989. (9 pages).
Liso et al., "Polymeric drugs derived from Ibuprofen with improved antiinflammatory profile," *Journal of Biomedical Materials Research* 32:553-560, Dec. 1996. (8 pages).
Liu et al., "Imidazole inhibits autophagy flux by blocking autophagic degradation and triggers apoptosis via increasing FoxO3a-Bim expression," *International Journal of Oncology* 46:721-731, Feb. 2015. (11 pages).
Lvnitski et al., "Introducing charge transfer functionality into prebiotically relevant β-sheet peptide fibrils," *Chemical Communications* 50:6733-6736, May 12, 2014. (4 pages).
Mielewczyk et al., "5' end fluorescent labelling of oligonucleotides with riboflavin-derived phosphitylating reagent," *Acta Biochimica Polonica* 36(3-4):225-233, 1989. (9 pages).
Pawelczyk et al., "Molecular Consortia-Various Structural and Synthetic Concepts for More Effective Therapeutics Synthesis," *International Journal of Molecular Sciences* 19:1104, Apr. 6, 2018. (19 pages).
Puri et al., "Synthesis of 5'-polyarene-tethered oligo-DNAs and the thermal stability and spectroscopic properties of their duplexes and triplexes," *Tetrahedron* 53(30):10409-10432, Jul. 28, 1997. (24 pages).
Reed et al., "Structure-Activity Relationships of Cytotoxic Cholesterol-Modified DNA Duplexes," *Journal of Medicinal Chemistry* 38(22):4587-4596, Oct. 27, 1995. (10 pages).
Wang et al., "Novel dexamethasone-HPMA copolymer conjugate and its potential application in treatment of rheumatoid arthritis," *Arthritis Research & Therapy* 9(1):R2, Jan. 18, 2007. (9 pages).
Wang, "Modern Synthetic Methods and Technologies of Polymers," Common Knowledge Evidence, Tongji University Press, 1st Edition, Jul. 2013, pp. 210-211. (includes portion of Chinese Office Action with English Summary of relevance) (20 pages).
Xu et al., "Synthesis of [D-Pyrenylalanine4,4']gramicidin S by Solid-Phase-Synthesis and Cyclization-Cleavage Method with Oxime Resin," *Chemistry Letters* 21:191-194, Feb. 1992. (4 pages).
Hans-Achim Wagenknecht: "Fluorescent DNA Base Modifications and Substitutes: Multiple Fluorophore Labeling and the DETEQ Concept", Annals of the New York Academy of Sciences, New York Academy of Sciences, Jun. 28, 2008 (Jun. 28, 2008), pp. 122-130, US,vol. 1130, No. 1, New York, USA, XP071405433.
Katherine Johansson, "Fluorescent Energy Transfer Nucleic Acid Probes", 2006, vol. 335 , p. 17-29 , DOI:10.1385/1-59745-069-3:17.

* cited by examiner

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence

<400> SEQUENCE: 1

ccgtattata tgtttaaaaa                                                 20


<210> SEQ ID NO 2
<211> LENGTH: 20
<212> TYPE: DNA
<213> ORGANISM: Artificial Sequence
<220> FEATURE:
<223> OTHER INFORMATION: Synthetic sequence

<400> SEQUENCE: 2

tttttaaaca tataatacgg                                                 20


<210> SEQ ID NO 3
<211> LENGTH: 12
<212> TYPE: DNA
<213> ORGANISM: Artificial Sequence
<220> FEATURE:
<223> OTHER INFORMATION: Synthetic sequence

<400> SEQUENCE: 3

cgacgcttac ag                                                         12


<210> SEQ ID NO 4
<211> LENGTH: 12
<212> TYPE: DNA
<213> ORGANISM: Artificial Sequence
<220> FEATURE:
<223> OTHER INFORMATION: Synthetic sequence

<400> SEQUENCE: 4

ccgactgtgc at                                                         12


<210> SEQ ID NO 5
<211> LENGTH: 15
<212> TYPE: DNA
<213> ORGANISM: Artificial Sequence
<220> FEATURE:
<223> OTHER INFORMATION: Synthetic sequence

<400> SEQUENCE: 5

atgcttctag gactc                                                      15


<210> SEQ ID NO 6
<211> LENGTH: 12
<212> TYPE: DNA
<213> ORGANISM: Artificial Sequence
```

-continued

<220> FEATURE:
<223> OTHER INFORMATION: Synthetic sequence

<400> SEQUENCE: 6
atgcacagtc gg 12

<210> SEQ ID NO 7
<211> LENGTH: 12
<212> TYPE: DNA
<213> ORGANISM: Artificial Sequence
<220> FEATURE:
<223> OTHER INFORMATION: Synthetic sequence

<400> SEQUENCE: 7
ctgtaagcgt cg 12

<210> SEQ ID NO 8
<211> LENGTH: 11
<212> TYPE: DNA
<213> ORGANISM: Artificial Sequence
<220> FEATURE:
<223> OTHER INFORMATION: Synthetic sequence

<400> SEQUENCE: 8
gtaacgagcc t 11

<210> SEQ ID NO 9
<211> LENGTH: 11
<212> TYPE: DNA
<213> ORGANISM: Artificial Sequence
<220> FEATURE:
<223> OTHER INFORMATION: Synthetic sequence

<400> SEQUENCE: 9
cattgctcgg a 11

<210> SEQ ID NO 10
<211> LENGTH: 11
<212> TYPE: DNA
<213> ORGANISM: Artificial Sequence
<220> FEATURE:
<223> OTHER INFORMATION: Synthetic sequence

<400> SEQUENCE: 10
tatggcccgg a 11

NUCLEOTIDE PROBES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 870268_429USPC_SEQUENCE_LISTING.txt. The text file is 2.1 KB, was created on Mar. 23, 2022, and is being submitted electronically via EFS-Web.

BACKGROUND

Technical Field

The present disclosure is generally directed to compounds comprising polymeric chromophores covalently bound to at least one polynucleotide (e.g., compounds comprising polymer fluorescent moieties bound to a nucleotide probe), as well as compositions and kits comprising the same, and methods for their preparation and use in various analytical methods.

Description of the Related Art

Nucleic acid hybridization probes are used to detect specific target sequences in various diagnostic and analytical contexts. Conventional, heterogeneous, hybridization assays typically comprise the following steps: immobilization of a target nucleic acid (e.g., on paper, beads, or plastic surfaces); addition of labelled probes that are complementary to the sequence of the target; hybridization; removal of unhybridized probes; and detection of the probes remaining bound to the immobilized target.

Unhybridized probes are removed by extensive washing of the hybridized target nucleic acids. This is generally the most time-consuming part of the procedure, and often utilizes complex formats such as sandwich hybridization. Additionally, using solid surfaces to immobilize the target nucleic acids lengthens the time it takes for hybridization by restricting the mobility of, or access to, the target by the probes. Additionally, solid surfaces may interfere with signal from the probes or lead to noise in the signal. The requirement that the probe-target hybrids be isolated also precludes in vivo detection and concurrent detection of nucleic acids during synthesis reactions (real-time detection).

There is therefore a need in the art for improved probes with increased brightness and produce a lower signal-to-noise ratio. The present disclosure fulfills this need and provides further related advantages.

BRIEF SUMMARY

Embodiments of the present application include a compound having the following structure (I):

(I)

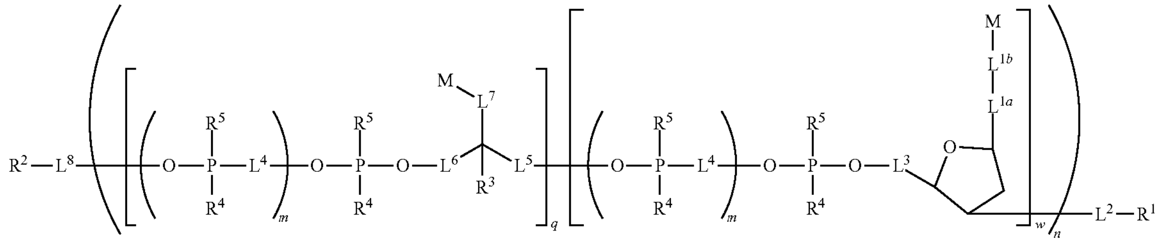

or a stereoisomer, salt or tautomer thereof, wherein:

M is, at each occurrence, independently either: a) the same or different fluorophore; or b) the same or different fluorophore quencher;

$L^{1a}$ is, at each occurrence, independently a heteroarylene linker;

$L^2$ and $L^8$ are independently optional linkers;

$L^{1b}$, $L^3$, $L^5$, $L^6$ and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$R^1$ and $R^2$ each independently comprise a polynucleotide or are each independently H, OH, SH, alkyl, alkoxy, alkylether, heteroalkyl or $-OP(=R_a)(R_b)R_c$, provided at least one of $R^1$ and $R^2$ comprises a polynucleotide;

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxy alkylether, phosphate, thiophosphate, phosphoalkyl, thiophosphoalkyl, phosphoalkylether or thiophosphoalkylether;

$R_d$ is a counter ion;

L' is, at each occurrence, independently a linker comprising a covalent bond to a solid support, a linker comprising a covalent bond to a solid support residue or a linker comprising a covalent bond to a nucleoside;

m is, at each occurrence, independently an integer of zero or greater;

n is an integer of one or greater; and q and w are, at each occurrence, independently 0 or 1, provided at least one occurrence of either q or w is 1.

In additional aspects, the present application describes a composition comprising a compound of structure (Ia) and a compound of structure (Ib):

(Ia)

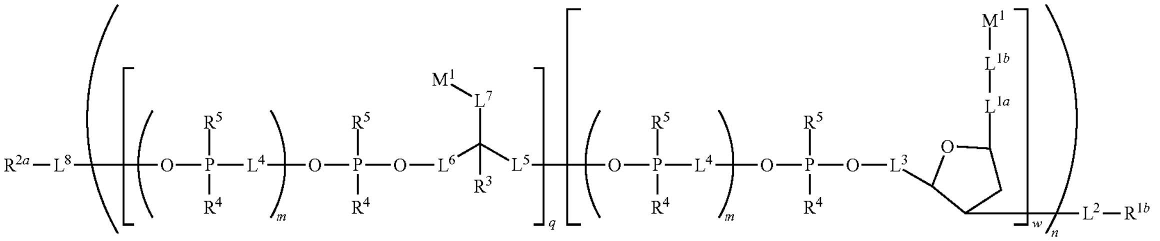

(Ib)

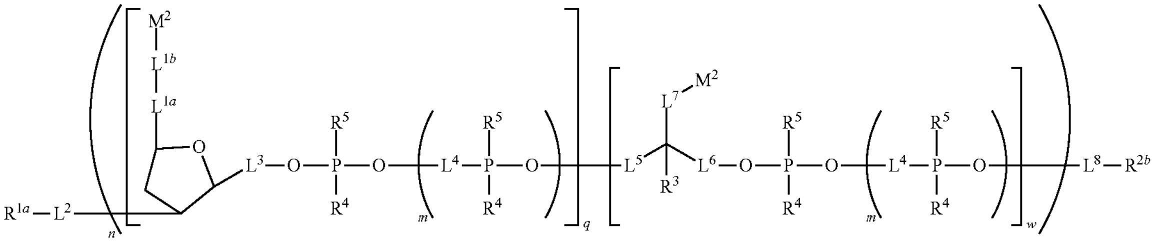

or a stereoisomer, salt or tautomer thereof, wherein:

$M^1$ is, at each occurrence, independently the same or different fluorophore;

$M^2$ is, at each occurrence, independently the same or different fluorophore quencher;

$L^{1a}$ is, at each occurrence, independently a heteroarylene linker;

$L^2$ and $L^8$ are independently optional linkers:

$L^{1b}$, $L^3$, $L^5$, $L^6$ and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$R^{1a}$ and $R^{2b}$ each independently comprise a polynucleotide or are each independently H, OH, SH, alkyl, alkoxy, alkylether, heteroalkyl or —OP(=$R_a$)($R_b$)$R_c$, provided at least one of $R^{1a}$ and $R^{2b}$ comprise a polynucleotide;

$R^{1b}$ and $R^{2a}$ each independently comprise a polynucleotide or are each independently H, OH, SH, alkyl, alkoxy, alkylether, heteroalkyl or —OP(=$R_a$)($R_b$)$R_c$, provided at least one of $R^{1a}$ and $R^{2b}$ comprise a polynucleotide;

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

L' is, at each occurrence, independently a linker comprising a covalent bond to a solid support, a linker comprising a covalent bond to a solid support residue or a linker comprising a covalent bond to a nucleoside;

m is, at each occurrence, independently an integer of zero or greater;

n is an integer of one or greater; and q and w are, at each occurrence, independently 0 or 1, provided at least one occurrence of either q or w is 1.

Additional aspects of the present application include a compound having the following structure (II):

(II)

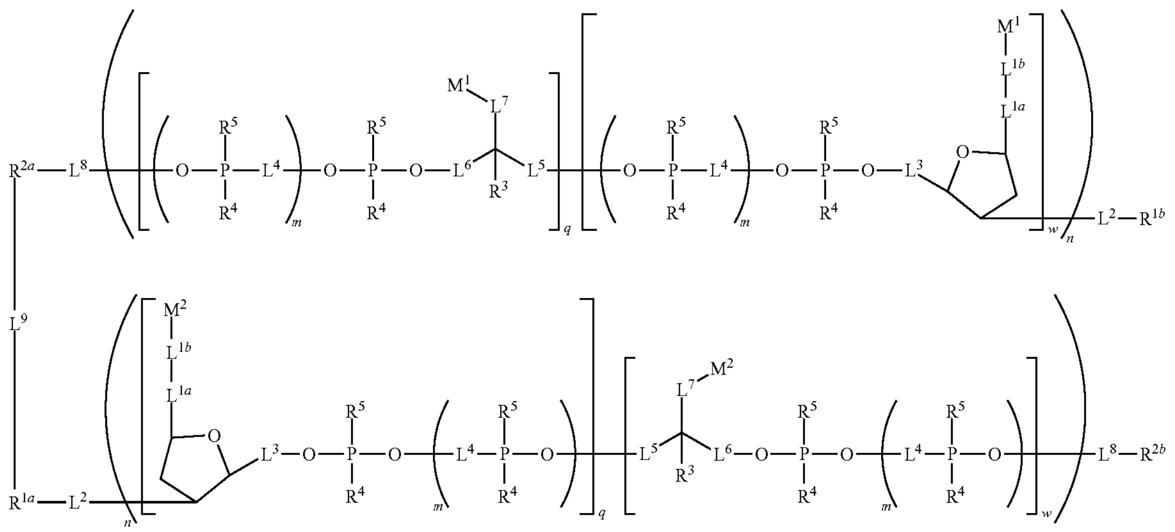

or a stereoisomer, salt or tautomer thereof, wherein:

$M^1$ is, at each occurrence, independently the same or different fluorophore;

$M^2$ is, at each occurrence, independently the same or different fluorophore quencher;

$L^{1a}$ is, at each occurrence, independently a heteroarylene linker;

$L^2$ and $L^8$ are independently optional linkers:

$L^{1b}$, $L^3$, $L^5$, $L^6$ and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$L^9$ is a linker comprising a polynucleotide;

$R^{1a}$ and $R^{2a}$ each independently comprise a polynucleotide;

$R^{1b}$ and $R^{2b}$ each independently comprise a polynucleotide or are each independently H, OH, SH, alkyl, alkoxy, alkylether, heteroalkyl or —OP(=$R_a$)($R_b$)$R_c$;

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

L' is, at each occurrence, independently a linker comprising a covalent bond to a solid support, a linker comprising a covalent bond to a solid support residue or a linker comprising a covalent bond to a nucleoside;

m is, at each occurrence, independently an integer of zero or greater;

n is an integer of one or greater; and q and w are, at each occurrence, independently 0 or 1, provided at least one occurrence of either q or w is 1.

Still further embodiments of the present disclosure comprise a compound having the following structure (III):

(III)

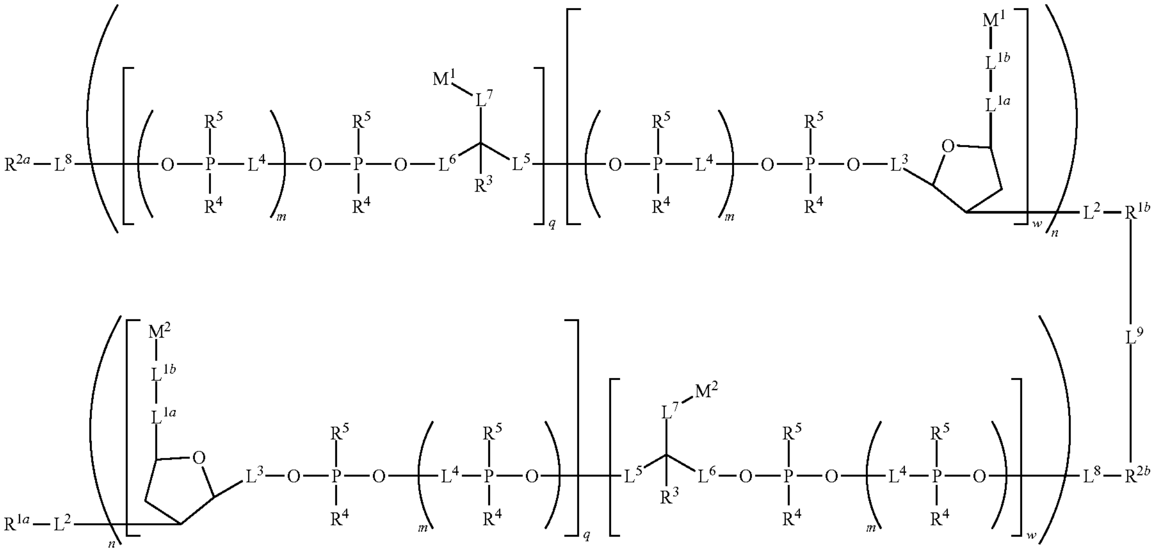

or a stereoisomer, salt or tautomer thereof, wherein:

$M^1$ is, at each occurrence, independently the same or different fluorophore;

$M^2$ is, at each occurrence, independently the same or different fluorophore quencher;

$L^{1a}$ is, at each occurrence, independently a heteroarylene linker;

$L^2$ and $L^8$ are independently optional linkers:

$L^{1b}$, $L^3$, $L^5$, $L^6$ and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$L^9$ is a linker comprising a polynucleotide;

$R^{1a}$ and $R^{2a}$ each independently comprise a polynucleotide or are each independently H, OH, SH, alkyl, alkoxy, alkylether, heteroalkyl or —OP(=$R_a$)($R_b$)$R_c$;

$R^{1b}$ and $R^{2b}$ each independently comprise a polynucleotide;

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

L' is, at each occurrence, independently a linker comprising a covalent bond to a solid support, a linker comprising a covalent bond to a solid support residue or a linker comprising a covalent bond to a nucleoside;

m is, at each occurrence, independently an integer of zero or greater;

n is an integer of one or greater; and q and w are, at each occurrence, independently 0 or 1, provided at least one occurrence of either q or w is 1.

In still further aspects, the present disclosure comprises detectable probe for identifying the presence of a target nucleotide sequence, comprising:

a first polynucleotide having a first end, the first polynucleotide having a first sequence that comprises a target complement sequence that has at least 90% complementarity to a target nucleotide sequence;

a first polymer having a first end and a second end, the first end being covalently bound to the first end of the first polynucleotide, the first polymer comprising two fluorophores; and a second polynucleotide having a first end that is covalently bound to the second end of the first polymer.

In additional aspects, the present disclosure further comprises detectable probe for identifying the presence of a target nucleotide sequence, comprising:

a) a first polynucleotide covalently bound to a first polymer comprising two or more fluorophores;

b) a second segment comprising a second nucleotide sequence covalently bound to a second polymer comprising two or more fluorophore quenchers;

wherein the first nucleotide sequence comprises: i) a target complement sequence having at least 90% complementarity to the target nucleic acid sequence, the target complement sequence capable of forming, with the target sequence, a double-stranded hybrid having a first strength under assay conditions; ii) and a probe complement sequence having at least 90% complementarity to at least a portion of the second nucleotide sequence, the probe complement sequence capable of forming, with at least the portion of the second nucleotide sequence, a double-stranded hybrid having a second strength under the assay conditions, the second strength being less than the first strength, and wherein the first polymer, in the absence of the second polymer, has a peak fluorescence emission upon excitation with a predetermined wavelength of ultraviolet light of at least 85% of the sum of the peak fluorescence emission of each individual fluorophore present in the first polymer upon excitation with the same wavelength of ultraviolet light.

In yet further aspects, the present application comprises a kit comprising a compound, composition, or detectable probe described herein.

BRIEF DESCRIPTION OF THE SEVERAL VIEWS OF THE DRAWINGS

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1A:
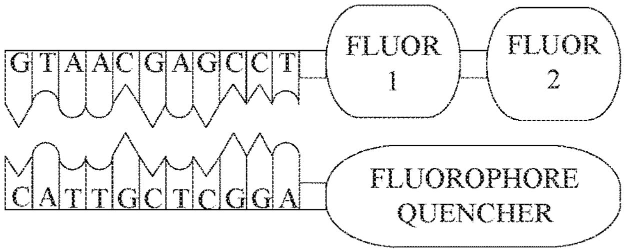
FIG. 1A shows a schematic representation of a probe hybrid complex (SEQ ID NOS: 8 and 9), wherein the first and second sequences are 100% complementary.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH2 group.

"Carboxy" refers to the —CO2H group.

"Cyano" refers to the —CN group.

"Formyl" refers to the —C(=O)H group.

"Hydroxy" or "hydroxyl" refers to the —OH group.

"Imino" refers to the =NH group.

"Nitro" refers to the —NO2 group.

"Oxo" refers to the =O substituent group.

"Sulfhydryl" refers to the —SH group.

"Thioxo" refers to the =S group.

"Alkyl" refers to a straight or branched hydrocarbon chain group consisting solely of carbon and hydrogen atoms, containing no unsaturation, having from one to twelve carbon atoms (C1-C12 alkyl), one to eight carbon atoms (C1-C8 alkyl) or one to six carbon atoms (C1-C6 alkyl), and which is attached to the rest of the molecule by a single bond, e.g., methyl, ethyl, n propyl, 1 methylethyl (iso propyl), n butyl, n pentyl, 1,1 dimethylethyl (t butyl), 3 methylhexyl, 2 methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n butylene, ethenylene, propenylene, n butenylene, propynylene, n butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(═Ra)(Rb)Rc, wherein each of Ra, Rb and Rc is as defined for compounds of structure (I).

"Alkoxy" refers to a group of the formula —ORa where Ra is an alkyl group as defined above containing one to twelve carbon atoms. Unless stated otherwise specifically in the specification, an alkoxy group is optionally substituted.

"Alkoxyalkylether" refers to a group of the formula —ORaRb where Ra is an alkylene group as defined above containing one to twelve carbon atoms, and Rb is an alkylether group as defined herein. Unless stated otherwise specifically in the specification, an alkoxyalkylether group is optionally substituted, for example substituted with an alcohol or —OP(═Ra)(Rb)Rc, wherein each of Ra, Rb and Rc is as defined for compounds of structure (I).

"Heteroalkyl" refers to an alkyl group, as defined above, comprising at least one heteroatom (e.g., N, O, P or S) within the alkyl group or at a terminus of the alkyl group. In some embodiments, the heteroatom is within the alkyl group (i.e., the heteroalkyl comprises at least one carbon-[heteroatom] x-carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkoxy" refers to a group of the formula —ORa where Ra is a heteroalkyl group as defined above containing one to twelve carbon atoms. Unless stated otherwise specifically in the specification, a heteroalkoxy group is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-[heteroatom]-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include ethylene oxide (e.g., polyethylene oxide) and the "C," "HEG," "TEG," "PEG 1K" and variations thereof, linking groups illustrated below:

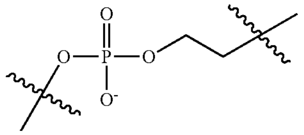

"C linker"

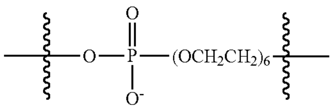

"HEG linker"

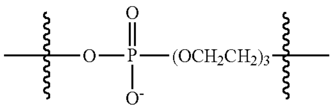

"TEG linker"

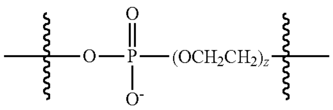

z > 0; e.g., z = 3-10

"EG linker"

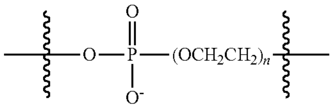

n = 22-26

"PEG 1K linker"

Multimers of the above C-linker, HEG linker and/or PEG 1K linker are included in various embodiments of heteroalkylene linkers.

In some embodiments of the PEG 1K linker, n is 25. Multimers may comprise, for example, the following structure:

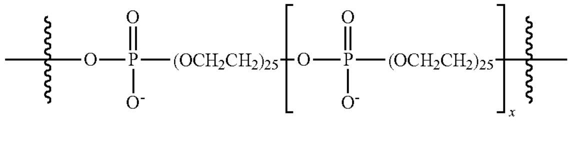

wherein x is 0 or an integer greater than 0, for example, x ranges from 0-100 (e.g., 1, 2, 3, 4, 5, 6, 7, 8, 9 or 10).

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of O, N, P and S, and multiple heteroatoms for example a linker having the formula —P(O—)(=O)O— or —OP(O—)(=O)O— and multimers and combinations thereof.

"Phosphate" refers to the —OP(=O)(Ra)Rb group, wherein Ra is OH, O— or ORc; and Rb is OH, O—, ORc, a thiophosphate group or a further phosphate group, wherein Rc is a counter ion (e.g., Na+ and the like).

"Phosphoalkyl" refers to the —OP(=O)(Ra)Rb group, wherein Ra is OH, O— or ORc; and Rb is —Oalkyl, wherein Rc is a counter ion (e.g., Na+ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=Ra)(Rb)Rc, wherein each of Ra, Rb and Rc is as defined for compounds of structure (I).

"Phosphoalkylether" refers to the —OP(=O)(Ra)Rb group, wherein Ra is OH, O— or ORc; and Rb is —Oalkylether, wherein Rc is a counter ion (e.g., Na+ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether, thiophosphoalkylether or —OP(=Ra)(Rb)Rc, wherein each of Ra, Rb and Rc is as defined for compounds of structure (I).

"Thiophosphate" refers to the —OP(=Ra)(Rb)Rc group, wherein Ra is O or S, Rb is OH, O—, S—, ORd or SRd; and Rc is OH, SH, O—, S—, ORd, SRd, a phosphate group or a further thiophosphate group, wherein Rd is a counter ion (e.g., Na+ and the like) and provided that: i) Ra is S; ii) Rb is S— or SRd; iii)Rc is SH, S— or SRd; or iv) a combination of i), ii) and/or iii).

"Thiophosphoalkyl" refers to the —OP(=Ra)(Rb)Rc group, wherein Ra is O or S, Rb is OH, O—, S—, ORd or SRd; and Rc is —Oalkyl, wherein Rd is a counter ion (e.g., Na+ and the like) and provided that: i) Ra is S; ii) Rb is S— or SRd; or iii)Ra is S and Rb is S— or SRd. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=Ra)(Rb)Rc, wherein each of Ra, Rb and Rc is as defined for compounds of structure (I).

"Thiophosphoalkylether" refers to the —OP(=Ra)(Rb)Rc group, wherein Ra is O or S, Rb is OH, O—, S—, ORd or SRd; and Rc is —Oalkylether, wherein Rd is a counter ion (e.g., Na+ and the like) and provided that: i) Ra is S; ii) Rb is S— or SRd; or iii)Ra is S and Rb is S— or SRd. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=Ra)(Rb)Rc, wherein each of Ra, Rb and Rc is as defined for compounds of structure (I).

"Carbocyclic" refers to a stable 3 to 18 membered aromatic or non aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptly, and cyclooctyl. Polycyclic cycloalkyls include, for example, adamantyl, norbornyl, decalinyl, 7,7 dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3 to 18 membered aromatic or non aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1 oxo thiomorpholinyl, and 1,1 dioxo thiomorpholinyl. Unless stated otherwise specifically in the specification, a heterocyclic group is optionally substituted.

"Heteroaryl" refers to a 5 to 14 membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4 benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo [1,2 a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2 oxoazepinyl, oxazolyl, oxiranyl, 1 oxidopyridinyl, 1 oxidopyrimidinyl, 1-oxidopyrazinyl, 1-oxidopyridazinyl, 1 phenyl 1H pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, alkoxyalkylether, heteroalkyl, heteroalkoxy, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NRgRh, —NRgC(═O)Rh, —NRgC(═O)NRgRh, —NRgC(═O)ORh, —NRgSO2Rh, —OC(═O)NRgRh, —ORg, —SRg, —SORg, —SO2Rg, —OSO2Rg, —SO2ORg, =NSO2Rg, and —SO2NRgRh. "Substituted also means any of the above groups in which one or more hydrogen atoms are replaced with —C(═O)Rg, —C(═O)ORg, —C(═O)NRgRh, —CH2SO2Rg, —CH2SO2NRgRh. In the foregoing, Rg and Rh are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In some embodiments, the optional substituent is —OP(═Ra)(Rb)Rc, wherein each of Ra, Rb and Rc is as defined for compounds of Structure (I). In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1, 3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

As used herein, "nucleic acid" or "nucleic acid molecule" or "polynucleotide" refers to any of deoxyribonucleic acid (DNA) or ribonucleic acid (RNA), including oligonucleotides.

The nucleic acid can represent a coding strand or its complement. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Nucleotides in a nucleic acid sequence are named according to standard IUPAC convention. Specifically, "A" is Adenine, "C" is Cytosine, "G" is Guanine, "T" is Thymine, "U" is Uracil, which refer to the following structures:

A

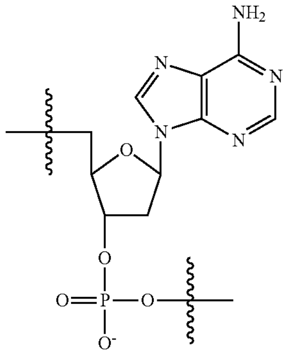

C

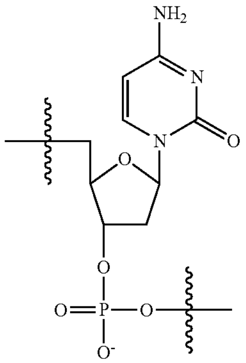

G

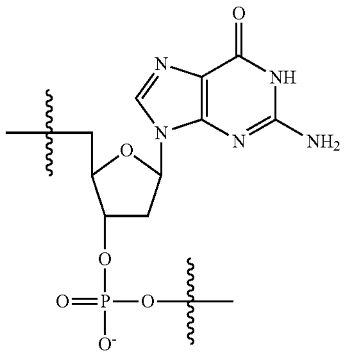

T

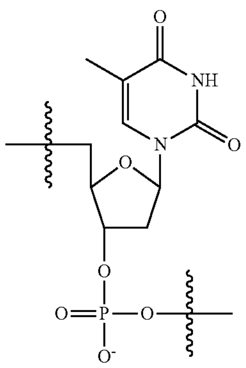

-continued

U

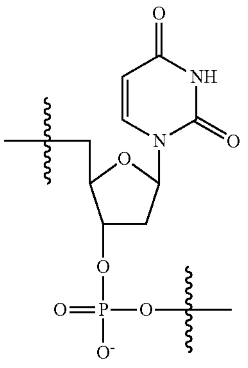

A sequence of a polynucleotide refers to the order in which nucleotides are arranged in a polynucleotide.

Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. In various embodiments, modified internucleotide linkages are used. Modified internucleotide linkages are well known in the art and include methylphosphonates, phosphorothioates, phosphorodithionates, phosphoroamidites and phosphate ester linkages. Nucleic acid molecules can be either single stranded or double stranded.

The terms "target, "target sequence", "target region", and "target nucleic acid," as used herein, refer to a region or subsequence of a nucleic acid which is to be detected.

The term "hybridization" as used herein refers to any process by which a first strand of nucleic acid binds with a second strand of nucleic acid through base pairing. Hybridization can occur between fully complementary nucleic acid strands or between "substantially complementary" nucleic acid strands that contain minor regions of mismatch.

As used herein, a probe is a polynucleotide that is "specific," for a target sequence if, when used under sufficiently stringent conditions, the probe hybridizes primarily only to the target nucleic acid. Typically, a probe is specific for a target sequence if the probe-target duplex stability is greater than the stability of a duplex formed between the probe and any other sequence found in the sample. One of skill in the art will recognize that various factors, such as salt conditions as well as base composition of the probe and the location of the mismatches, will affect the specificity of the probe, and that routine experimental confirmation of the probe specificity will be needed in most cases. Hybridization conditions can be chosen under which the probe can form stable duplexes only with a target sequence. Thus, the use of target-specific probes under suitably stringent conditions enables the specific amplification of those target sequences which contain the target probe binding sites. The use of sequence-specific conditions enables the specific binding of the probes to the target sequences which contain the exactly complementary probe binding sites.

Conditions under which only fully complementary nucleic acid strands will hybridize are referred to as "stringent hybridization conditions" or "sequence-specific hybridization conditions". The term "stringent" as used herein refers to hybridization conditions that are commonly understood in the art to define the conditions of the hybridization procedure. Stringency conditions can be low, high or medium, as those terms are commonly known in the art and well recognized by one of ordinary skill. In various embodiments, stringent conditions can include, for example, highly stringent conditions, and/or moderately stringent (i.e., medium stringency) conditions.

Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides.

It is understood in the art that a nucleic acid molecule need not be 100% complementary to a target nucleotide sequence to be specifically hybridizable. That is two or more nucleic acid molecules may be less than fully complementary and is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing 5 of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

The term "hybridization complex" as used herein refers to a complex formed between two nucleotide sequences by virtue of the formation of hydrogen bonds between complementary G and C bases and between complementary A and T bases; these hydrogen bonds may be further stabilized by base stacking interactions. The two complementary nucleotide sequences hydrogen bond in an antiparallel configuration. A hybridization complex may be formed in solution (e.g., Cot or Rot analysis) or between one nucleotide sequence present in solution and another nucleotide sequence immobilized on a solid support (e.g., paper, membranes, filters, chips, pins or glass slides, or any other appropriate substrate to which cells and/or nucleic acids have been fixed).

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 M−1 cm−1. The compounds of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the invention are useful for a wide variety of analytical applications, such as biochemical and biomedical applications, in which there is a need to determine the presence, location, or quantity of a particular analyte (e.g., biomolecule). In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Examples of such biological systems include cells, cell extracts, tissue samples, electrophoretic gels, assay mixtures, and hybridization reaction mixtures.

"Solid support" refers to any solid substrate known in the art for solid-phase support of molecules, for example a "microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene beads.

A "solid support reside" refers to the functional group remaining attached to a molecule when the molecule is cleaved from the solid support. Solid support residues are known in the art and can be easily derived based on the structure of the solid support and the group linking the molecule thereto.

A "targeting moiety" is a moiety that selectively binds or associates with a particular target, such as an analyte molecule. "Selectively" binding or associating means a targeting moiety preferentially associates or binds with the desired target relative to other targets. In some embodiments the compounds disclosed herein include linkages to targeting moieties for the purpose of selectively binding or associating the compound with an analyte of interest (i.e., the target of the targeting moiety), thus allowing detection of the analyte. Exemplary targeting moieties include, but are not limited to, antibodies, antigens, nucleic acid sequences, enzymes, proteins, cell surface receptor antagonists, and the like. In some embodiments, the targeting moiety is a moiety, such as an antibody, that selectively binds or associates with a target feature on or in a cell, for example a target feature on a cell membrane or other cellular structure, thus allowing for detection of cells of interest. Small molecules that selectively bind or associate with a desired analyte are also contemplated as targeting moieties in certain embodiments. One of skill in the art will understand other analytes, and the corresponding targeting moiety, that will be useful in various embodiments.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the invention disclosed herein are also meant to encompass all compounds of Structure (I), (II) or (III) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as 2H, 3H, 11C, 13C, 14C, 13N, 15N, 15O, 17O, 18O, 31P, 32P, 35S, 18F, 36Cl, 123I, and 125I, respectively.

Isotopically-labeled compounds of Structure (I) or (II) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present invention include all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

Embodiments of the compounds of the invention (e.g., compounds of structure I or II), or their salts, tautomers or solvates may contain one or more asymmetric centers and may thus give rise to enantiomers, diastereomers, and other stereoisomeric forms that may be defined, in terms of absolute stereochemistry, as (R) or (S) or, as (D) or (L) for amino acids. Embodiments of the present invention are meant to include all such possible isomers, as well as their racemic and optically pure forms. Optically active (+) and (−), (R) and (S), or (D) and (L) isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present invention, compounds useful as nucleotide probes in various analytical methods are provided. In general terms, embodiments of the present application are directed to compounds comprising at least two fluorophores or fluorophore quenchers, which are covalently bound to a polynucleotide. Without wishing to be bound by theory, it is believed a spacer between the fluorophores helps to maintain sufficient spatial distance between the fluorescent moieties such that intramolecular quenching is reduced or eliminated, thus resulting in a dye compound having a high fluorescence emission.

Accordingly, in some embodiments, compounds of the disclosure have the following structure (I):

(I)

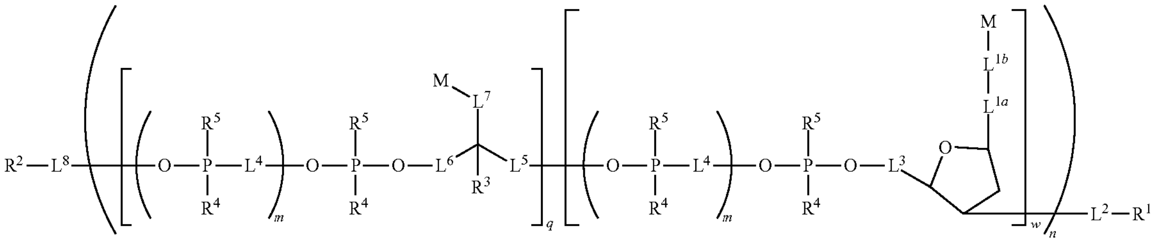

or a stereoisomer, salt or tautomer thereof, wherein:

M is, at each occurrence, independently either: a) the same or different fluorophore; or b) the same or different fluorophore quencher;

$L^{1a}$ is, at each occurrence, independently a heteroarylene linker;

$L^2$ and $L^8$ are independently optional linkers;

$L^{1b}$, $L^3$, $L^5$, $L^6$ and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$R^1$ and $R^2$ each independently comprise a polynucleotide or are each independently H, OH, SH, alkyl, alkoxy, alkylether, heteroalkyl or —OP(═$R_a$)($R_b$)$R_c$, provided at least one of $R^1$ and $R^2$ comprises a polynucleotide;

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

L' is, at each occurrence, independently a linker comprising a covalent bond to a solid support, a linker comprising a covalent bond to a solid support residue or a linker comprising a covalent bond to a nucleoside;

m is, at each occurrence, independently an integer of zero or greater;

n is an integer of one or greater; and q and w are, at each occurrence, independently 0 or 1, provided at least one occurrence of either q or w is 1.

In some embodiments, $M^1$ and $M^2$ are the same or different fluorophores. In other embodiments, $M^1$ and $M^2$ are the same or different fluorophore quenchers.

In embodiments, $R^1$ comprises a polynucleotide. In some embodiments, $R^2$ comprises a polynucleotide. In various embodiments, the polynucleotide has a sequence having at least 90% complementarity to a target nucleotide sequence.

In other embodiments, a composition of the present disclosure comprises a compound of structure (Ia) and a compound of structure (Ib):

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

L' is, at each occurrence, independently a linker comprising a covalent bond to a solid support, a linker comprising a covalent bond to a solid support residue or a linker comprising a covalent bond to a nucleoside;

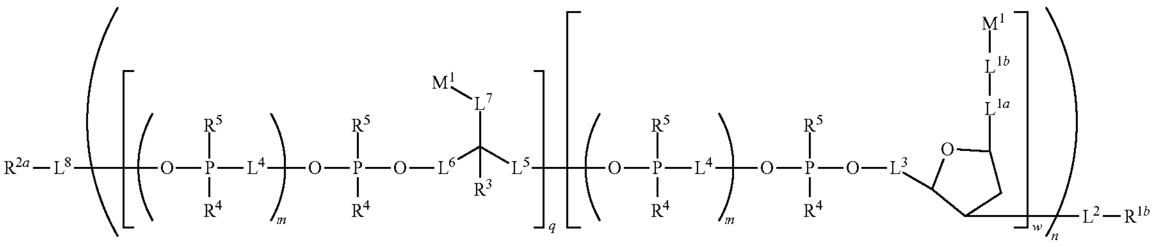

(Ia)

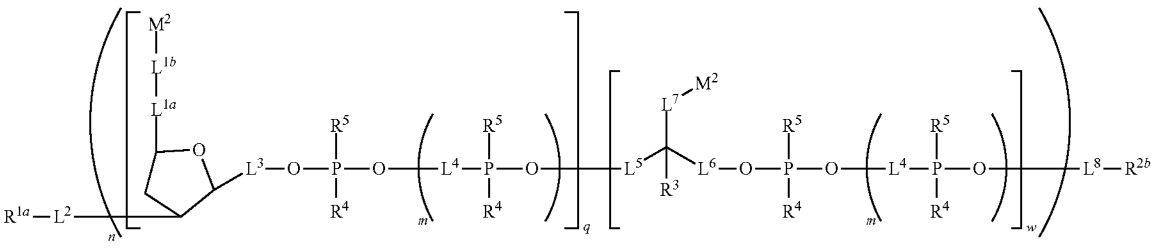

(Ib)

or a stereoisomer, salt or tautomer thereof, wherein:

$M^1$ is, at each occurrence, independently the same or different fluorophore;

$M^2$ is, at each occurrence, independently the same or different fluorophore quencher;

$L^{1a}$ is, at each occurrence, independently a heteroarylene linker;

$L^2$ and $L^8$ are independently optional linkers:

$L^{1b}$, $L^3$, $L^5$, $L^6$ and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$R^{1a}$ and $R^{2b}$ each independently comprise a polynucleotide or are each independently H, OH, SH, alkyl, alkoxy, alkylether, heteroalkyl or $—OP(=R_a)(R_b)R_c$, provided at least one of $R^{1a}$ and $R^{2b}$ comprise a polynucleotide;

$R^{1b}$ and $R^{2a}$ each independently comprise a polynucleotide or are each independently H, OH, SH, alkyl, alkoxy, alkylether, heteroalkyl or $—OP(=R_a)(R_b)R_c$, provided at least one of $R^{1a}$ and $R^{2b}$ comprise a polynucleotide;

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

m is, at each occurrence, independently an integer of zero or greater;

n is an integer of one or greater; and q and w are, at each occurrence, independently 0 or 1, provided at least one occurrence of either q or w is 1.

In embodiments, $R^{1a}$ and $R^{2a}$ comprise first and second polynucleotides, respectively, wherein the first polynucleotide comprises 4 to 40 nucleotides (e.g., 6 to 40, 10 to 20, 15 to 30, etc.), wherein the first polynucleotide has a first sequence and the second polynucleotide has a second sequence, and wherein the first sequence has at least 90% complementarity to at least a portion of the second sequence. In embodiments, $R^{1b}$ and $R^{2b}$ comprise third and fourth polynucleotides, respectively, wherein the third polynucleotide comprises 4 to 40 nucleotides (e.g., 6 to 40, 10 to 20, 15 to 30, etc.), wherein the third polynucleotide has a third sequence and the fourth polynucleotide has a fourth sequence, and wherein the third sequence has at least 90% complementarity to at least a portion of the fourth sequence.

In embodiments, $R^{1a}$ and $R^{1b}$ comprise first and second polynucleotides, respectively, and wherein the first polynucleotide nucleotide sequence comprises 4 to 40 nucleotides (e.g., 6 to 40, 10 to 20, 15 to 30, etc.), wherein the first polynucleotide has a first sequence and the second polynucleotide has a second sequence, and wherein the first sequence has at least 90% complementarity to at least a portion of the second nucleotide sequence. In embodiments, wherein $R^{2a}$ and $R^{2b}$ comprise third and fourth polynucleotides, respectively, wherein the third polynucleotide comprises 4 to 40 nucleotides, wherein the third polynucleotide has a third sequence and the fourth polynucleotide has a fourth sequence, and wherein the third sequence has at least 90% complementarity to at least a portion of the fourth sequence.

In embodiments, $R^{1b}$, $R^{2a}$ or both, have nucleotide sequences having at least 90% complementarity to a target nucleotide sequence.

In various embodiments, the second sequence, the third sequence, or both have at least 90% complementarity to a target nucleotide sequence.

In other embodiments, compounds of the present disclosure have the following structure (II):

phosphate, thiophosphate, phosphoalkyl, thiophosphoalkyl, phosphoalkylether or thiophosphoalkylether;

$R_d$ is a counter ion;

L' is, at each occurrence, independently a linker comprising a covalent bond to a solid support, a linker comprising a covalent bond to a solid support residue or a linker comprising a covalent bond to a nucleoside;

m is, at each occurrence, independently an integer of zero or greater;

n is an integer of one or greater; and (II)

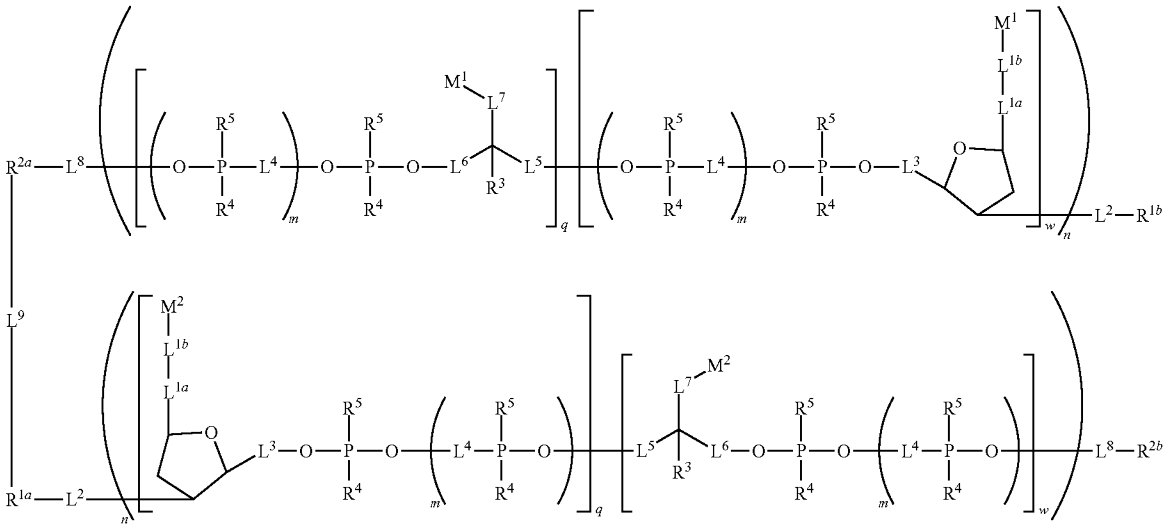

or a stereoisomer, salt or tautomer thereof, wherein:

$M^1$ is, at each occurrence, independently the same or different fluorophore;

$M^2$ is, at each occurrence, independently the same or different fluorophore quencher;

$L^{1a}$ is, at each occurrence, independently a heteroarylene linker;

$L^2$ and $L^8$ are independently optional linkers:

$L^{1b}$, $L^3$, $L^5$, $L^6$ and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$L^9$ is a linker comprising a polynucleotide;

$R^{1a}$ and $R^{2a}$ each independently comprise a polynucleotide;

$R^{1b}$ and $R^{2b}$ each independently comprise a polynucleotide or are each independently H, OH, SH, alkyl, alkoxy, alkylether, heteroalkyl or $—OP(=R_a)(R_b)R_c$;

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, q and w are, at each occurrence, independently 0 or 1, provided at least one occurrence of either q or w is 1.

In embodiments, $R^{1a}$ and $R^{2a}$ comprise first and second polynucleotides, respectively, wherein the first polynucleotide comprises 4 to 40 nucleotides, wherein the first polynucleotide has a first sequence and the second polynucleotide has a second sequence, and wherein the first sequence has at least 90% complementarity to at least a portion of the second sequence. In some embodiments, $R^{1b}$ and $R^{2b}$ comprise third and fourth polynucleotides, respectively, wherein the third polynucleotide comprises 4 to 40 nucleotides, wherein the third polynucleotide has a third sequence and the fourth polynucleotide has a fourth sequence, and wherein the third sequence has at least 90% complementarity to at least a portion of the fourth sequence.

In embodiments, $L^9$ comprises a fifth polynucleotide having at least 90% complementarity to a target nucleotide sequence. In embodiments, the fifth polynucleotide has at least 92% complementarity to the target nucleotide sequence. In embodiments, the fifth polynucleotide has at least 95% complementarity to the target nucleotide sequence. In embodiments, the fifth polynucleotide has at least 97% complementarity to the target nucleotide sequence. In embodiments, the fifth polynucleotide has at least 98% complementarity to the target nucleotide sequence. In embodiments, the fifth polynucleotide has at least 99% complementarity to the target nucleotide sequence.

In further embodiments, compounds of the present disclosure have the following structure (III):

(III)

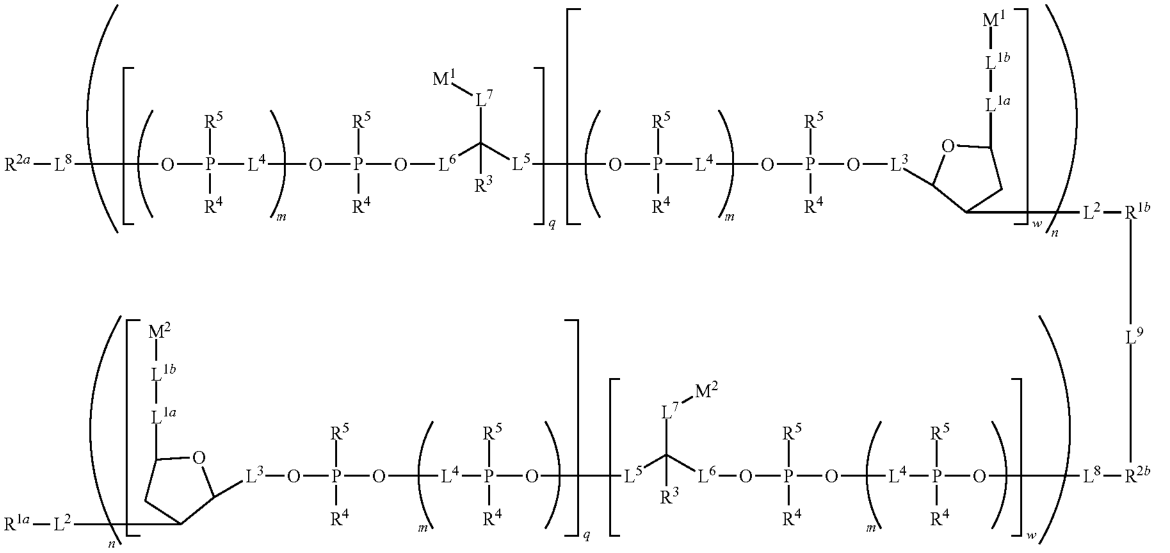

or a stereoisomer, salt or tautomer thereof, wherein:

$M^1$ is, at each occurrence, independently the same or different fluorophore;

$M^2$ is, at each occurrence, independently the same or different fluorophore quencher;

$L^{1a}$ is, at each occurrence, independently a heteroarylene linker;

$L^2$ and $L^8$ are independently optional linkers:

$L^{1b}$, $L^3$, $L^5$, $L^6$ and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$L^9$ is a linker comprising a polynucleotide;

$R^{1a}$ and $R^{2a}$ each independently comprise a polynucleotide or are each independently H, OH, SH, alkyl, alkoxy, alkylether, heteroalkyl or —OP(=$R_a$)($R_b$)$R_c$;

$R^{1b}$ and $R^{2b}$ each independently comprise a polynucleotide;

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

L' is, at each occurrence, independently a linker comprising a covalent bond to a solid support, a linker comprising a covalent bond to a solid support residue or a linker comprising a covalent bond to a nucleoside;

m is, at each occurrence, independently an integer of zero or greater;

n is an integer of one or greater; and q and w are, at each occurrence, independently 0 or 1, provided at least one occurrence of either q or w is 1.

In embodiments, $R^{1b}$ and $R^{2b}$ comprise first and second polynucleotides, respectively, wherein the first polynucleotide comprises 4 to 40 nucleotides, wherein the first polynucleotide has a first sequence and the second polynucleotide has a second sequence, and wherein the first sequence has at least 90% complementarity to at least a portion of the second sequence. In embodiments, $R^{1a}$ and $R^{2a}$ comprise third and fourth polynucleotides, respectively, wherein the third polynucleotide comprises 4 to 40 nucleotides, wherein the third polynucleotide has a third sequence and the fourth polynucleotide has a fourth sequence, and wherein the third sequence has at least 90% complementarity to at least a portion of the fourth sequence.

The polynucleotides in any of structures (I), (II) or (III), when at a terminal portion of the compound may terminate in any acceptable group. For example, certain polynucleotides will terminate in either a hydroxyl or phosphate group. In other various embodiments, the polynucleotides will terminate in —OP(=$R_a$)($R_b$)$R_c$, wherein $R_c$ is OL' and $R_a$ and $R_b$ are as defined above. In some of those embodiments, L' is a heteroalkylene linker to a solid support, a solid support residue or a nucleoside. In some embodiments, L' comprises an alkylene oxide or phosphodiester moiety, or combinations thereof. In certain embodiments, L' has the following structure:

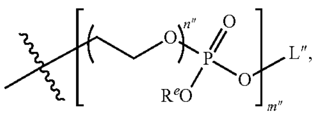

wherein:

m" and n" are independently an integer from 1 to 10;

$R^e$ is H, an electron pair or a counter ion;

L" is $R^e$ or a direct bond or linkage to a solid support, a solid support residue or a nucleoside (e.g., deoxythymidine).

In some embodiments, the polynucleotides terminate in the following structure:

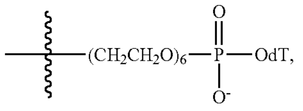

wherein dT is deoxythymidine.

In embodiments, wherein $L^9$ comprises a fifth polynucleotide having at least 90% complementarity to a target nucleotide sequence. In embodiments, the fifth polynucleotide has at least 92% complementarity to the target nucleotide sequence. In embodiments, the fifth polynucleotide has at least 92% complementarity to the target nucleotide sequence. In embodiments, the fifth polynucleotide has at least 95% complementarity to the target nucleotide sequence. In embodiments, the fifth polynucleotide has at least 97% complementarity to the target nucleotide sequence. In embodiments, the fifth polynucleotide has at least 98% complementarity to the target nucleotide sequence. In embodiments, the fifth polynucleotide has at least 99% complementarity to the target nucleotide sequence.

In embodiments, each occurrence of q is 0. In embodiments, at least one occurrence of q is 1. In embodiments, each occurrence of w is 0. In embodiments, at least one occurrence of w is 1. In embodiments, each occurrence of q is 0. In embodiments, at least one occurrence of $L^4$ is heteroalkylene, or wherein each occurrence of $L^4$ is heteroalkylene. In embodiments, the heteroalkylene comprises alkylene oxide. In other embodiments, the heteroalkylene comprises ethylene oxide. In some embodiments, $L^4$ has the following structure:

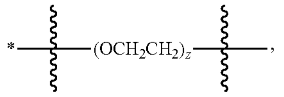

wherein:

z is an integer from 1 to 100; and indicates a bond to the adjacent phosphorous atom.

In embodiments, z is an integer from 3 to 6 or an integer from 22 to 26. In embodiments, at least one occurrence of $L^4$ is alkylene, or wherein each occurrence of $L^4$ is alkylene. In various embodiments, at least one alkylene is ethylene, or wherein each alkylene is ethylene. In further embodiments, at least one occurrence of $R^3$ is H, or wherein each occurrence of $R^3$ is H. In some embodiments, $L^{1a}$ is, at each occurrence independently an optionally substituted 5-7 membered heteroarylene linker. In embodiments, $L^{1a}$ has one of the following structures:

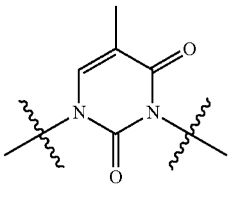

or

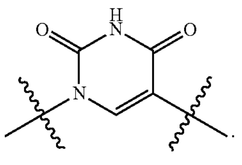

In embodiments, at least one occurrence of $L^3$ is an alkylene linker, or wherein each occurrence of $L^3$ is an alkylene linker. In some embodiments, at least one occurrence of $L^2$ and/or $L^8$ is absent, or wherein each occurrence of $L^2$ and/or $L^8$ is absent. In embodiments, at least one occurrence of $L^5$ and/or $L^6$ is alkylene, or wherein each occurrence of $L^5$ and/or $L^6$ is alkylene. In various embodiments, $L^{1b}$, at each occurrence, independently comprises an amide functional group or a triazolyl functional group.

In embodiments, $R^5$ is, at each occurrence, independently OH, $O^-$ or $OR_d$. In embodiments, wherein $R^4$ is, at each occurrence, oxo.

In embodiments, at least one occurrence of $L^7$ is an optionally substituted heteroalkylene linker, or wherein each occurrence of $L^7$ is independently an optionally substituted heteroalkylene linker. In embodiments, $L^7$ comprises an amide or a triazolyl functional group. In some embodiments, each occurrence of $L^7$ has one of the following structures:

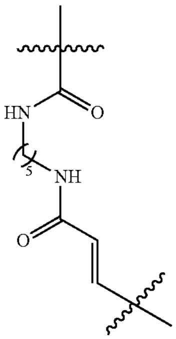

;

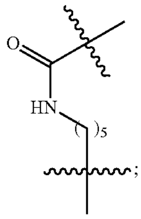

;

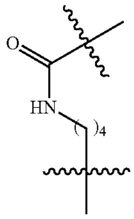

or

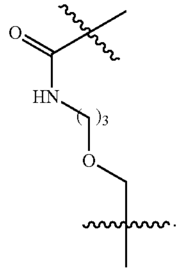

In embodiments, n is an integer from 1 to 100, or wherein n is an integer from 1 to 10, or from 2 to 10. For example, 1, 2, 3, 4, 5, 6, 7, 8, 9 or 10. In embodiments, m is an integer from 3 to 6, or wherein m is 3.

In embodiments, the fluorophore is, at each occurrence, independently a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety.

In embodiments, the fluorophore is, at each occurrence, independently pyrene, perylene, perylene monoimide, 5-FAM or 6-FAM or derivative thereof.

In further embodiments, the fluorophore is, at each occurrence, independently selected from Table 1.

TABLE 1
| Exemplary Fluorophores Structure |
|---|
| 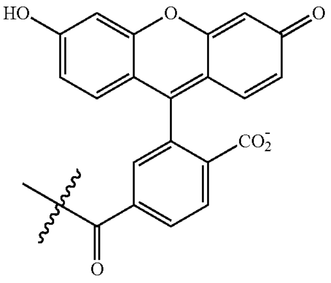 |
| F |
| 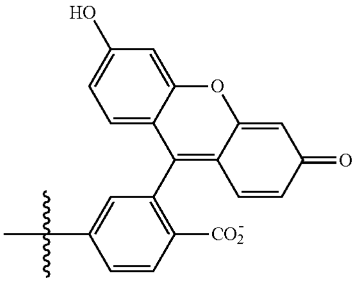 |
| 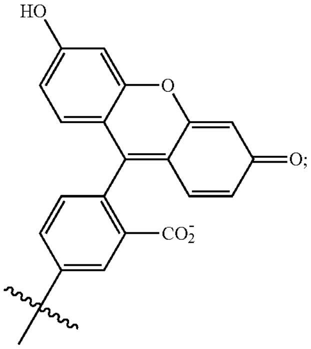 |
| 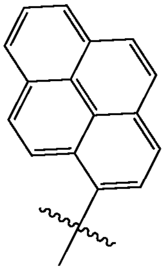 ; |
TABLE 1-continued
| Exemplary Fluorophores Structure |
|---|
| 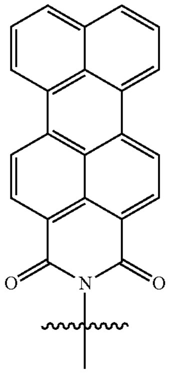 |
| 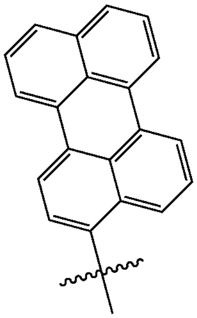 [SMILES: *c1ccc2c3cccc4cccc(c5cccc1c52)c43] |
| 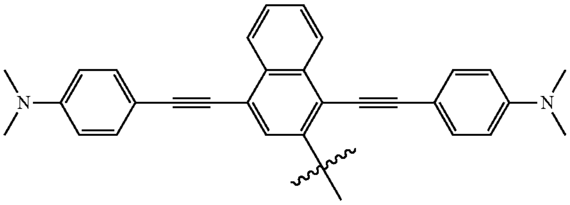 |
| 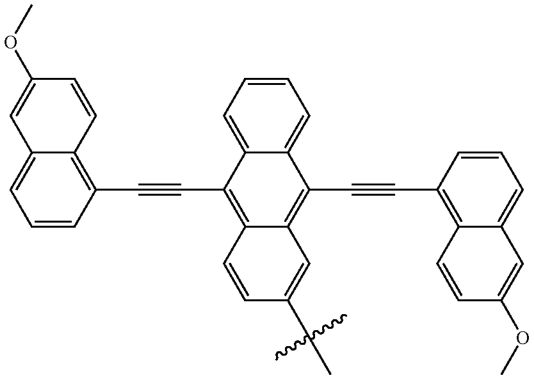 [SMILES: *c1ccc2c(C#Cc3cccc4cc(OC)ccc34)c3ccccc3c(C#Cc3cccc4cc(OC)ccc34)c2c1] |

TABLE 1-continued
| Exemplary Fluorophores Structure |
| --- |
| 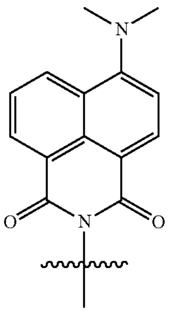 [SMILES: *N1C(=O)c2cccc3c(N(C)C)ccc(c23)C1=O] |
| 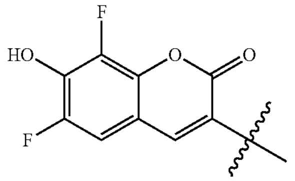 [SMILES: *c1cc2cc(F)c(O)c(F)c2oc1=O] |
| 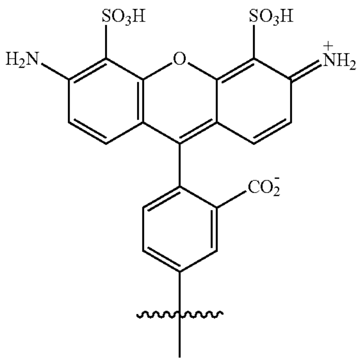 |
| 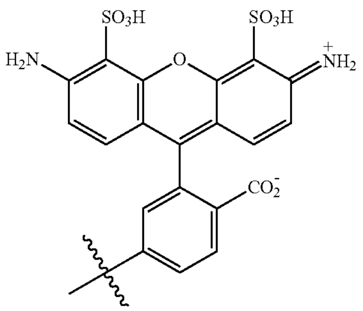 |
| 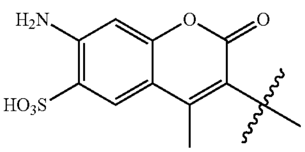 [SMILES: *c1c(C)c2cc(S(=O)(=O)O)c(N)cc2oc1=O] |
| 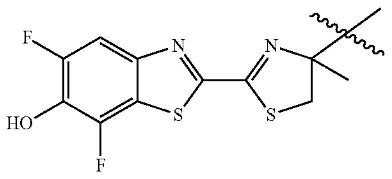 [SMILES: *C1(C)CSC(c2nc3cc(F)c(O)c(F)c3s2)=N1] |
TABLE 1-continued
| Exemplary Fluorophores Structure |
| --- |
| 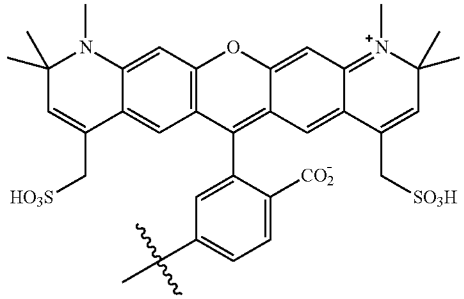 |
| 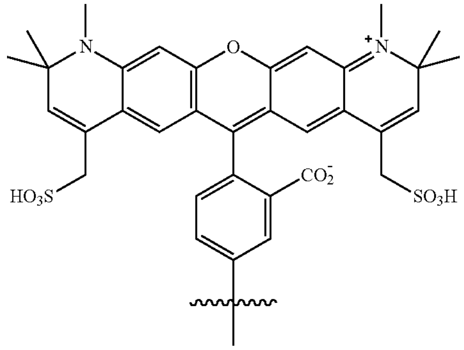 |
| 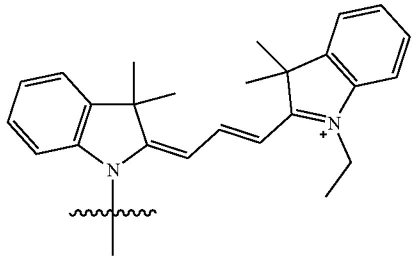 [SMILES: *N1/C(=C/C=C/C2=[N+](CC)c3ccccc3C2(C)C)C(C)(C)c2ccccc21] |
| 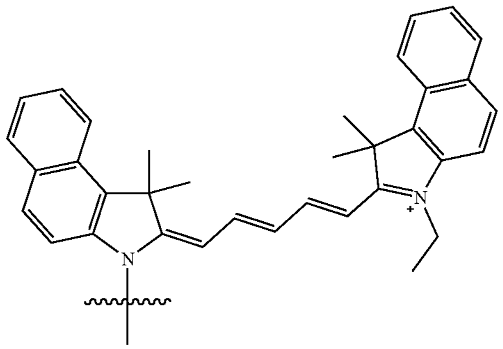 [SMILES: *N1/C(=C/C=C/C=C/C2=[N+](CC)c3ccc4ccccc4c3C2(C)C)C(C)(C)c2c1ccc1ccccc21] |
| 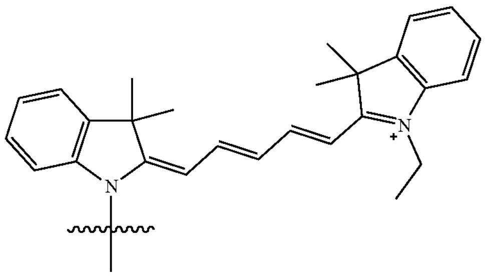 [SMILES: *N1/C(=C/C=C/C=C/C2=[N+](CC)c3ccccc3C2(C)C)C(C)(C)c2ccccc21] |

TABLE 1-continued
| Exemplary Fluorophores Structure |
|---|
| 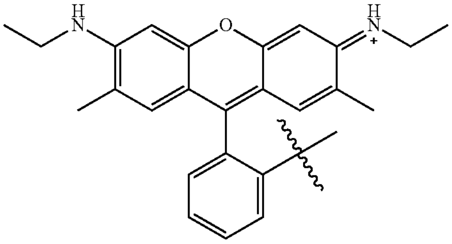 |
| 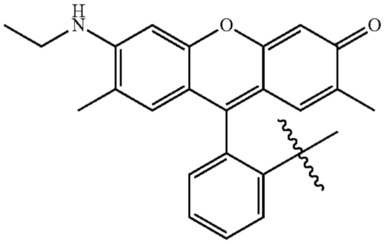 [SMILES: *c1ccccc1-c1c2cc(C)c(=O)cc-2oc2cc(NCC)c(C)cc12] |
| 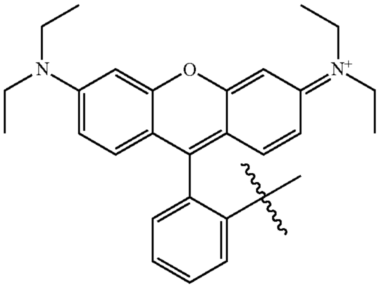 [SMILES: *c1ccccc1-c1c2ccc(=[N+](CC)CC)cc-2oc2cc(N(CC)CC)ccc12] |
| 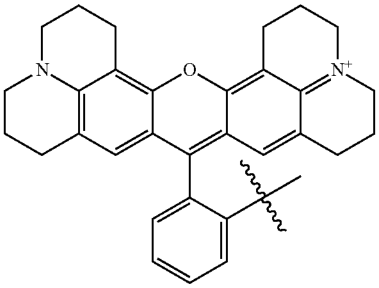 [SMILES: *c1ccccc1C1=c2cc3c4c(c2Oc2c1cc1c5c2CCCN5CCC1)CCC[N+]=4CCC3] |
| 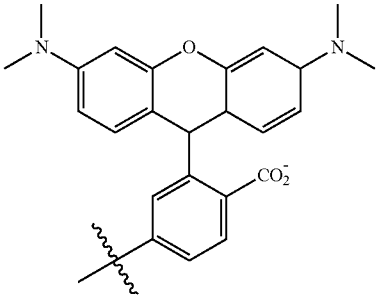 |
TABLE 1-continued
| Exemplary Fluorophores Structure |
|---|
| 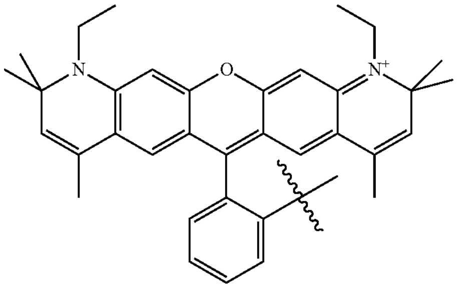 |
In particular embodiments, the fluorophore, at each occurrence, independently has one of the following structures:
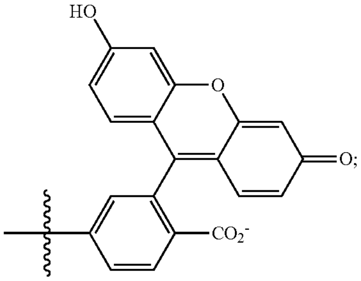
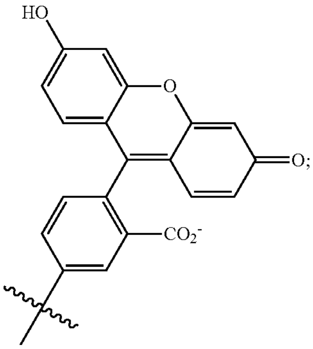
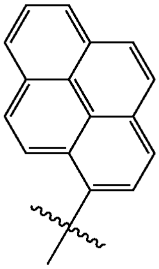
;
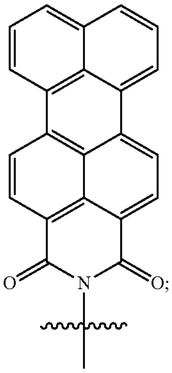
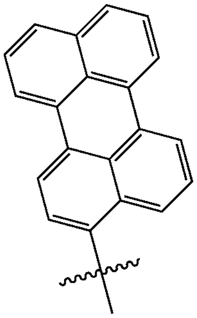
;

-continued
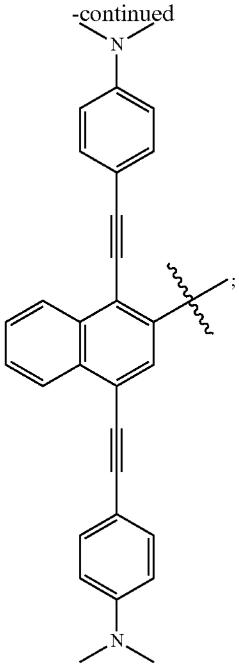
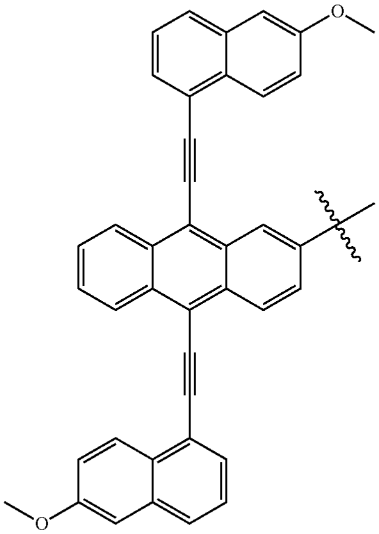
or
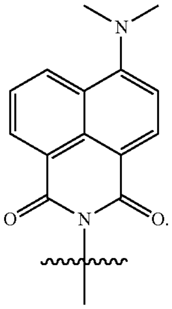
In embodiments, the fluorophore, at each occurrence, independently has one of the following structures:
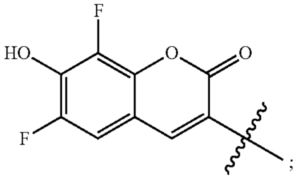
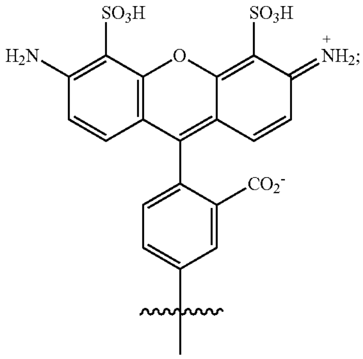
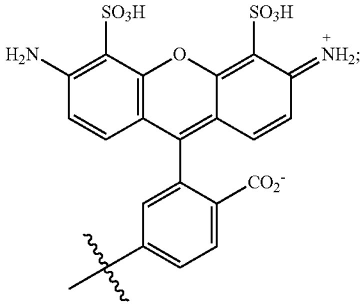
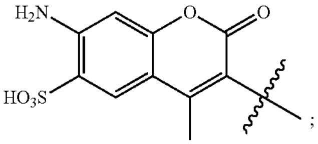
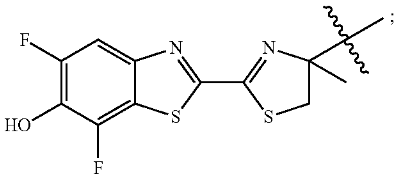
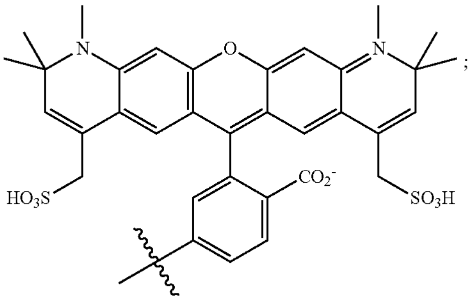

-continued
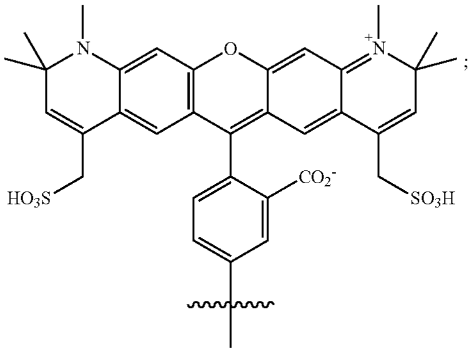
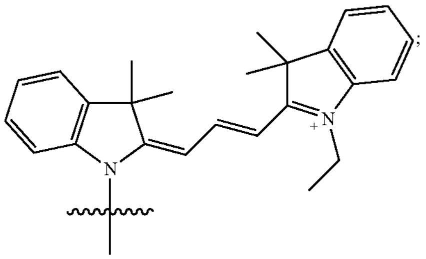
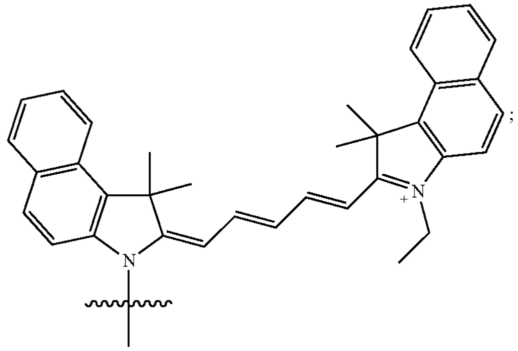
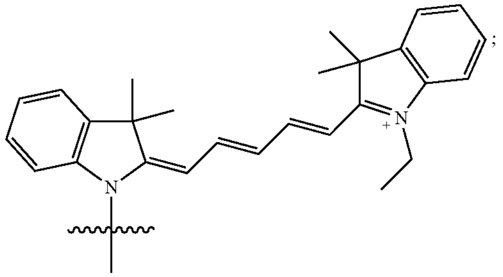
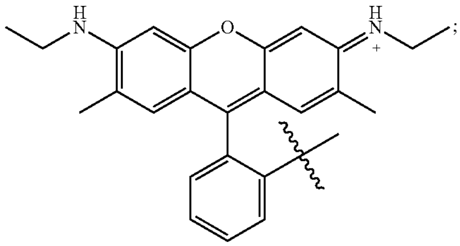
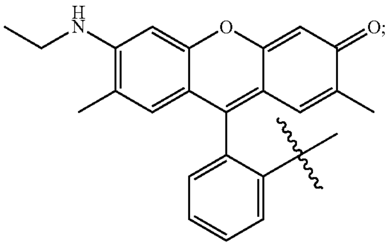
-continued
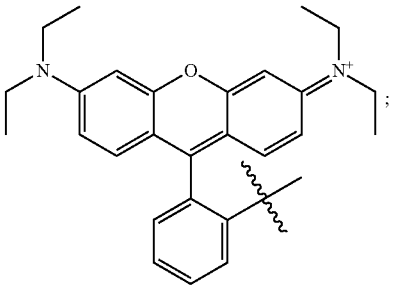
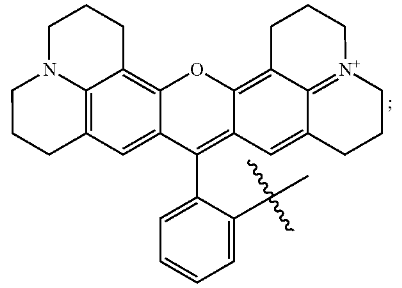
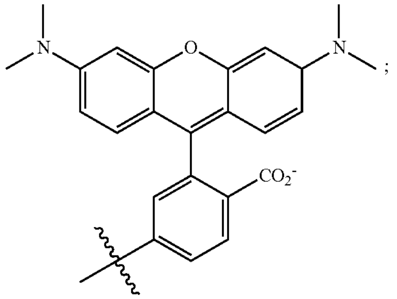
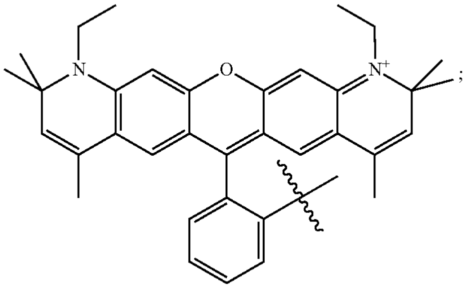
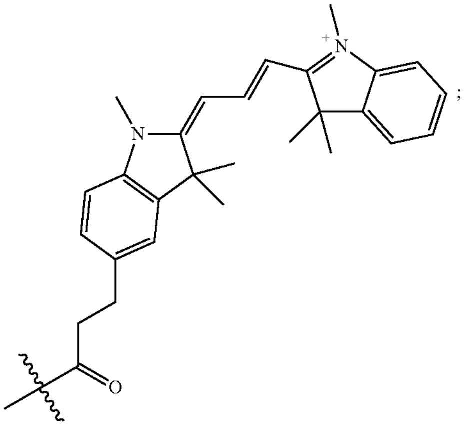

-continued
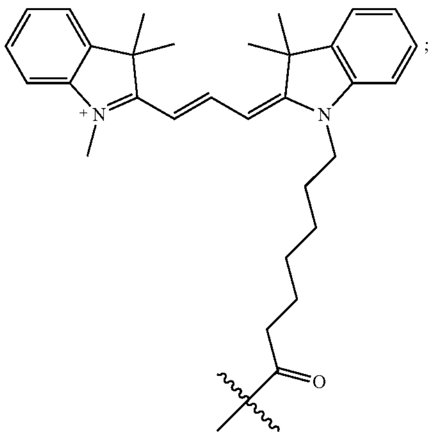
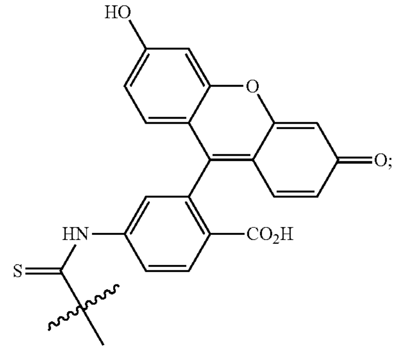
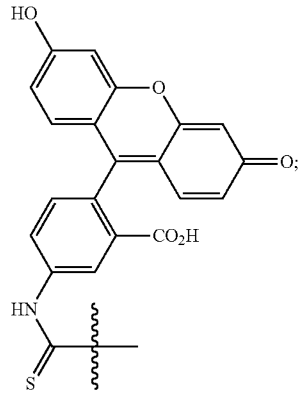
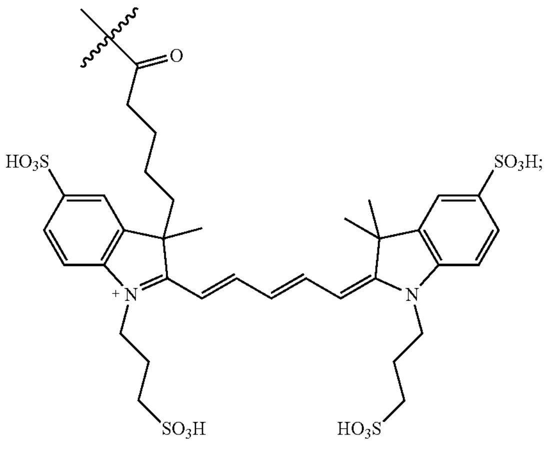
-continued
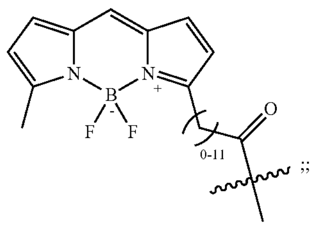
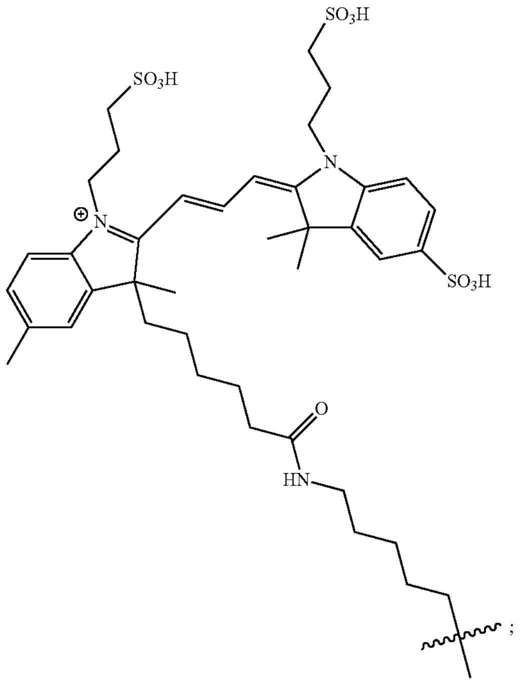
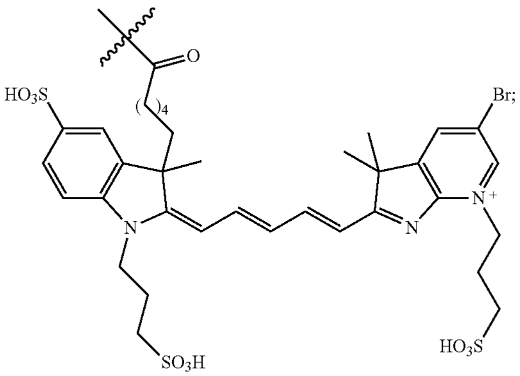
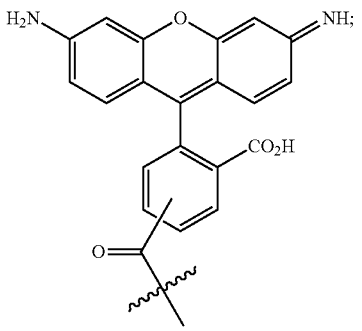

-continued
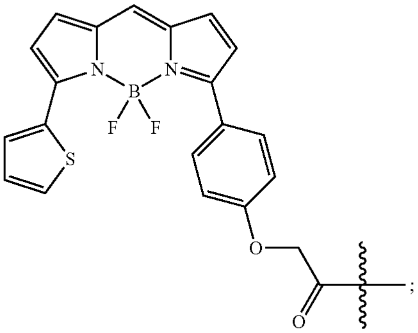
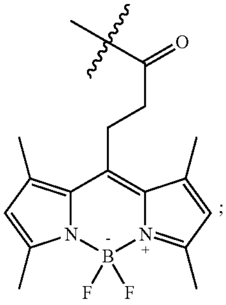
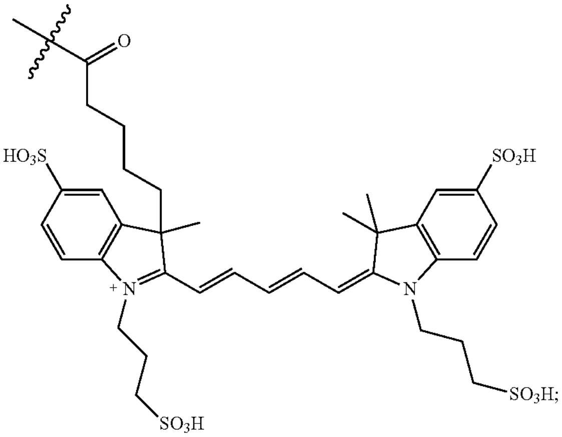
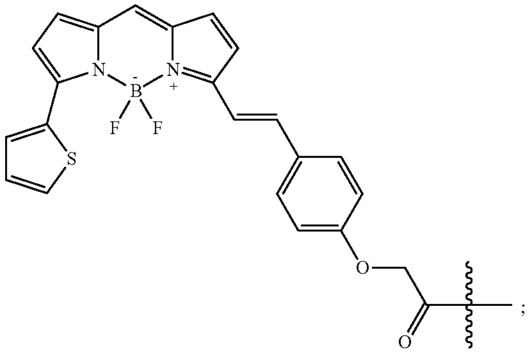
-continued
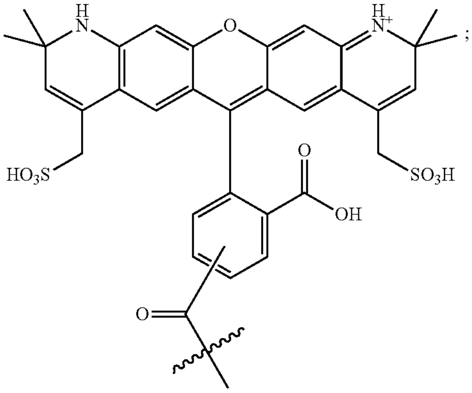
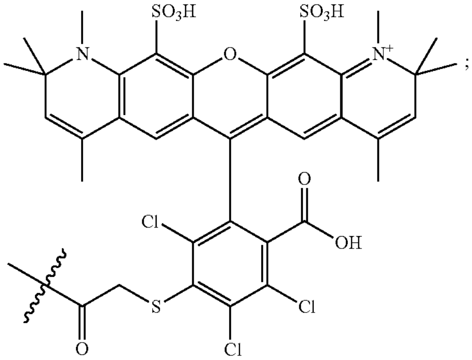
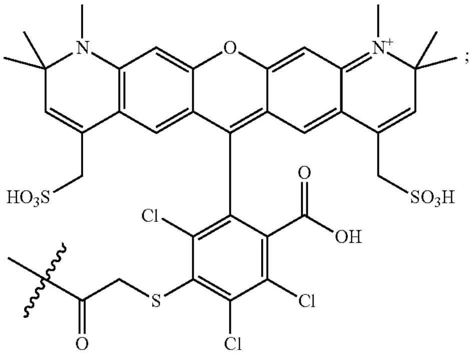
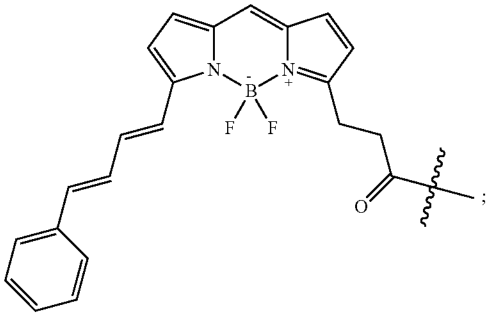

-continued
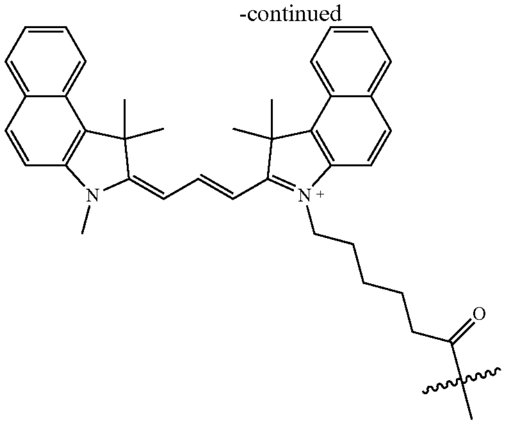
or
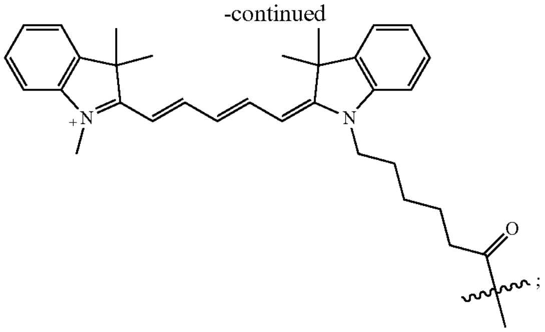
In further embodiments, the fluorophore quencher is, at each occurrence, independently selected from Table 2.
TABLE 2
| Exemplary Fluorophore quenchers<br>Structure |
|---|
| 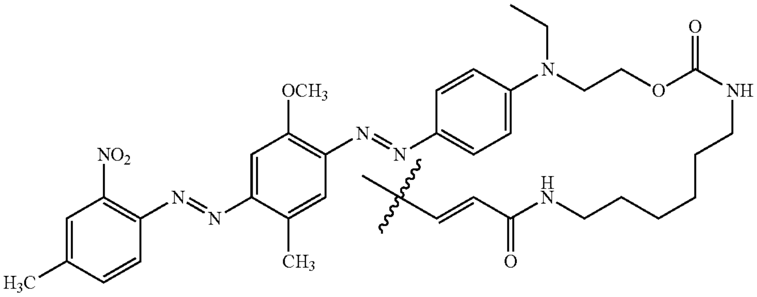 [SMILES: */C=C/C(=O)NCCCCCCNC(=O)OCCN(CC)c1ccc(/N=N/c2cc(C)c(/N=N/c3ccc(C)cc3[N+](=O)[O-])cc2OC)cc1]<br>BHQ1 |
| 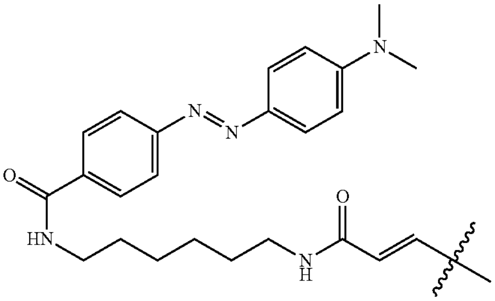 [SMILES: */C=C/C(=O)NCCCCCCNC(=O)c1ccc(/N=N/c2ccc(N(C)C)cc2)cc1]<br>DAB |
| 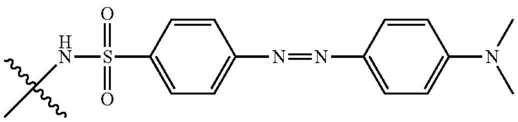 [SMILES: *NS(=O)(=O)c1ccc(N=Nc2ccc(N(C)C)cc2)cc1] |

TABLE 2-continued
| Exemplary Fluorophore quenchers Structure |
|---|
| 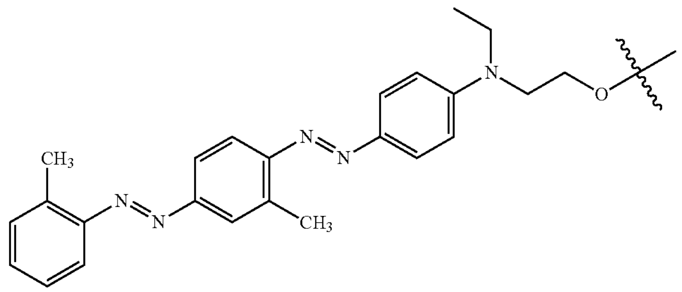 [SMILES: *OCCN(CC)c1ccc(/N=N/c2ccc(/N=N/c3ccccc3C)cc2C)cc1] |
| 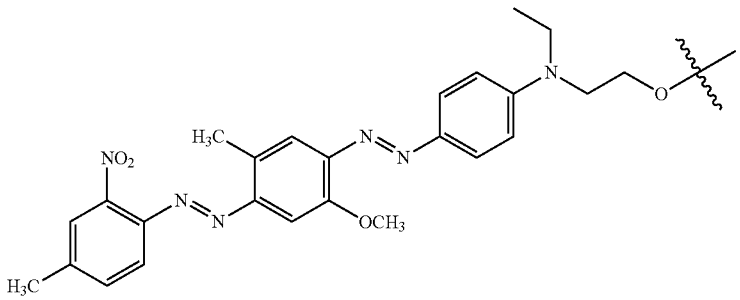 [SMILES: *OCCN(CC)c1ccc(/N=N/c2cc(C)c(/N=N/c3ccc(C)cc3[N+](=O)[O-])cc2OC)cc1] |
| 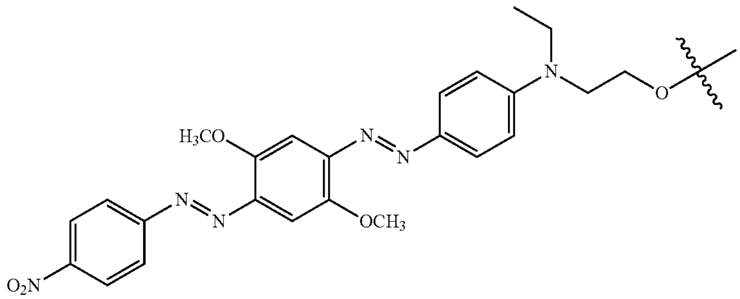 [SMILES: *OCCN(CC)c1ccc(/N=N/c2cc(OC)c(/N=N/c3ccc([N+](=O)[O-])cc3)cc2OC)cc1] |
| 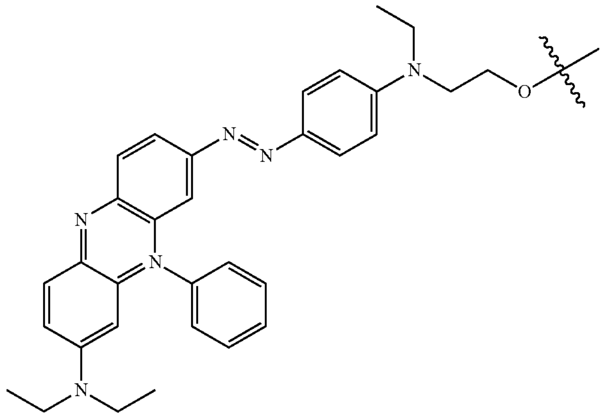 |

TABLE 2-continued
| Exemplary Fluorophore quenchers Structure |
|---|
| 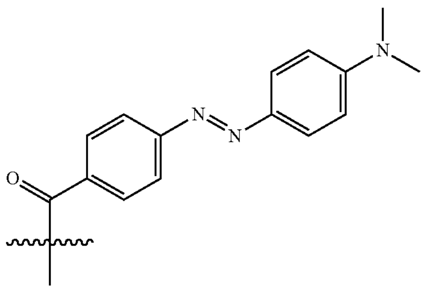 [SMILES: *C(=O)c1ccc(/N=N/c2ccc(N(C)C)cc2)cc1] |
| 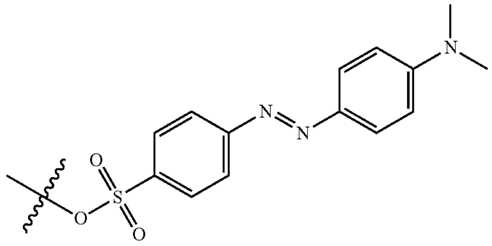 [SMILES: *OS(=O)(=O)c1ccc(/N=N/c2ccc(N(C)C)cc2)cc1] |
| 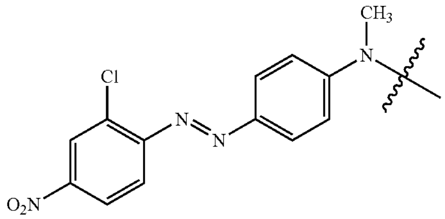 [SMILES: *N(C)c1ccc(/N=N/c2ccc([N+](=O)[O-])cc2Cl)cc1] |
| 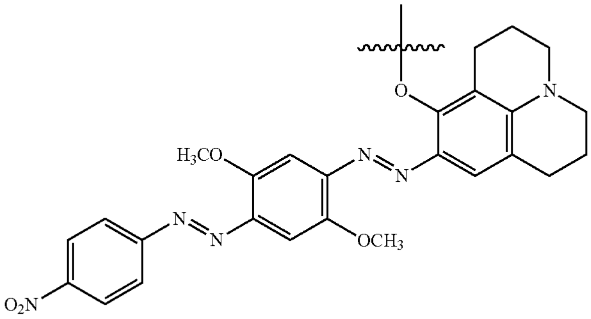 [SMILES: *Oc1c(/N=N/c2cc(OC)c(/N=N/c3ccc([N+](=O)[O-])cc3)cc2OC)cc2c3c1CCCN3CCC2] |
In some embodiments, the fluorophore quencher is, at each occurrence, independently, BHQ-1 or BHQ-2.
In other embodiments, the fluorophore quencher is, at each occurrence, independently,
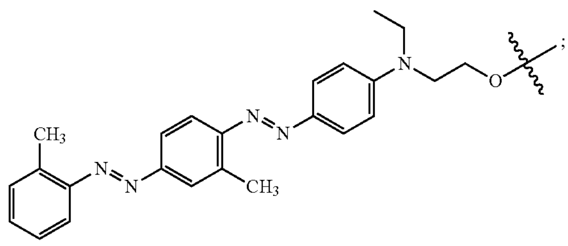
;
-continued
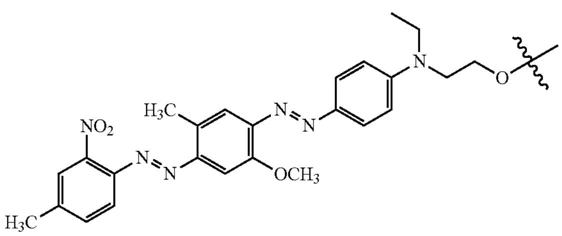
;

-continued

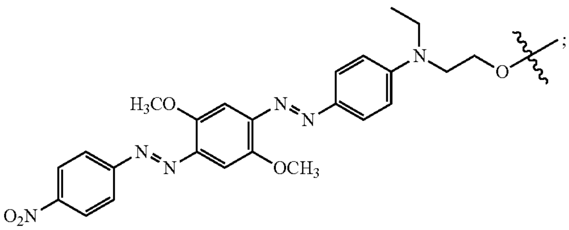
;

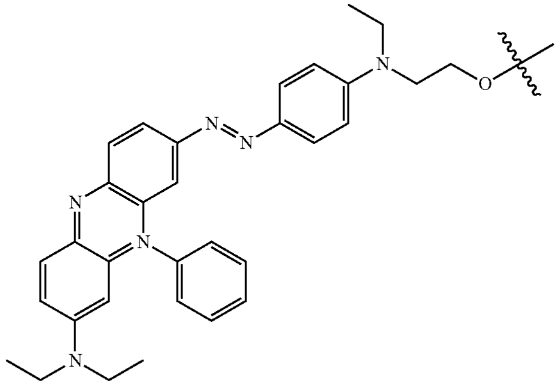
;

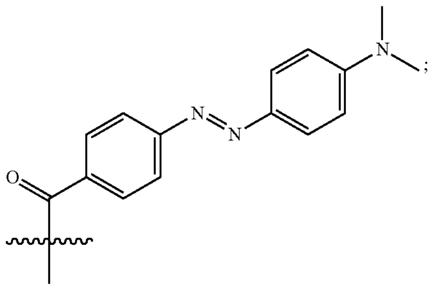
;

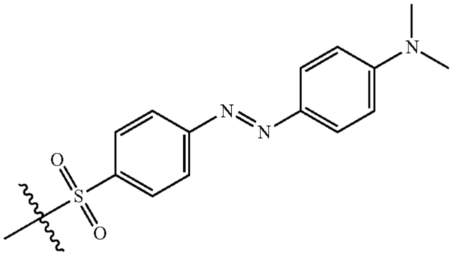
;

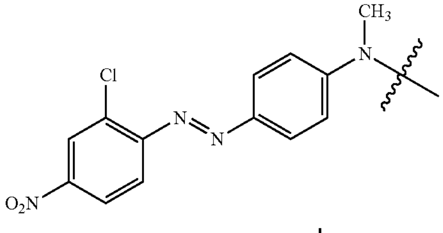
;

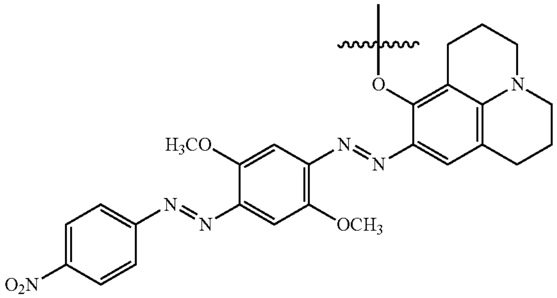
;

IRDye QC-1; Iowa Black FQ; Iowa Black RQ; OSY35; OSY7; OSY21; Cy5Q; Cy7Q; QXL 490; QXL 520; QXL 570; QXL 610; QXL 670; QXL 680; ATTO 540Q; ATTO 580Q or ATTO 612Q.

As is understood, the compounds (including detectable probes and quencher constructs) described herein can be formed using any suitable methods, such as those described in US 2017/0292957, US 2016/0208100, US 2016/0341736, US 2018/0065998, US 2018/0079909, and US 2019/0016898 which are incorporated by referenced in their entirety for such teachings.

Figure 1B:
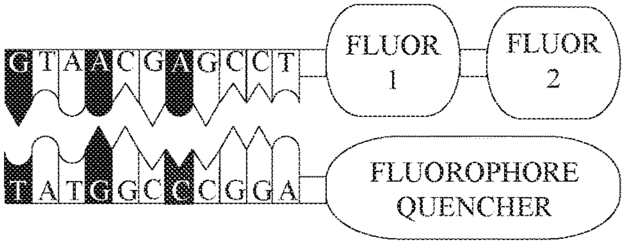
FIG. 1B shows a schematic representation of a probe hybrid complex (SEQ ID NOS: 8 and 10), wherein the first and second sequences are 73% complementary.

A schematic version of an illustrative detectable probe and an illustrative quencher molecule is shown in FIG. 1A. As shown, the polynucleotides on the left side are complementary and therefore hybridize to bring the fluorophores and the quencher into proximity. Although polynucleotides that are fully complementary are shown in FIG. 1A, some mismatched nucleotide pairs may be found in the polynucleotides, as shown in FIG. 1B. Although the degree of complementarity is less than 100%, it is still enough to bring the fluorophores and the quencher into proximity.

Figure 1C:
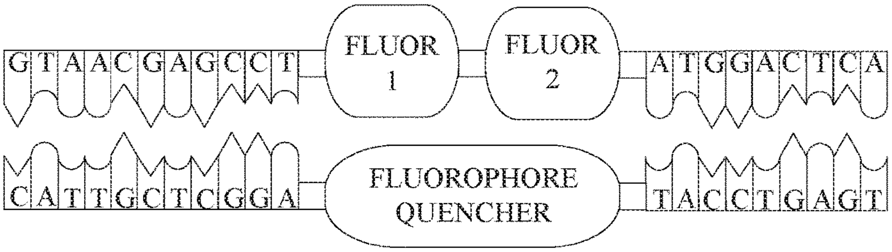
FIG. 1C shows a schematic representation of a probe hybrid complex (SEQ ID NO: 8 and 9), wherein the each pair of sequences is 100% complementary.

Further, polynucleotides may be bound to each side of the fluorophores and/or the quencher moiety. A schematic version of a pair of such constructs is shown in FIG. 1C. The sequences of the polynucleotides on both sides of the fluorophores and the quencher moiety have sufficient complementarity to hybridize, thus bringing the fluorophores and the quencher into proximity.

Figure 1D:
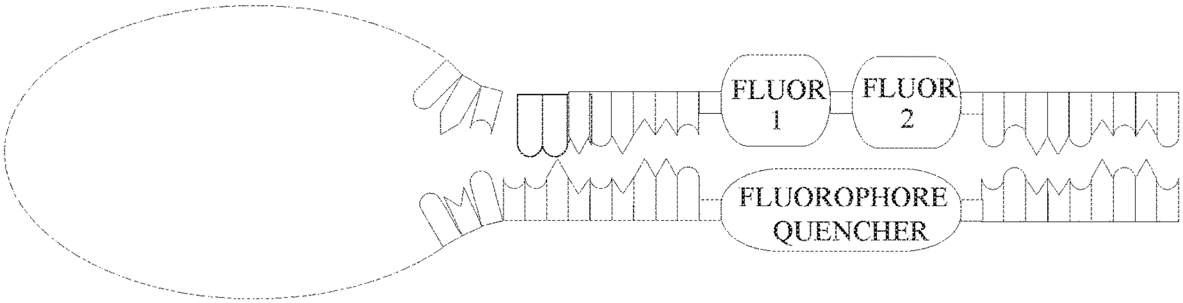
FIG. 1D shows a schematic representation of a probe according to some embodiments.

In further embodiments, a detectable probe comprises fluorophores and a quencher moiety, which is schematically illustrated in FIG. 1D. The portion of the polynucleotide that is complementary to the target sequence is found in the nucleotides of the loop structure on the left. Although polynucleotides are shown bound to both sides of the fluorophores and quencher moiety, in other embodiments, polynucleotides are bound to one side of the fluorophores and quencher moiety (similar to the constructs of FIG. 1A).

Embodiments of the disclosure also include a detectable probe for identifying the presence of a target nucleotide sequence, comprising:

- a first polynucleotide having a first end, the first polynucleotide having a first sequence that comprises a target complement sequence that has at least 90% complementarity to a target nucleotide sequence;
- a first polymer having a first end and a second end, the first end being covalently bound to the first end of the first polynucleotide, the first polymer comprising two fluorophores; and
- a second polynucleotide having a first end that is covalently bound to the second end of the first polymer.

In some embodiments, the detectable probe further comprises a second polymer having a first end and a second end, the first end being covalently bound to a second end of the first polynucleotide; and a third polynucleotide having a first end that is covalently bound to the second end of the second polymer.

In various embodiments, the second polynucleotide has a second sequence comprising a first control complement sequence, and the third polynucleotide has a third sequence comprising a second control complement sequence that has at least 75% complementarity to the first control complement sequence.

In various embodiments, such compositions or kits further comprising a quencher molecule comprising: a third polynucleotide having a first end; a second polymer having a first end and a second end, the first end being covalently bound to the first end of the third polynucleotide, the second polymer comprising two fluorophores; and a fourth polynucleotide having a first end that is covalently bound to the second end of the second polymer.

In various embodiments, the first sequence further comprises a first control complement sequence; and the third polynucleotide has a third sequence that comprises a second control complement sequence that is capable of hybridizing with the first control complement sequence. In some such embodiments, the first and second control sequences are complementary, as illustrated in FIG. 1A. In other embodiments, there are one or more mismatched nucleotides between the first and second control sequences, as illustrated in FIG. 1B.

In additional embodiments, the second polynucleotide has a second sequence that comprises a third control complement sequence; and the fourth polynucleotide has a fourth sequence that comprises a fourth control complement sequence that is capable of hybridizing with the third control complement sequence.

In any of the above embodiments, the target complement sequence is capable of hybridizing to the target nucleotide sequence with a first strength; and the first control complement sequence is capable of hybridizing to the second control complement sequence with a second strength that is less than the first strength.

Various embodiments of the present disclosure further comprise a detectable probe for identifying the presence of a target nucleotide sequence, comprising:

a) a first polynucleotide covalently bound to a first polymer comprising two or more fluorophores;

b) a second segment comprising a second nucleotide sequence covalently bound to a second polymer comprising two or more fluorophore quenchers;

wherein the first nucleotide sequence comprises: i) a target complement sequence having at least 90% complementarity to the target nucleic acid sequence, the target complement sequence capable of forming, with the target sequence, a double-stranded hybrid having a first strength under assay conditions; ii) and a probe complement sequence having at least 90% complementarity to at least a portion of the second nucleotide sequence, the probe complement sequence capable of forming, with at least the portion of the second nucleotide sequence, a double-stranded hybrid having a second strength under the assay conditions, the second strength being less than the first strength, and wherein the first polymer, in the absence of the second polymer, has a peak fluorescence emission upon excitation with a predetermined wavelength of ultraviolet light of at least 85% of the sum of the peak fluorescence emission of each individual fluorophore present in the first polymer upon excitation with the same wavelength of ultraviolet light.

In some such embodiments, the first nucleotide sequence is covalently bound to the second nucleotide sequence.

Also described herein are compositions comprising the detectable probes described, as well as kits comprising such compositions. In some such embodiments, a kit of the present disclosure further comprises instructions for use of the compound, composition, or detectable probe for identification of a target nucleotide sequence.

Further described are methods for identifying the presence of a target nucleotide sequence, comprising: producing a mixture by contacting a sample with the compound, composition, or detectable probe of described herein under assay conditions; and imaging the mixture under detection conditions.

In some embodiments, compounds of the present disclosure have the structure shown in Table 3. It is to be understood that the structures put forth in the below table are meant to be representative examples of embodiments of the invention.

In certain embodiments, compounds of Table 3 are fluorescent probe compounds wherein the M moiety is, at each occurrence, independently, the same or different fluorophore.

In more specific embodiments, compounds of structure III-1, III-2, III-3, III-IV or III-V of Table 3 are fluorescent probe molecules and the M moiety is a fluorophore. In a more specific embodiment, said fluorophore is selected from Table 1.

In other embodiments, compounds of Table 3 are fluorescent quenching compounds wherein the M moiety is, at each occurrence, independently, the same or different fluorophore quencher.

In still more specific embodiments, compounds of structure 111-6, 111-7, 111-8, III-9 or III-10 of Table 3 are fluorescent quenching molecules and the M moiety is a fluorophore quencher. In a more specific embodiment, said fluorophore quencher is selected from Table 2.

TABLE 3

Rμepresentative Structures

| No. | Structure |
| --- | --- |
| III-1 | 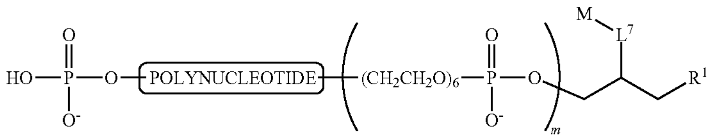 |
| III-2 | 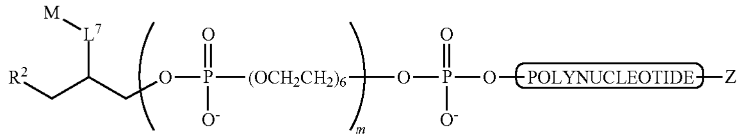 |

TABLE 3-continued
| Rμepresentative Structures | |
|---|---|
| No. | Structure |
| | 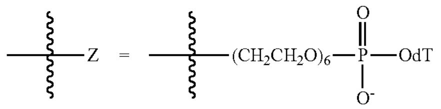 |
| III-3 | 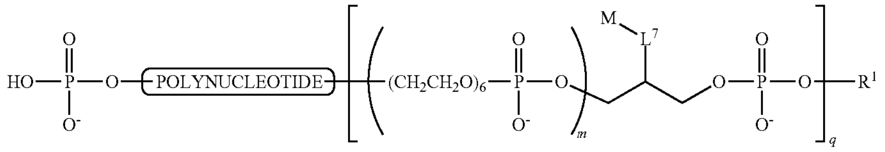 |
| III-4 | 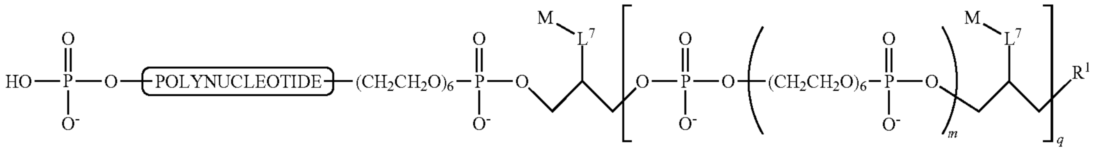 |
| III-5 | 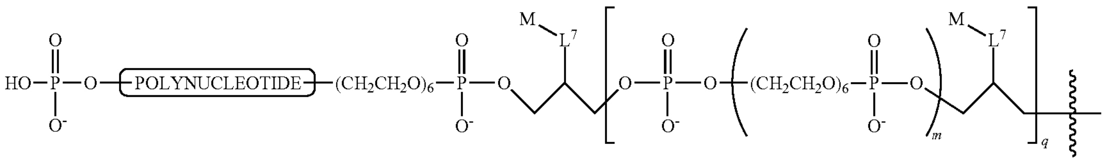 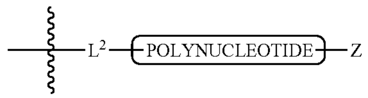 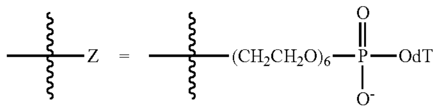 |
| III-6 | 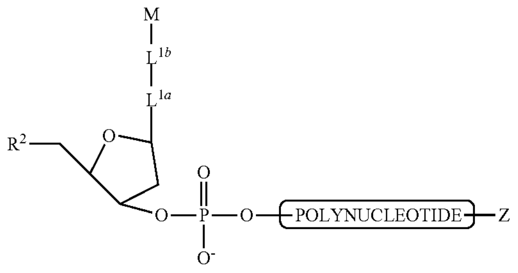 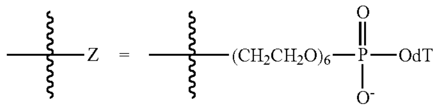 |
| III-7 | 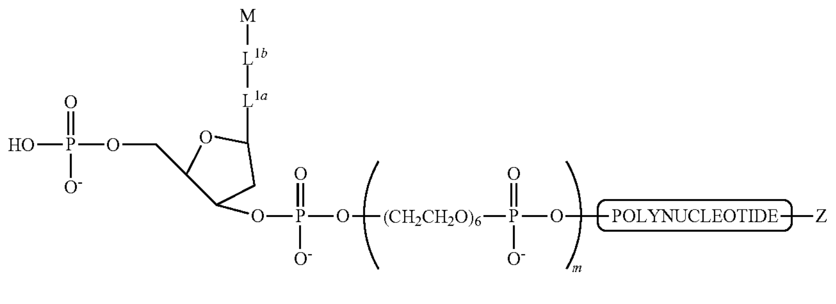 |

TABLE 3-continued
| Rμepresentative Structures | |
|---|---|
| No. | Structure |
| | 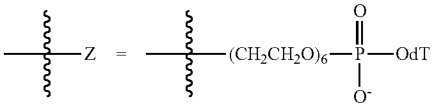 |
| III-8 | 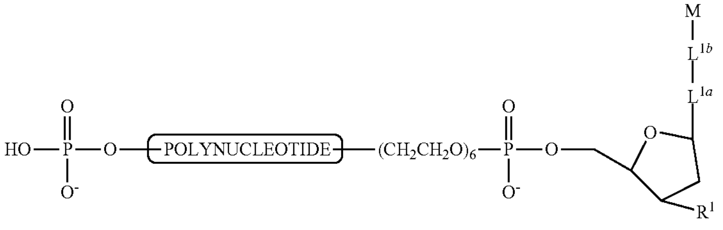 |
| III-9 | 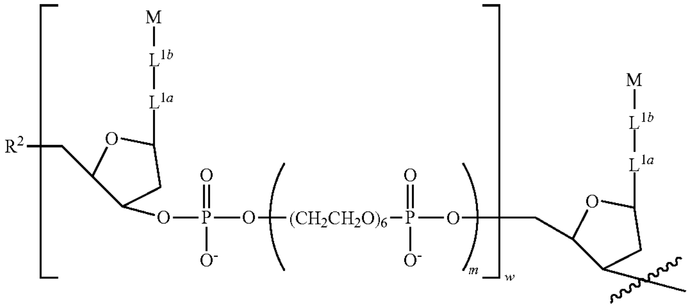 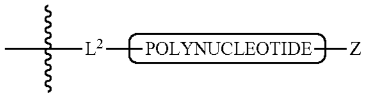 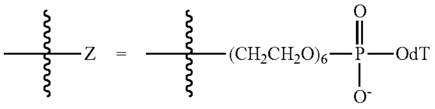 |
| III-10 | 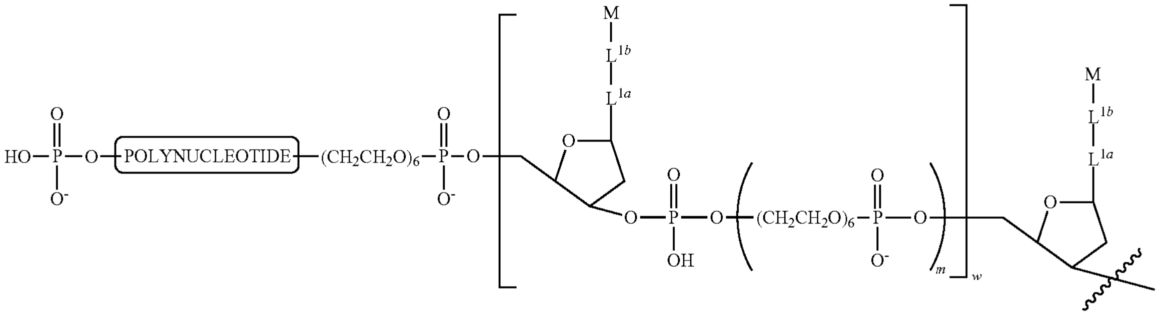 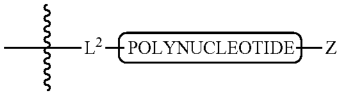 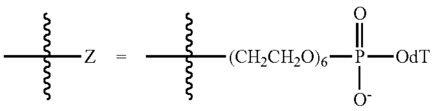 |

Table 4. Exemplary Fluorescent Probe Compounds of Structure (I)
TABLE 4
| Exemplary Fluorscent Probe Compounds of Structure (I) | |
|---|---|
| P-1 | 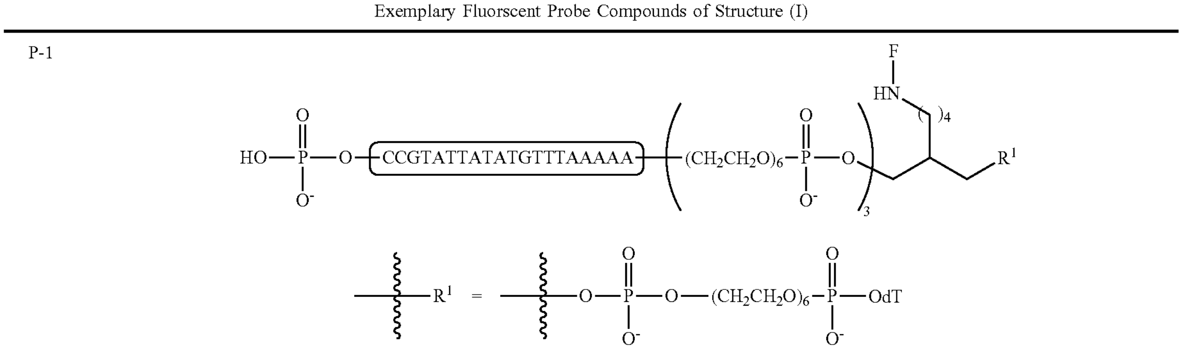 (SEQ ID NO: 1) |
| P-2 | 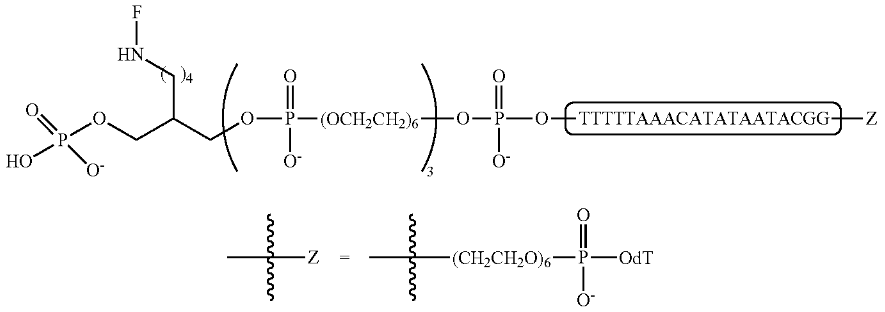 (SEQ ID NO: 2) |
| P-3 | 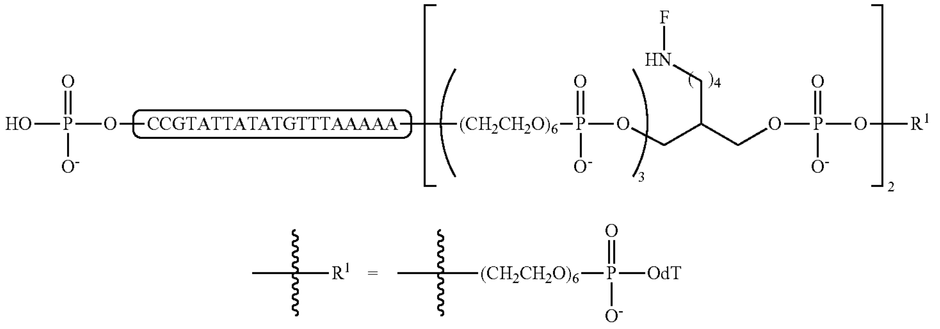 (SEQ ID NO: 1) |
| P-4 | 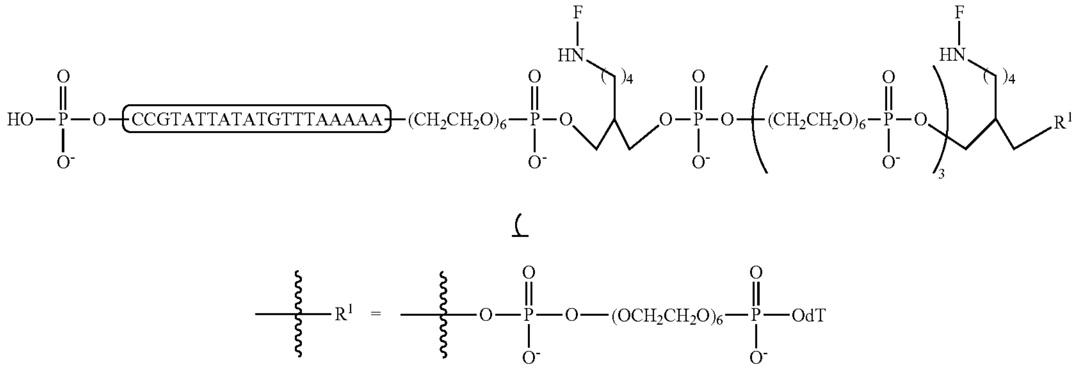 (SEQ ID NO: 1) |

TABLE 4-continued
Exemplary Fluorscent Probe Compounds of Structure (I)
P-5
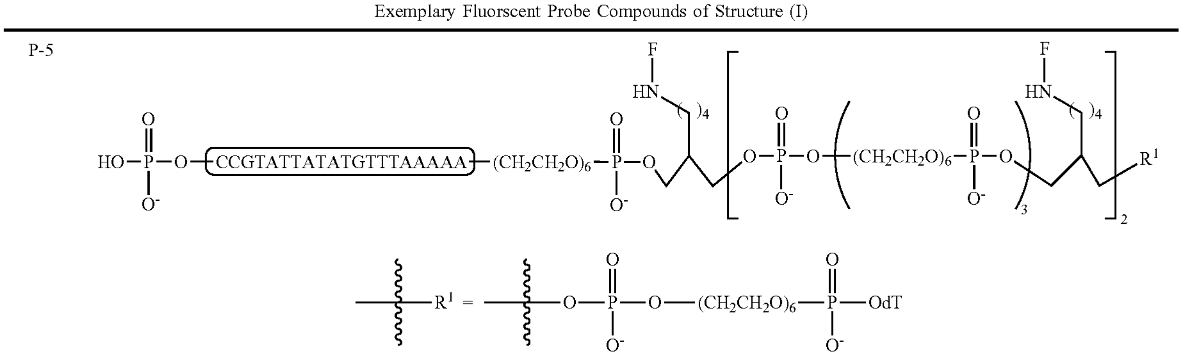
(SEQ ID NO: 1)
P-6
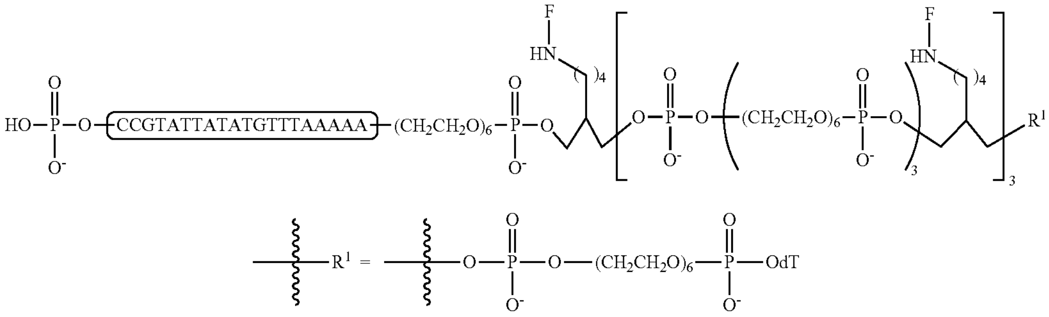
(SEQ ID NO: 1)
P-7
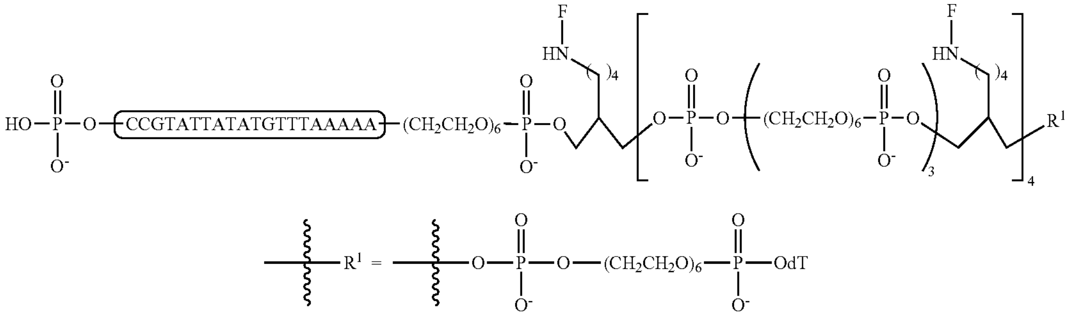
(SEQ ID NO: 1)
P-8
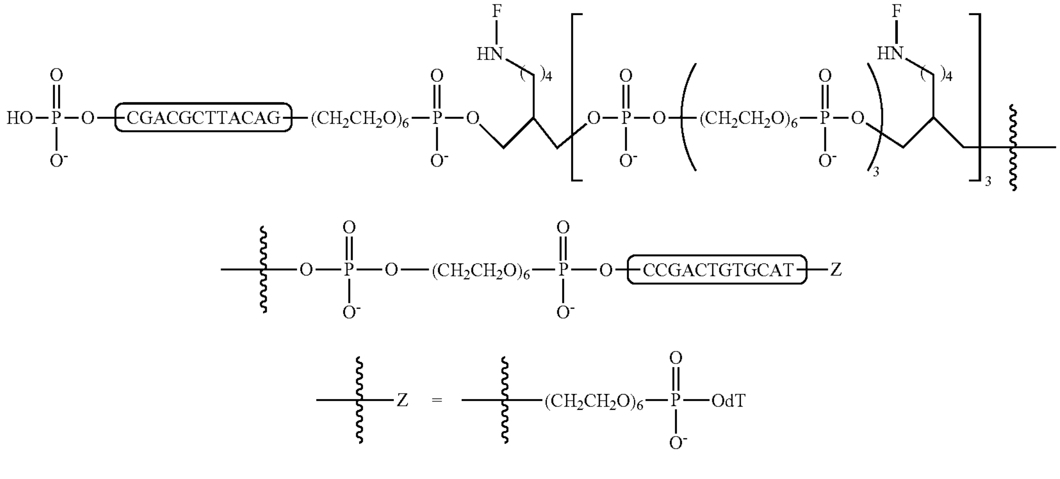
(SEQ ID NOS: 3 and 4)

TABLE 5
| Exemplary Quencher Probe Compounds of Structure (I) | |
|---|---|
| No. | Structure |
| Q-1 | 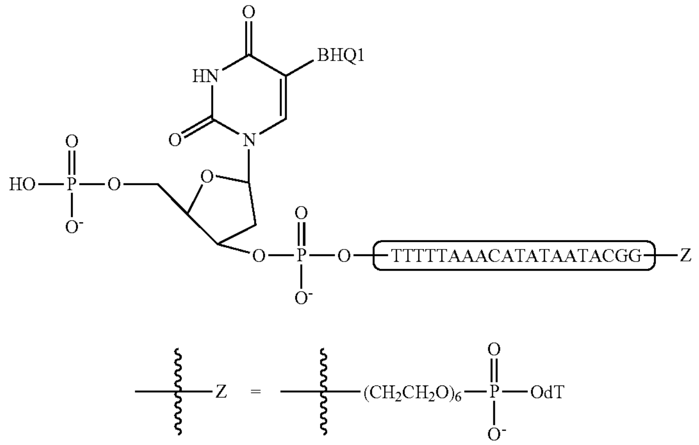 (SEQ ID NO: 2) |
| Q-2 | 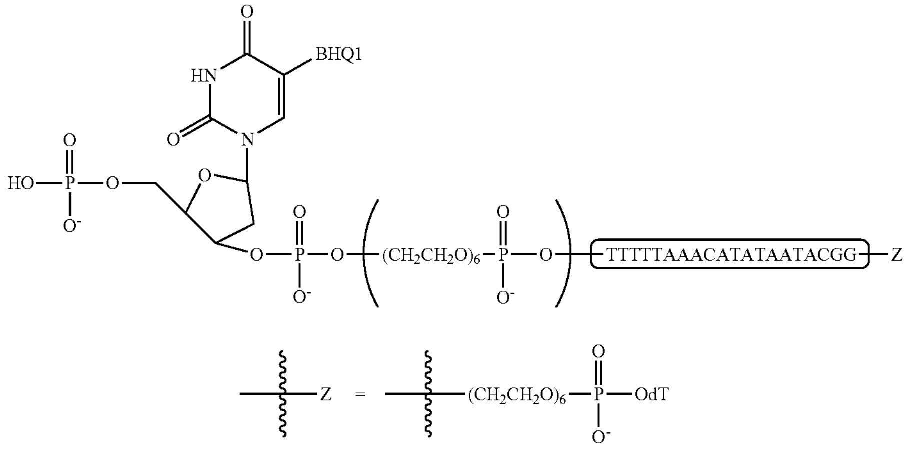 (SEQ ID NO: 2) |
| Q-3 | 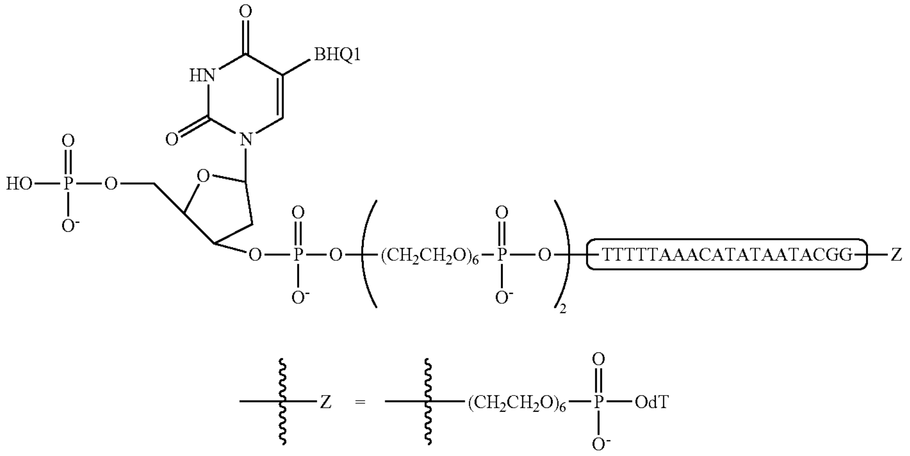 (SEQ ID NO: 2) |

TABLE 5-continued
| Exemplary Quencher Probe Compounds of Structure (I) | |
|---|---|
| No. | Structure |
| Q-4 | 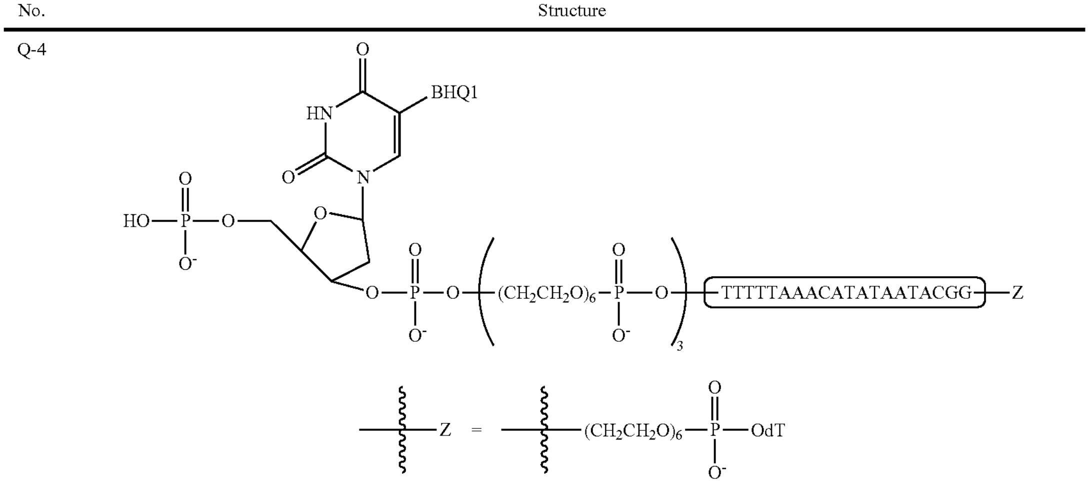 (SEQ ID NO: 2) |
| Q-5 | 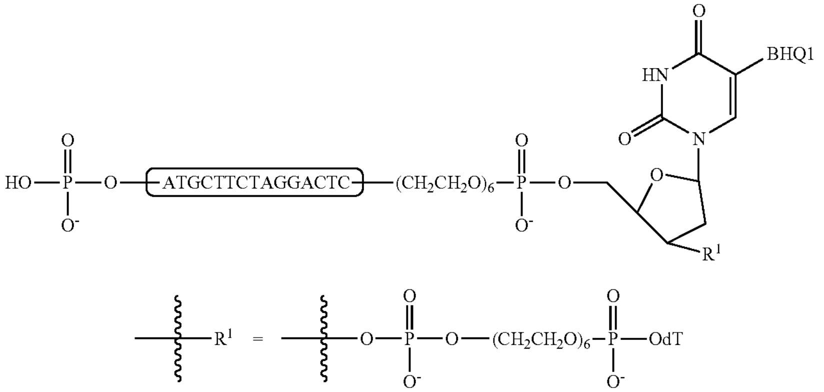 (SEQ ID NO: 5) |
| Q-6 | 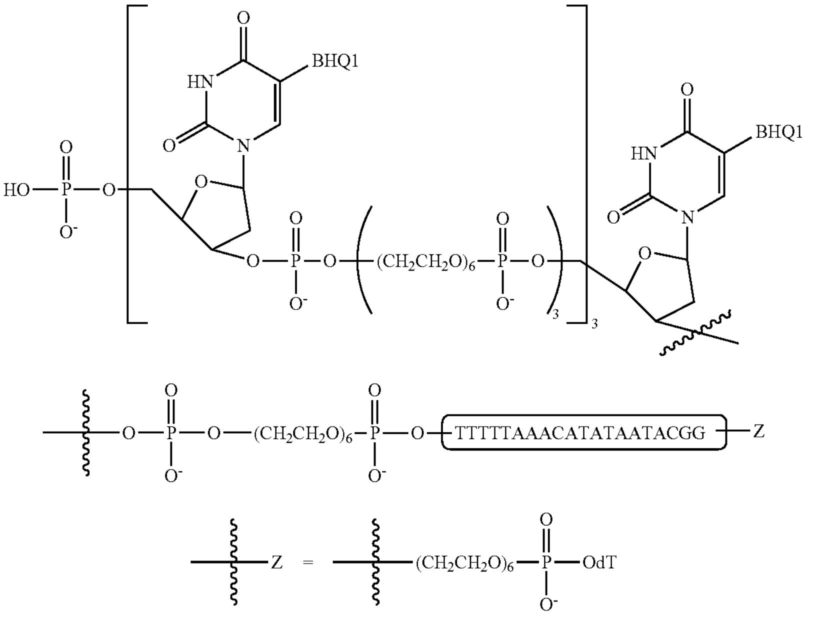 (SEQ ID NO: 2) |

TABLE 5-continued

Exemplary Quencher Probe Compounds of Structure (I)

| No. | Structure |
| --- | --- |
| Q-7 | 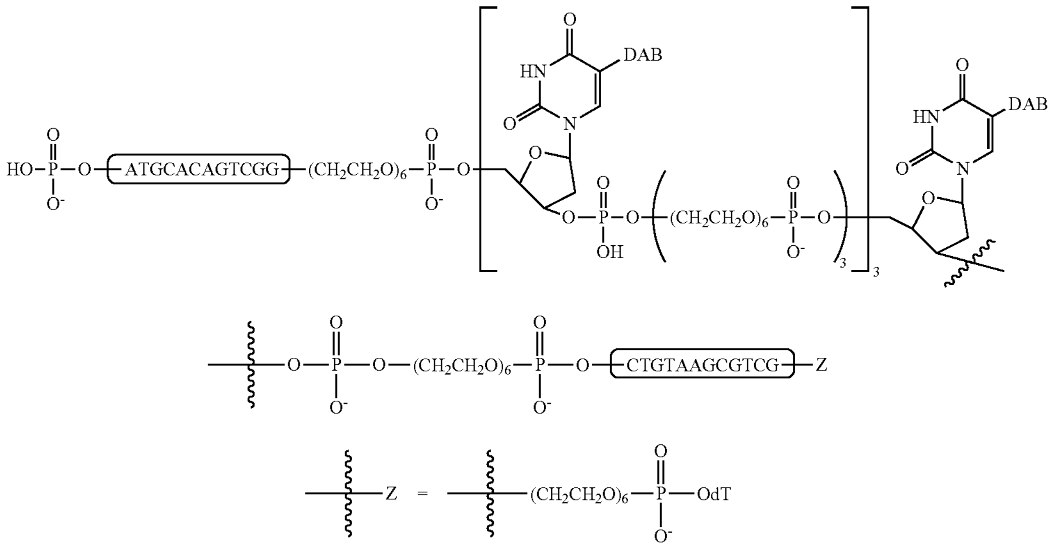 (SEQ ID NOS: 6) |

As used in Tables 3, 4 and 5 and throughout the application $R^2$, $R^3$, m, n and L' have the definitions provided for compounds of structure (I) unless otherwise indicated, and F, refers to a fluorescein moiety having the structure shown in Table 1 and BHQ1 and DAB refer to a quencher moieties having the structures shown in Table 2

"dT" refers to the following structure:

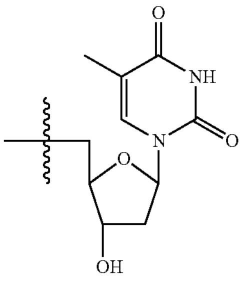

dT

EXAMPLES

General Methods

Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HFIP), 8.6 mM triethylamine (TEA), pH 8. Phosphoramidites and precursor molecules were also analyzed using a Waters Acquity UHPLC system with a 2.1 mm×50 mm Acquity BEH-C18 column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, VA). Anhydrous pyridine, toluene, dichloromethane, diisopropylethyl amine, triethylamine, acetic acid, pyridine, and THE were purchased from Aldrich. All other chemicals were purchased from Aldrich or TCI and were used as is with no additional purification.

Example 1

Synthesis of Dyes with Ethylene Glycol Spacer

Compounds with ethylene oxide linkers were prepared as followed:

The oligofluoroside constructs (e.g., compounds of structure (I), (II), or (III)) were synthesized on an Applied Biosystems 394 DNA/RNA synthesizer on 1 μmol scale and possessed a 3'-phosphate group or 3'-$S_2$—$(CH_2)_6$—OH group or any of the other groups described herein. Synthesis was performed directly on CPG beads or on Polystyrene solid support using standard phopshoporamadite chemistry. The oligofluorosides were synthesized in the 3' to 5' direction using standard solid phase DNA methods, and coupling employed standard β-cyanoethyl phosphoramidite chemistry. Fluoroside and nucleoside phosphoramidites and spacers (e.g., hexaethyloxy-glycol phosphoramidite, triethyloxy-glycol phosphoramidite, polyethylene glycol phosphoramidite) and linkers (e.g., 5'-amino-Modifier Phosphoramidite and thiol-Modifiers S2 Phosphoramidite) were dissolved in acetonitrile to make 0.1 M solutions, and were added in successive order using the following synthesis cycle: 1) removal of the 5'-dimethoxytrityl protecting group with dichloroacetic acid in dichloromethane, 2) coupling of the next phosphoramidite with activator reagent in acetonitrile, 3) oxidation of P(III) to form stable P(v) with iodine/pyridine/water, and 4) capping of any unreacted 5'-hydroxyl groups with acetic anhydride/1-methylimidizole/acetonitrile. The synthesis cycle was repeated until the full length oligofluoroside construct was assembled. At the end of the chain assembly, the monomethoxytrityl (MMT) group or dimethoxytrityl (DMT) group was removed with dichloroacetic acid in dichloromethane.

The compounds were provided on controlled-pore glass (CPG) support at 0.2 umol scale in a labeled Eppendorf tube. 400 μL of 20-30% $NH_4OH$ was added and mixed gently. Open tubes were placed at 55° C. for ~5 minutes or until excess gases had been liberated, and then were closed tightly and incubated for 2 hrs (+/−15 min.). Tubes were removed from the heat block and allowed to reach room temperature, followed by centrifugation at 13,400 RPM for 30 seconds to consolidate the supernatant and solids. Supernatant was carefully removed and placed into a labeled tube, and then 150 μL acetonitrile was added to wash the support. After the wash was added to the tubes they were placed into a CentriVap apparatus at 40° C. until dried.

The products are characterized by ESI-MS, UV-absorbance, and fluorescence spectroscopy.

Example 2

Spectral Testing of Compounds

Dried compounds were reconstituted in 150 μL of 0.1M $Na_2CO_3$ buffer to make a ~1 mM stock. The concentrated stock was diluted 50× in 0.1×PBS and analyzed on a NanoDrop UV spectrometer to get an absorbance reading. Absorbance readings were used along with the extinction coefficient (75,000 $M^{-1}$ $cm^{-1}$ for each FAM unit) and Beer's Law to determine an actual concentration of the stock.

From the calculated stock concentrations, ~4 mL of a 5 μM solution was made in 0.1M $Na_2CO_3$ (pH 9) and analyzed in a 1×1 cm quartz cuvette on a Cary 60 UV spectrometer, using a spectral range of 300 nm to 700 nm, to gauge overall absorbance relative to the group. From these 5 μM solutions, a second dilution was made at either 50 nM or 25 nM (also in 0.1M $Na_2CO_3$, pH 9) for spectral analysis on a Cary Eclipse Fluorimeter. Excitation was set at 494 nm and emission spectra were collected from 499 to 700 nm.

Example 3

Melt Curve Analysis of Probes in the Presence of a Quench Construct with a Complementary Oligomer Sequence Probe compounds P-1 and P-3 containing a 20-mer oligonucleotide sequence were synthesized according the methods described herein in Example 1. Probes P-1 and P-3 include one or two fluorescein moieties respectively. P-1 and P-3 were prepared in solution at a concentration of 2 μM and incubated in the presence or absence of the quenching construct, Q-4, containing a complementary 20-mer oligonucleotide sequence and a single BHQ-1 moiety. In tests where complementary probe and quencher compounds were mixed, the complementary oligonucleotides align, forming a hybrid complex. Samples were incubated for 10 minutes at ambient temperature and then analyzed using a CFX-96 thermal cycler to produce a melt curve.

Figure 2:
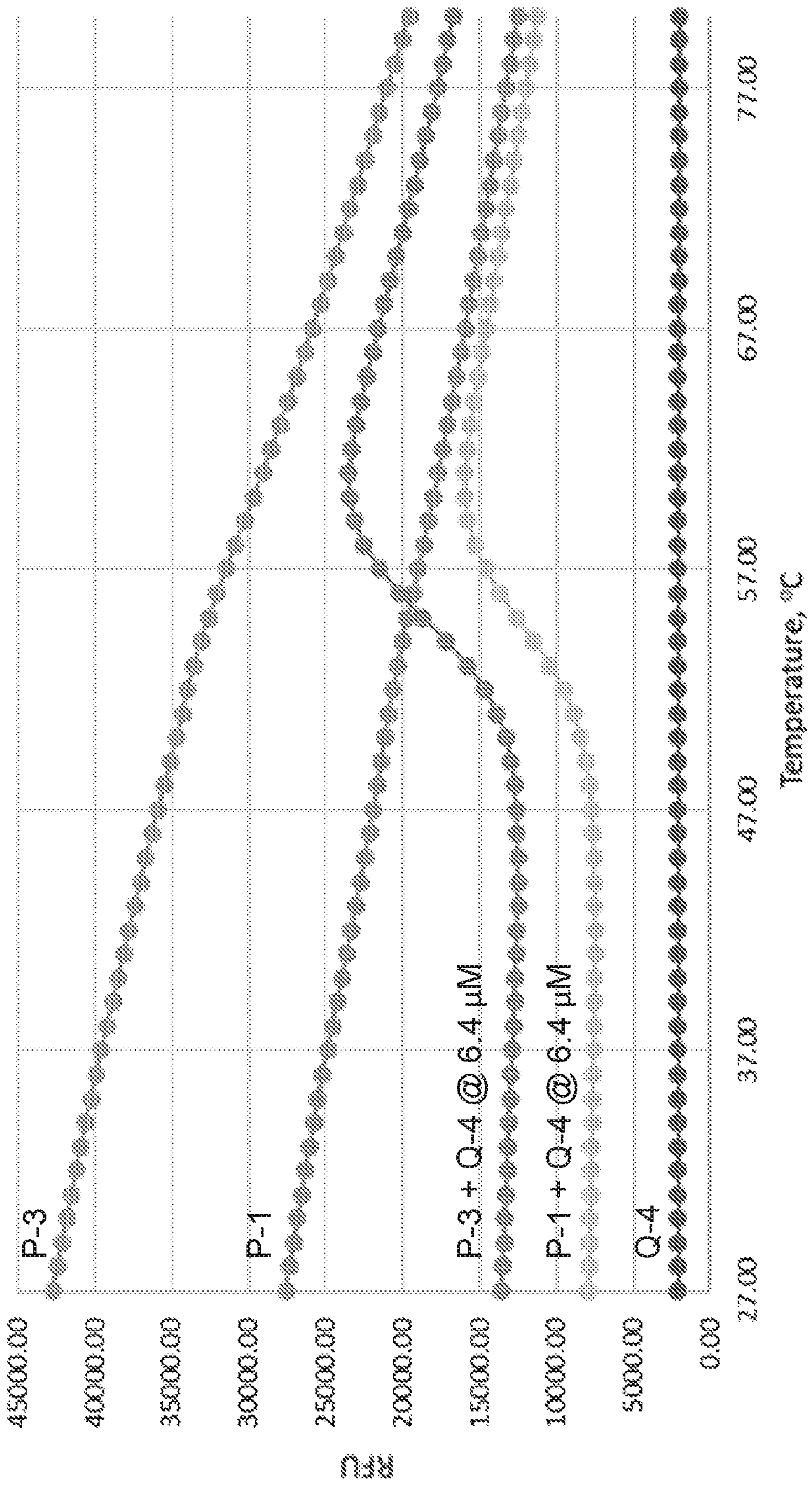
FIG. 2 depicts a melt curve plot for specific embodiments, including individual fluorescent probes and probe hybrid complexes, wherein the probes have complimentary sequences and the quencher probe has a concentration of 6.4 μM.
Figure 3:
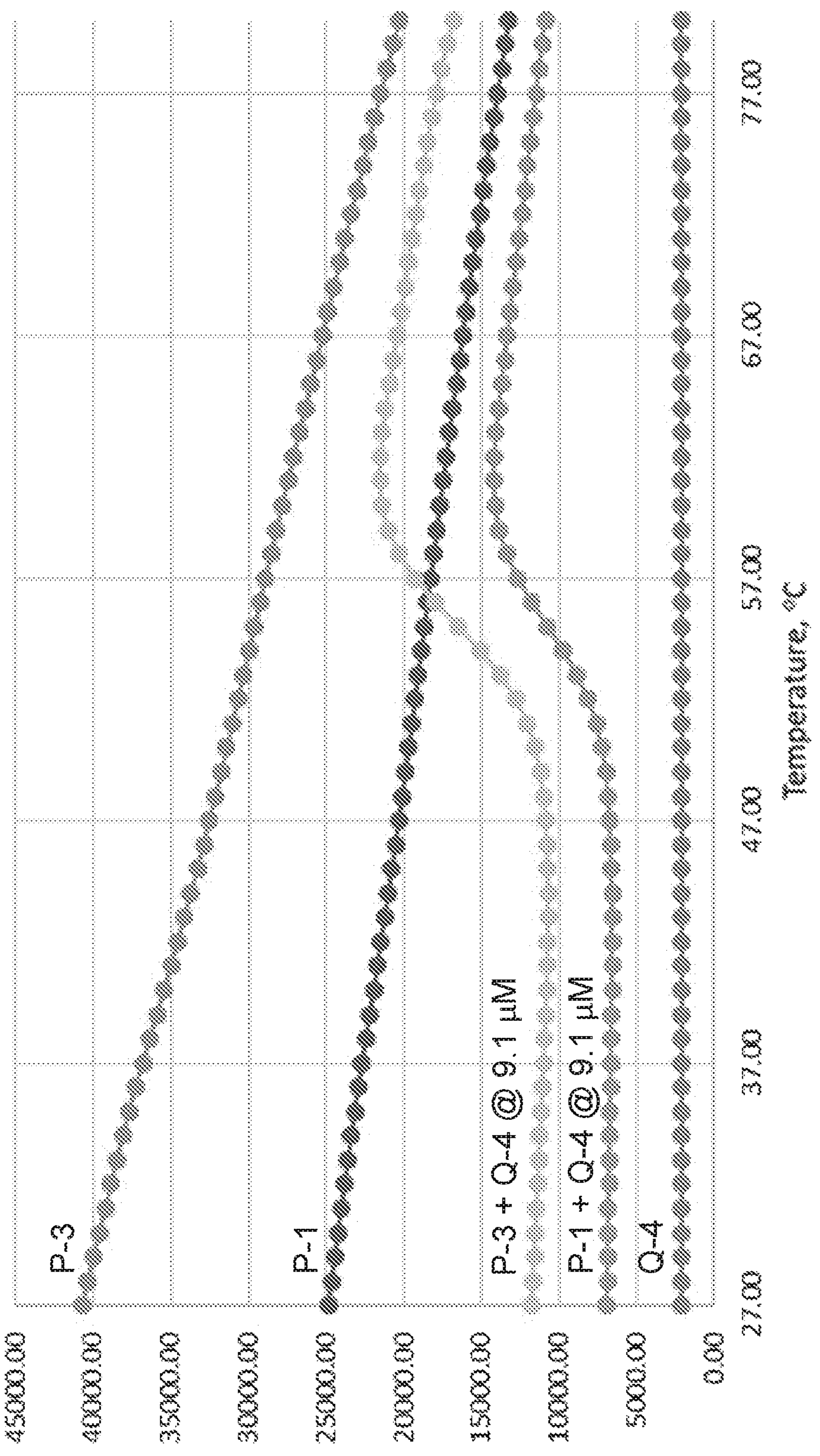
FIG. 3 depicts a melt curve plot for specific embodiments, including individual fluorescent probes and probe hybrid complexes wherein the probes have complimentary sequences and the quencher construct has a concentration of 9.1 μM.

FIGS. 2 and 3 show melt curves for probes P-1 and P-3 using quencher concentrations of Q-4 at 6.4 μM (FIG. 2) or 9.1 μM (FIG. 3). A reduction of fluorescence is observed for probe/quencher mixtures relative to those samples that include probe only, see initial fluorescence at 27° C. Compound P-3, with two fluorescein moieties demonstrated an approximate 1.6 fold increase in fluorescence over P-1 containing a single fluorescein moiety. Denaturing of the hybrid complex can be observed beginning at about 50° C. with the increase in fluorescence with increasing temperature. The increase in fluorescence results from denaturing because the quencher moiety demonstrates increased average distance away from the fluorophore, minimizing efficiency.

The results also demonstrate a strong temperature dependence on the observed fluorescence for probes in the absence of quencher as a result dynamic quenching of the fluorescence by temperature related mobility changes of groups within the compounds.

Example 4

Melt Curve Analysis of a Probe in the Presence of a Quench Construct with an Identical, Non-Complementary Oligomer Sequence As a negative control experiment, probe and quencher compounds with non-complementary oligonucleotide sequences were incubated together to demonstrate a lack of hybrid formation, and a resultant absence of significant quenching.

Probe compound P-2 containing a 20-mer oligonucleotide sequence was synthesized according the methods described herein in Example 1 and includes a single fluorescein moiety. P-2 was prepared in solution at a concentration of 2 μM and incubated in the presence or absence of the quenching construct, Q-4 (6 μM), containing an identical, non-complementary 20-mer oligonucleotide sequence. Consequently, in the mixed sample analysis, formation of a hybrid complex should not occur and an increase in fluorescence as a result of the denaturing of the hybrid complex, also should not occur. Samples were incubated for 10 minutes at ambient temperature and then analyzed using a CFX-96 thermal cycler to produce a melt curve at an initial temperature of 27° C. ramping to a final temperature of 80° C.

Figure 4:
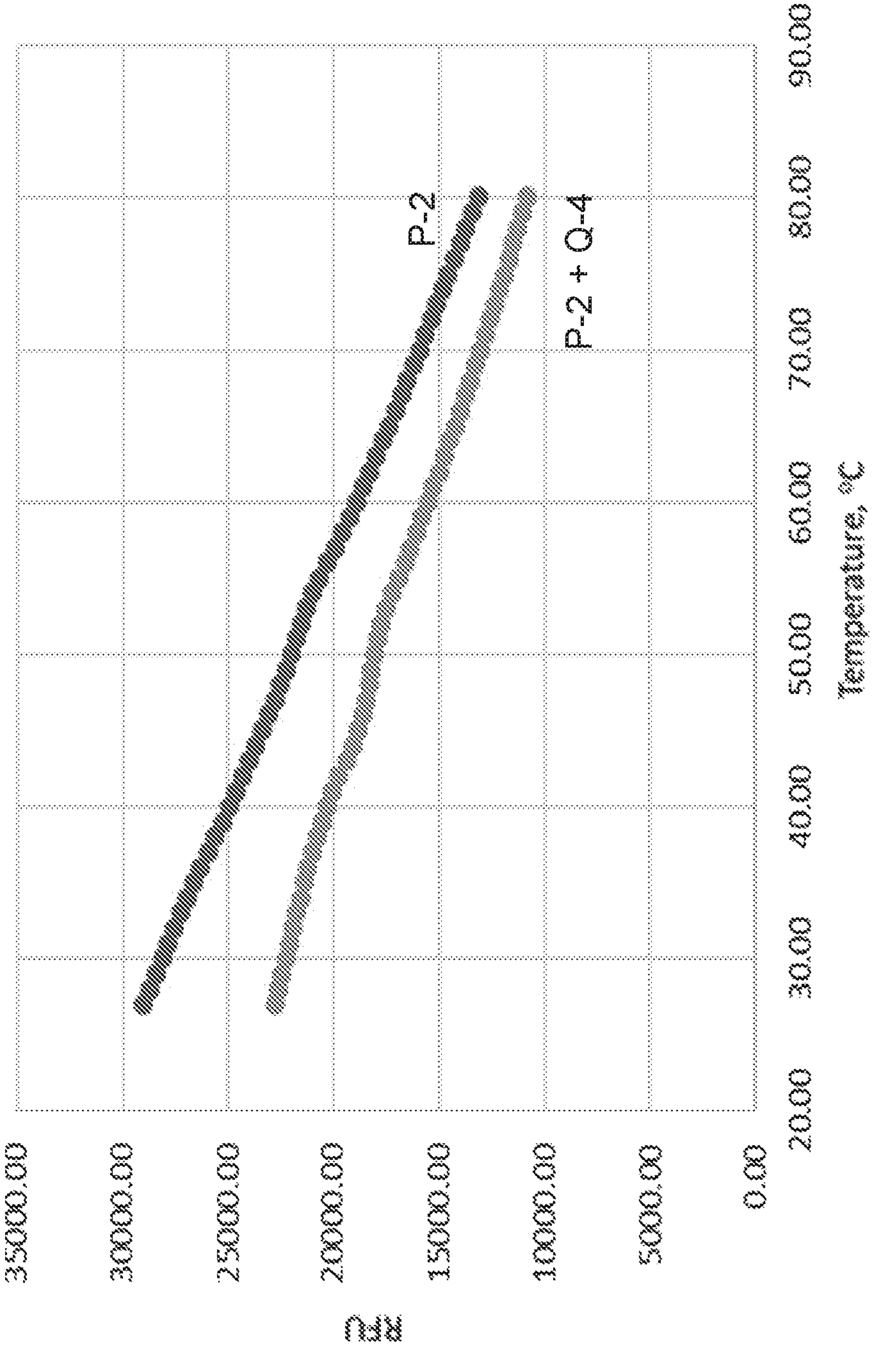
FIG. 4 shows a melt curve plot for specific embodiments, including individual fluorescent probes and probe hybrid complexes wherein the probes have non-complimentary sequences.

The melt curve analysis depicted in FIG. 4 shows the absence of an increase in fluorescence for the P-2/Q-4 mixture, demonstrating the lack of quantifiable hybrid formation, as a result of the identical, non-complementary oligonucleotide sequences. While a reduction of fluorescence was observed in the P-2/Q-4 mixture relative to the P-2 only analysis, this is attributed to intermolecular quenching.

Example 5

Determination of Relative Quenching Efficiency for Probes in the Presence of Quench Construct An analysis of the fluorescence data generated from Example 3 and Example 4 was performed to determine the relative quenching efficiency throughout the melt curve analysis experiment so that the change in fluorescence observed from the increasing temperature could be eliminated giving an easier to interpret curve.

Figure 5:
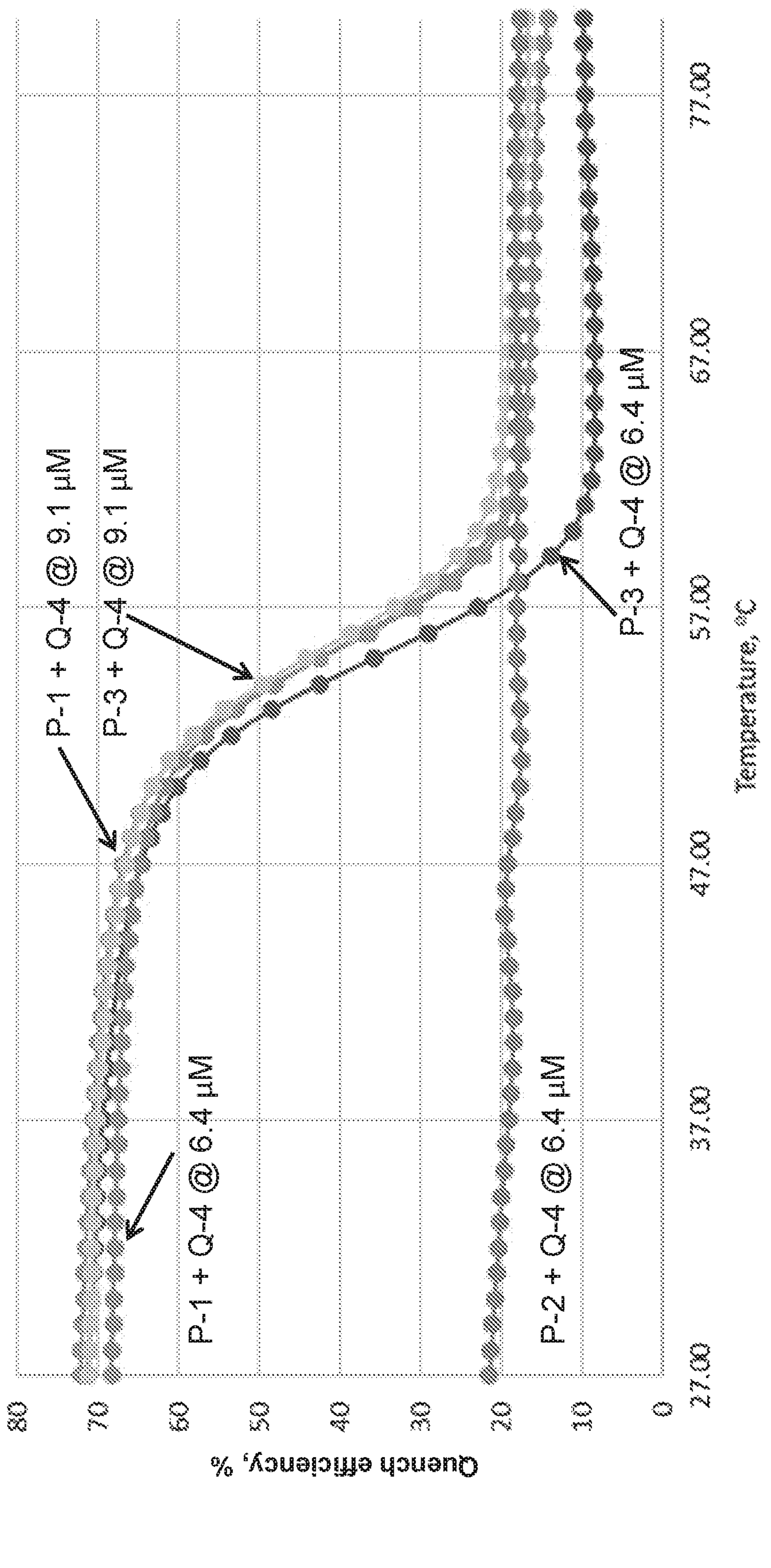
FIG. 5 plots quench efficiency data for probe hybrid complexes during melt curve analysis as a function of temperature.

FIG. 5 shows the relative quenching efficiency as a function of temperature for probe compounds P-1, P-2 and P-3 in the presence of quench probe Q-4. As expected, the data for P-2 in the presence of the non-complimentary quencher is essentially constant at 20%, since no denaturing results upon heating, and only non-hybrid complex, intermolecular quenching is observed. Interestingly, the relative quenching efficiency for P-1 and P-3 are similar despite the difference in fluorescein moiety number (1 and 2 respectively) and changes in the concentration of Q-4 (6.4 and 9.1 μM). It is noteworthy that Q-4, containing a single BHQ-1 moiety, had similar quenching efficiency for both P-1 and P-3 despite the difference in the number of fluorescein number.

Example 6

Determination of Fluorescence for Probes with Increasing Numbers of Fluorescein Moieties Probe compounds P-1, P-4, P-5, P-6 and P-7 containing a 20-mer oligonucleotide sequence and one, two, three, four, and five fluorescein (F) moieties, respectively, were synthesized according the methods described herein in Example 1. Fluorescence maxima were determined according to the methods described herein in Example 2. The results are tabulated in Table 6.

TABLE 6

Fluorescence of fluorescein probe dyes

| Cmpd. No. | F Moieties | Fluorescence | Relative Fluorescence to P-1 |
|---|---|---|---|
| P-1 | 1 | 8018.6 | 1 |
| P-4 | 2 | 8930.4 | 1.11 |
| P-5 | 3 | 10530.8 | 1.31 |
| P-6 | 4 | 12131.2 | 1.51 |
| P-7 | 5 | 13731.6 | 1.71 |

The results demonstrate the increase in fluorescence was not directly proportional to the number of fluorescein moieties; see for example Table 6 where the fluorescence for P-4 with two F moieties, did not show double the fluorescence relative to P-1 with one F moiety. Intra molecular quenching phenomena resulting from the increased length of the polymers as a result of additional fluorophore incorporation are contributing to the non-proportional increase in fluorescence.

Example 7

Quenching of Probes with Varying Fluorescein Moieties Using a Quench Probe Containing Four BHQ-1 Moieties, Including Melt Curve Analysis Probe compounds P-1, P-4, P-5, P-6 and P-7 containing a 20-mer oligonucleotide sequence and one, two, three, four, and five fluorescein moieties, respectively, were synthesized as previously described. Test compound solutions were prepared at a concentration of 0.5 μM according to the methods described herein in Example 2. Prior to analysis, samples were heated to 80° C. for two minutes, and then cooled to ambient temperature for five minutes. These test solutions were used for melt curve analysis of individual probe compounds, see below. Fluorescence maxima for individual probes P-1, P-4, P-5, P-6 and P-7 were determined from the initial measurement of the melt curve analysis.

Separate 0.5 μM solutions of test compounds were incubated for 10 minutes at ambient temperature with 1.0 μM quench probe, Q-6, which contains four BHQ-1 moieties. Prior to analysis, samples were heated to 80° C. for two minutes, and then cooled to ambient temperature for five minutes before performing melt curve analysis. Measurements of quenched fluorescence were determined from the initial measurement of the melt curve analysis.

Figure 6:
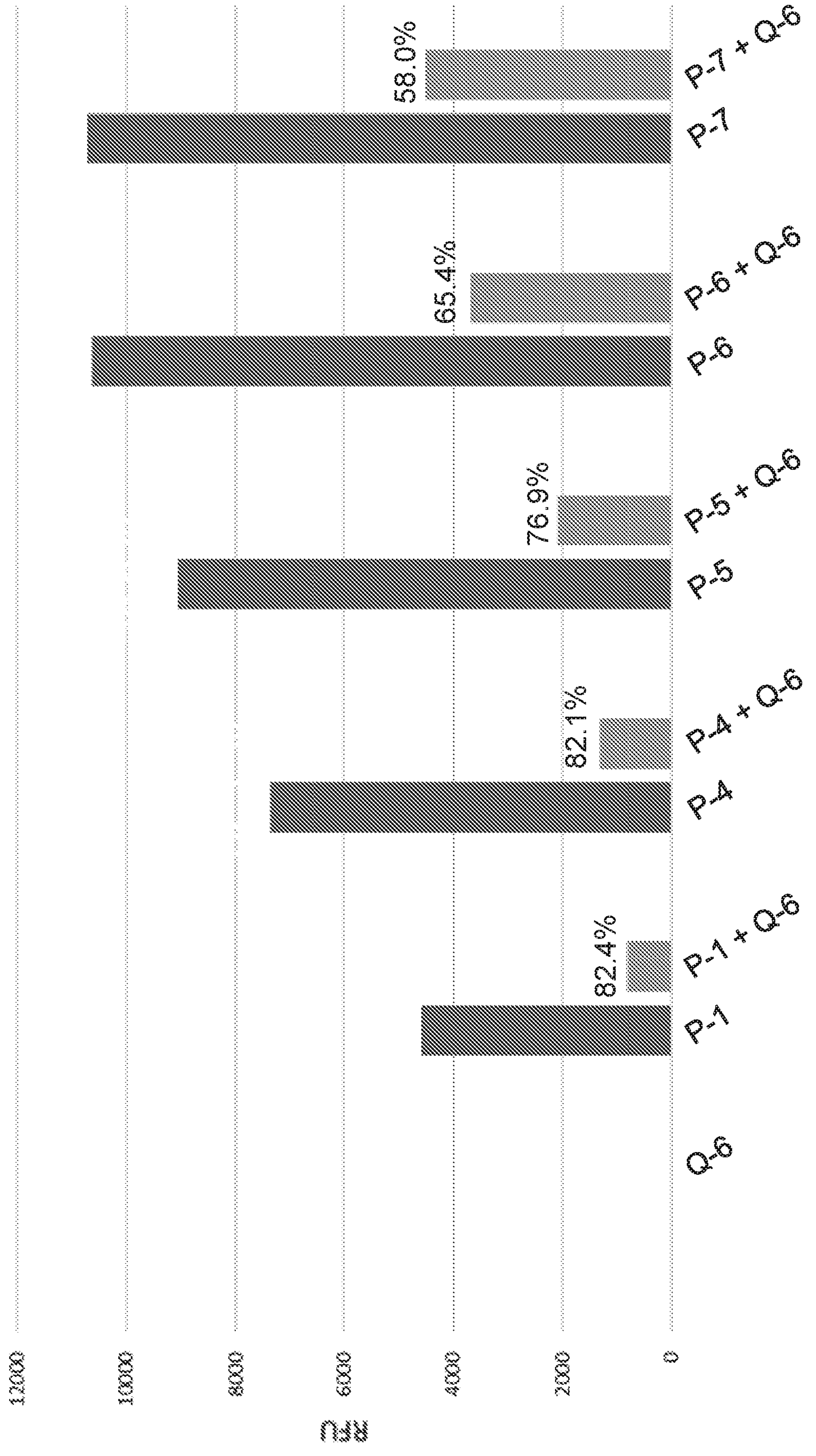
FIG. 6 depicts the relative fluorescence of individual fluorescent probe compounds containing increasing numbers of fluorescein moieties as 1) individual probes and 2) as hybrid complex formed with a complementary quencher construct.

FIG. 6 shows a bar chart of the fluorescence observed for compounds P-1, P-4, P-5, P-6 and P-7 in the absence (left bar) and presence (right bar) of quencher Q-6. Predictably, the quenching efficiency observed for Q-6 (BHQ-1 x4) decreased as the number of fluorescein (F) moieties in the probes increased, with the greatest quenching observed for mono-F compound P-1 (82.4%) and the lowest for penta-F compound P-7 (58.0%). Notably in this data, there was minimal increase in fluorescence when the fluorescein moieties increased in number from 4 to 5, suggesting that intramolecular quenching in this compound series may limit total brightness once compounds reach a certain length.

Figure 7:
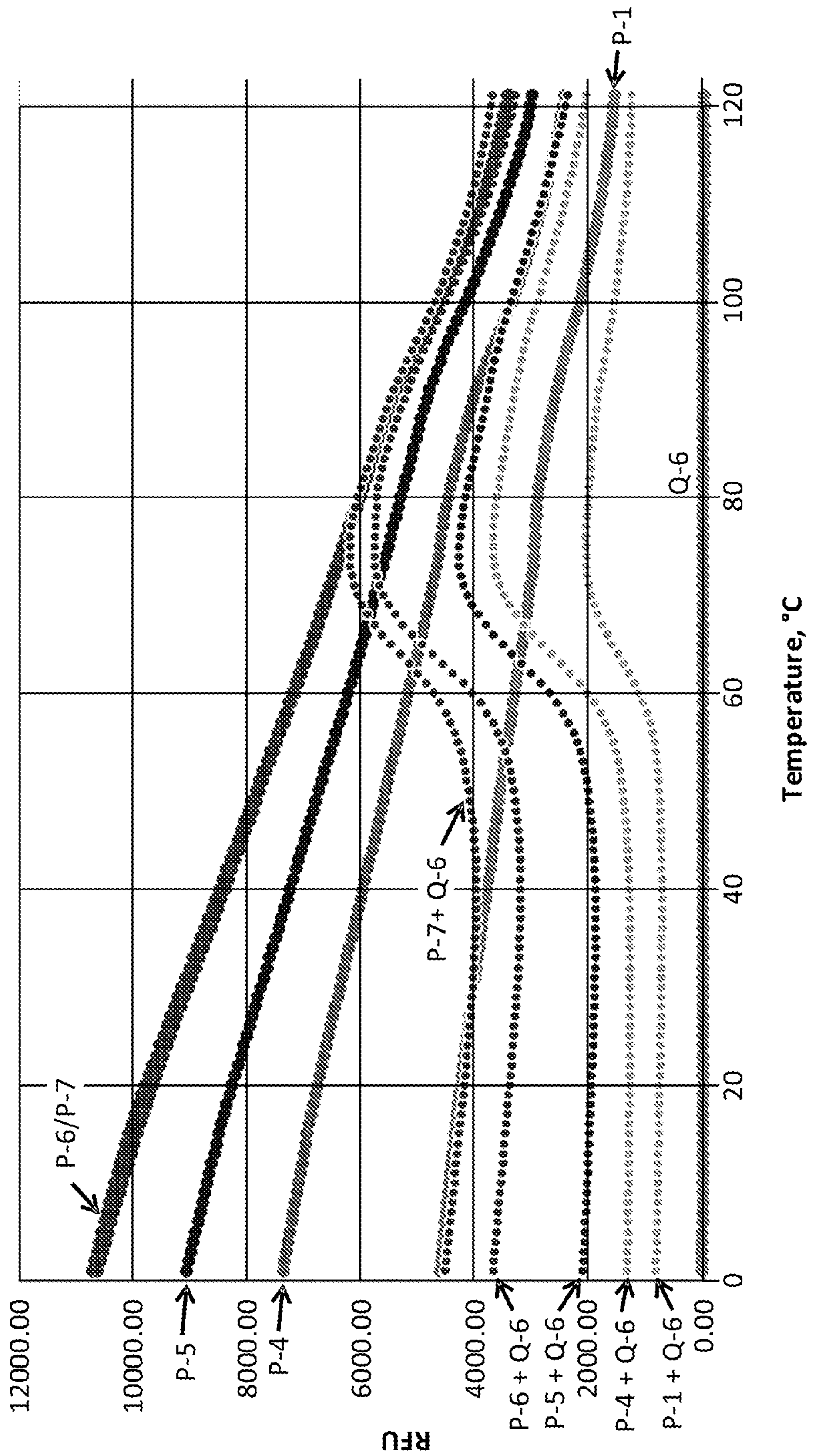
FIG. 7 depicts a melt curve plot for specific embodiments, including individual fluorescent probe compounds containing increasing numbers of fluorescein moieties as 1) individual probes and 2) as hybrid complex formed with a complementary quencher construct.

Melt curve analysis of the above prepared samples was performed using a CFX-96 thermal cycler at an initial temperature of 0° C. ramping to a final temperature of 122° C. FIG. 7 shows the melt curve analysis for all test samples. Consistent with the results of Example 3, test compounds devoid of quencher probes displayed a strong temperature dependence on the observed fluorescence. Furthermore, increases in the fluorescence observed for probe/quencher combinations is indicative of the hybrid complex denaturing. The start of that process is consistent across all test samples, occurring at approximately 50° C., suggesting some consistency in the nature of the hybrid complex. Once denatured, the fluorescence properties of combo test solutions mirror those of probe-only solutions.

Example 8

Demonstrating Probe and Quencher Hybridization Upon Cooling Using A Thermal Cycler Solutions of probe compounds P-1 and P-6 and probe P-8 were prepared and analyzed using a thermal cycler in cooling mode (warm to cool transition) in the presence of complementary quencher, Q-6 (4×BHQ-1 moieties) and quencher, Q-7 (4× Dab moieties) respectively. Quencher-free solutions of each probe compound were also prepared and analyzed in the same manner. P-1 contains one fluorescein moiety; P-6 and P-8 each contain four.

Test solutions were heated to 80° C. in a CFX-96 thermal cycler, held for two minutes, then cooled to 25° C. (−5° C./cycle, hold 4 seconds).

Figure 8:
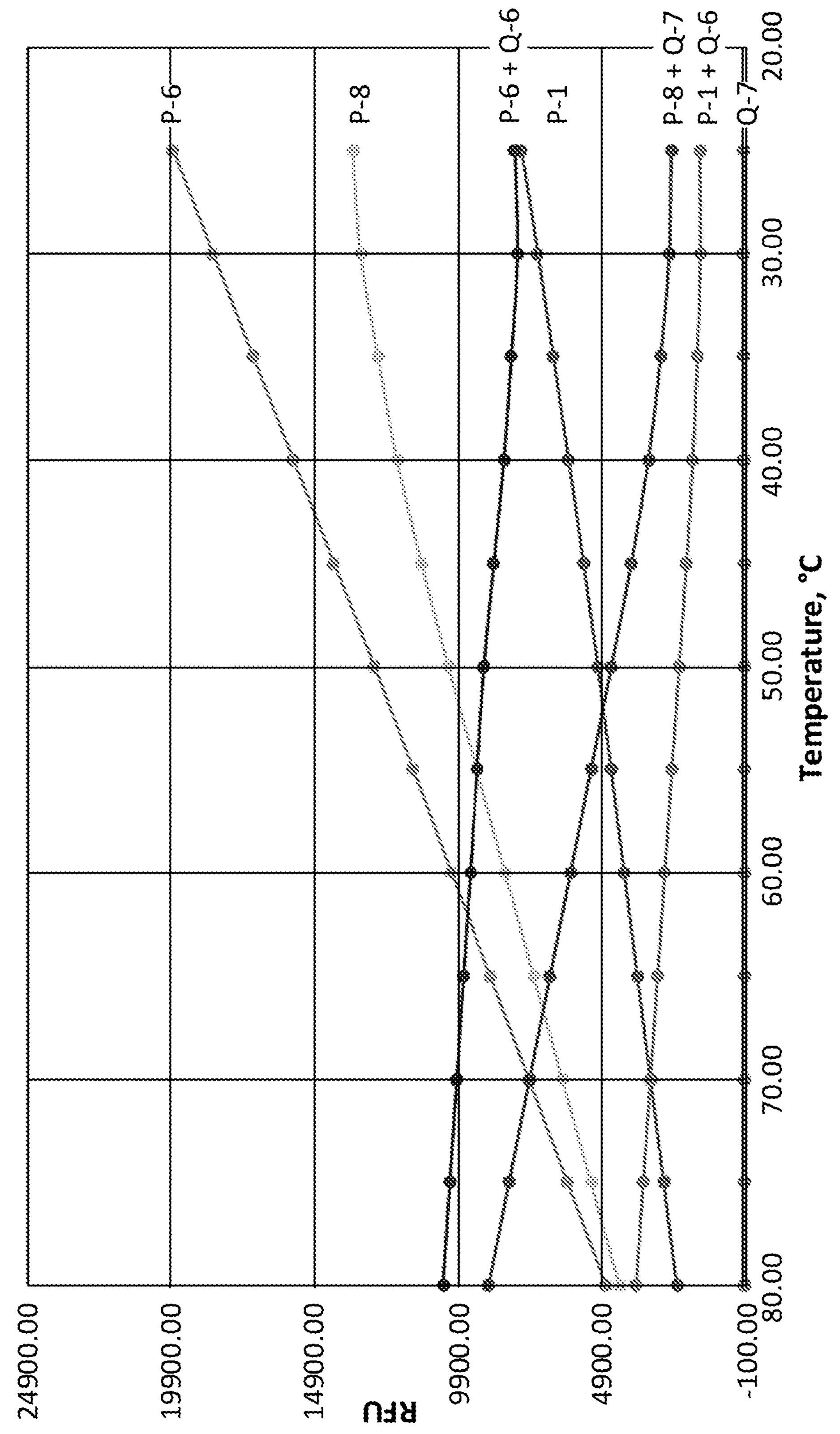
FIG. 8 shows evidence of probe/quencher hybridization upon cooling using a thermal cycler.

Plots of probe compound fluorescence as a function of temperature are shown in FIG. 8. As expected in cooling mode, probe-only solutions demonstrated an increase in fluorescence as the temperature lowered; opposite the trend observed for melt curve analysis. Likewise, probe and quencher test samples demonstrated a reduction in fluorescence as the complementary oligonucleotides began to anneal and form hybrid complexes (as schematically shown in FIGS. 1A and 1C) respectively.

Without wishing to be bound by theory, Applicant believes the greater reduction in fluorescence relative to the initial state (80° C.) for the P-8/Q-7 hybrid, as compared to the P-6/Q-6 hybrid is the result of improved quenching capability, as a result of the quenching moieties being in closer proximity to the fluorophores, or superior hybridization efficiency, or a combination of both.

Example 9

Comparing Probe Pair Quenching Efficiency Relative to Probe Pairs

Probe compounds P-1, and P-6 and probe P-8 were synthesized as previously described. Test compound solutions were prepared at a concentration of 1.0 μM according to the methods described herein in Example 2. Prior to analysis, samples were heated to 80° C. for two minutes, and then cooled to ambient temperature for five minutes Subsequently, these test solutions were used for melt curve analysis of individual probe compounds, see below. Fluorescence maxima for individual probes P-1, P-6 and P-8 were determined from the initial measurement of the melt curve analysis. P-1 contains one fluorescein moiety; P-6 and P-8 each contain four.

Separate 1.0 μM solutions of test compounds were incubated for 10 minutes at ambient temperature with 1.9 μM quench probe, Q-6, for probes P-1 and P-6; and quencher Q-7 for probe P-8. Prior to analysis, samples were heated to 80° C. for two minutes, and then cooled to ambient temperature for five minutes before performing melt curve analysis. Measurements of quenched fluorescence were similarly determined from the initial measurement of the melt curve analysis.

Figure 9:
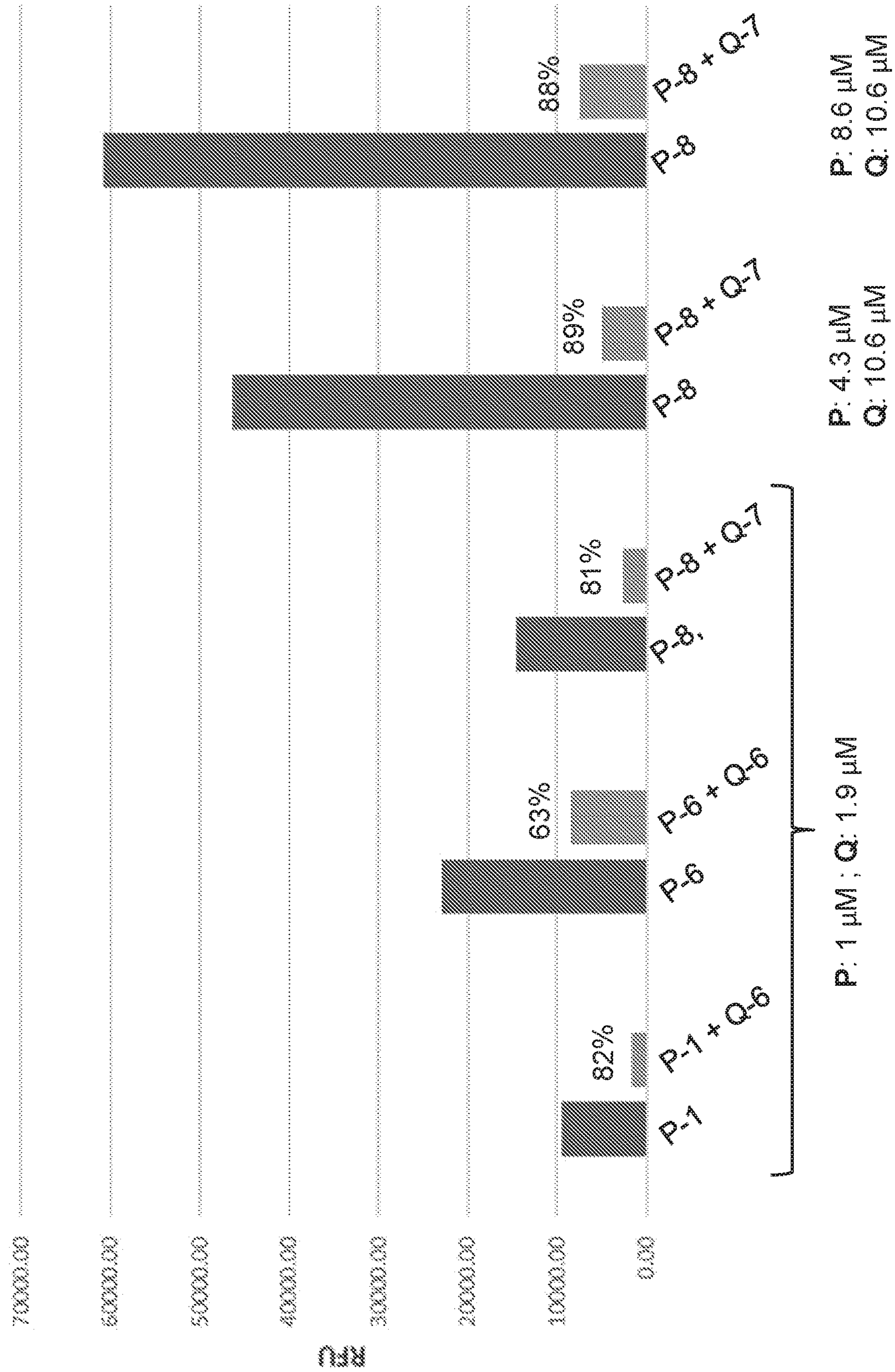
FIG. 9 depicts the quenching efficiency observed for hybrid complexes relative to analogous variants.

FIG. 9 shows a bar chart of the fluorescence observed for compounds P-1, P-6 and P-8 in the absence (left bar) and presence (right bar) of quencher Q6 or Q7 as indicated. Remarkably, the P-8/Q-7 pair demonstrated an 81% reduction in fluorescence, a value comparable to the P-1/Q-6 pair (82%) which has only a single fluorescein moiety on P-1 relative to the four quenching moieties on Q-6. By contrast, the P-8 probe contains four fluorescein moieties, equaling the number of quenching moieties on Q-7.

Additional test solutions for P-8/Q-7 were prepared to investigate the quenching efficiency at higher concentrations. Test solutions of P-8 were prepared at 4.3 and 8.6 μM and these were analyzed in an analogous manner to determine the fluorescence of the individual probe solutions. Likewise, separate solutions of test compounds were incubated for 10 minutes at ambient temperature with quench probe Q-7, this time at a concentration of 10.6 μM. These results are also presented in FIG. 9, and a summary of the data can be found in Table 7.

Notably in these data, there was observed a further increase in quenching at the higher probe concentrations (4.3 and 8.6 μM), reaching nearly 90%, with an even lower quencher/probe ratio, see last entry of Table 7.

TABLE 7

Comparison of probe hybrids

| Cmpd. (Q) | F Moieties | Fluorescence Probe | Fluorescence Probe + Q | Probe conc. (μM) | Q Conc. (μM) | Q: Probe | % Quench |
|---|---|---|---|---|---|---|---|
| P-1 (Q-6) | 1 | 9466.56 | 1662.05 | 1 | 1.9 | 1.9 | 82 |
| P-6 (Q-6) | 4 | 22914.22 | 8432.74 | 1 | 1.9 | 1.9 | 63 |
| P-8 (Q-7) | 4 | 14603.08 | 2709.77 | 1 | 1.9 | 1.9 | 81 |
| P-8 (Q-7) | 4 | 46403 | 4951 | 4.3 | 10.6 | 2.47 | 89 |
| P-8 (Q-7) | 4 | 60800 | 7493 | 8.6 | 10.6 | 1.23 | 88 |

By design, the probe and quencher pairs with polynucleotide sequences arranged on both sides of the fluorophores and quenchers are meant to force the one or more fluorophores of the quencher probe into closer proximity with the quencher moieties of the complementary quencher polymer through hybridization occurring on either side of the fluorescent and quenching moieties; see FIG. 1C. Without being bound to theory, Applicant believes the pair variants (see FIG. 1A) demonstrate reduced quenching efficiency as a result of increased distance between the fluorophore and quenching moieties, caused by electrostatic repulsion between the negatively charged, phosphate containing, polymer backbone. The probes overcome this deficiency through tandem hybridization on either side of the moieties thereby reducing the distance between the fluorophore and quencher and increasing efficiency.

Figure 10:
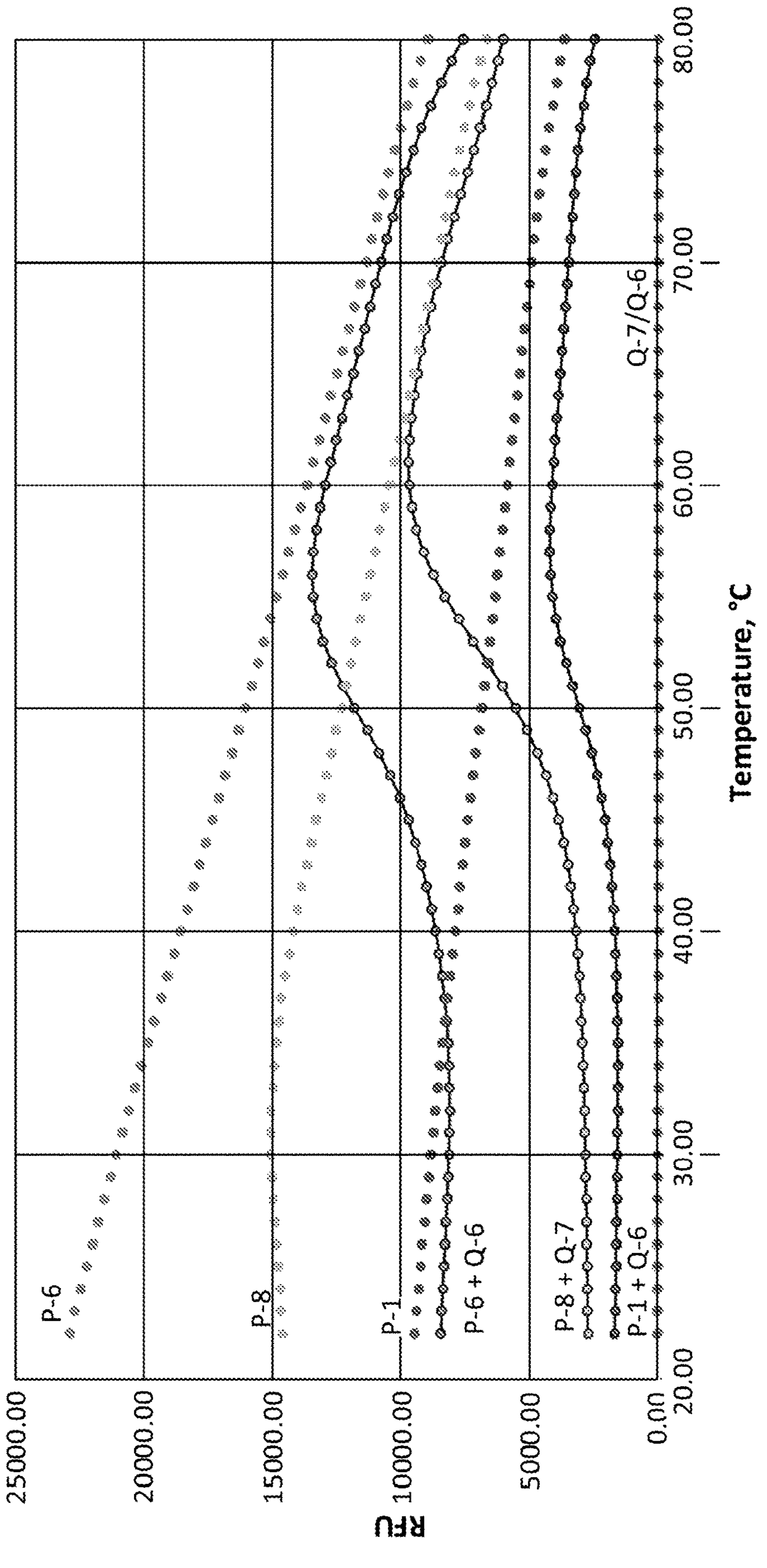
FIG. 10 shows a melt curve plot for specific embodiments, including 1) an individual fluorescent probe compound and 2) a hybrid complex formed with a complementary quencher construct.

Melt curve analysis of the above prepared, 1.0 μM samples was performed using a CFX-96 thermal cycler at an initial temperature of 22° C. ramping to a final temperature of 80° C. FIG. 10 shows the melt curve analysis for all test samples. Consistent with other melt curve results test compounds devoid of quencher probes displayed a strong temperature dependence on the observed fluorescence with a noted decrease as temperatures increased. Additionally, increases in the fluorescence observed for probe/quencher combinations is indicative of the hybrid complex denaturing.

Example 10

Quenching of Probes with Varying Fluorescein Moieties Using a Mono-Denta Quench Probe Containing a Single BHQ-1 Moiety Test solutions of probe compounds P-1, P-4, P-5, P-6 and P-7 were prepared as previously described in Example 2 and Example 7 at a nominal concentration of 0.5 μM. Prior to analysis, samples were heated to 80° C. for two minutes, and then cooled to ambient temperature for five minutes. Fluorescence maxima for individual probes P-1, P-4, P-5, P-6 and P-7 were determined on a CFX-96 thermal cycler at 22° C.

Separate 0.5 μM solutions of test compounds were incubated for 10 minutes at ambient temperature with 1.3 μM (2.6 eq) quench probe, Q-4, which contains one BHQ-1 moiety. Prior to analysis, samples were heated to 80° C. for two minutes, and then cooled to ambient temperature for five minutes. Measurements of quenched fluorescence were determined on a CFX-96 thermal cycler at 22° C.

Figure 11:
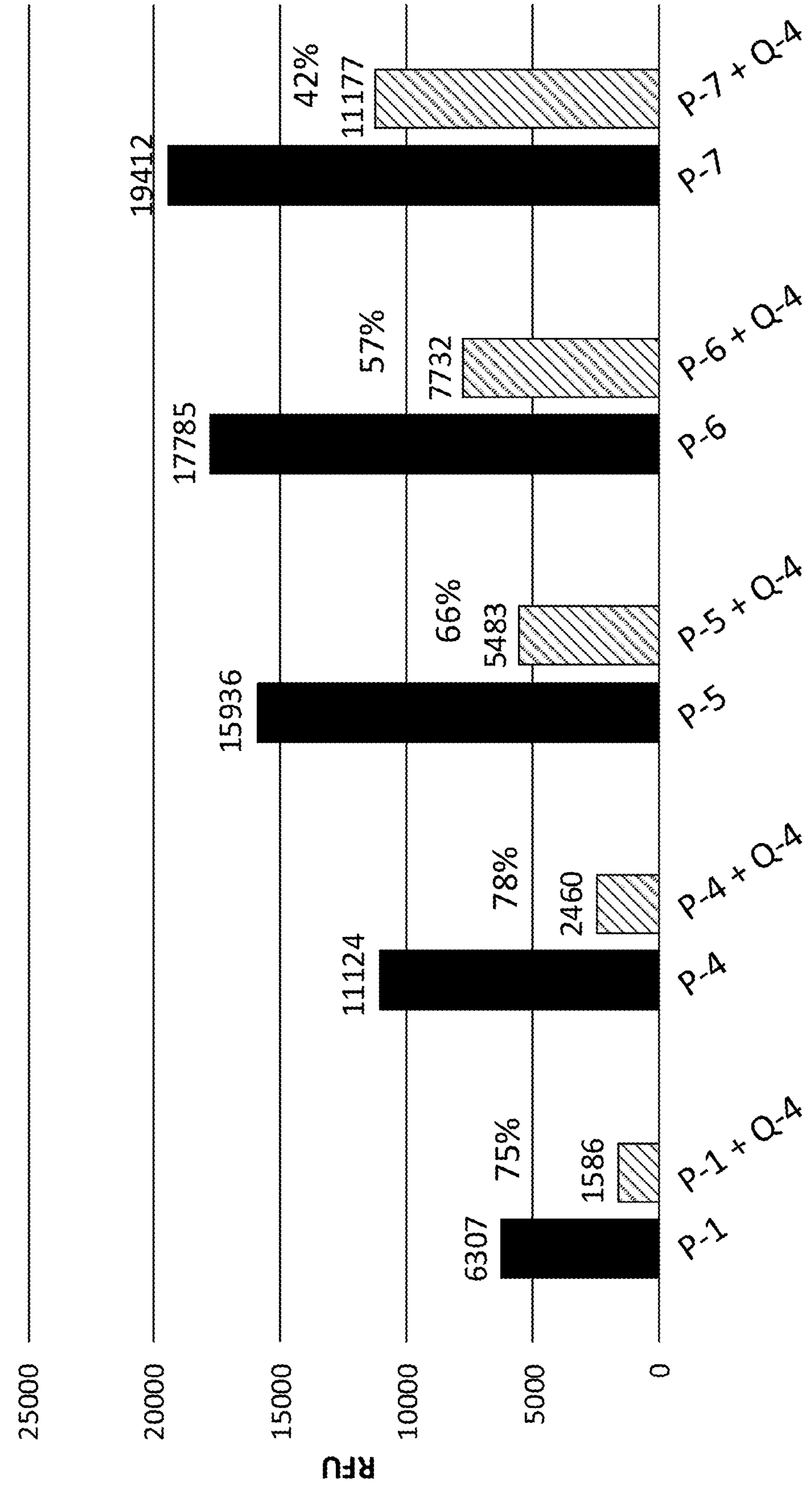
FIG. 11 illustrates the quenching efficiency of hybrid complexes formed from individual probes containing increasing numbers of fluorescein moieties, and a complementary quencher constructs with a single BHQ-1 moiety.

FIG. 11 shows a bar chart of the fluorescence observed for compounds P-1, P-4, P-5, P-6 and P-7 in the absence (left bar) and presence (right bar) of quencher Q-4 Predictably, the quenching efficiency observed for probe/Q-4 pairs decreased as the number of fluorescein (F) moieties in the probes increased. However, the best quenching was observed for di-F compound P-4 (78%) with the mono-F P-1 nearly equivalent (75%). The penta-F compound P-7 showed the lowest quenching efficiency (42%).

Figure 12:
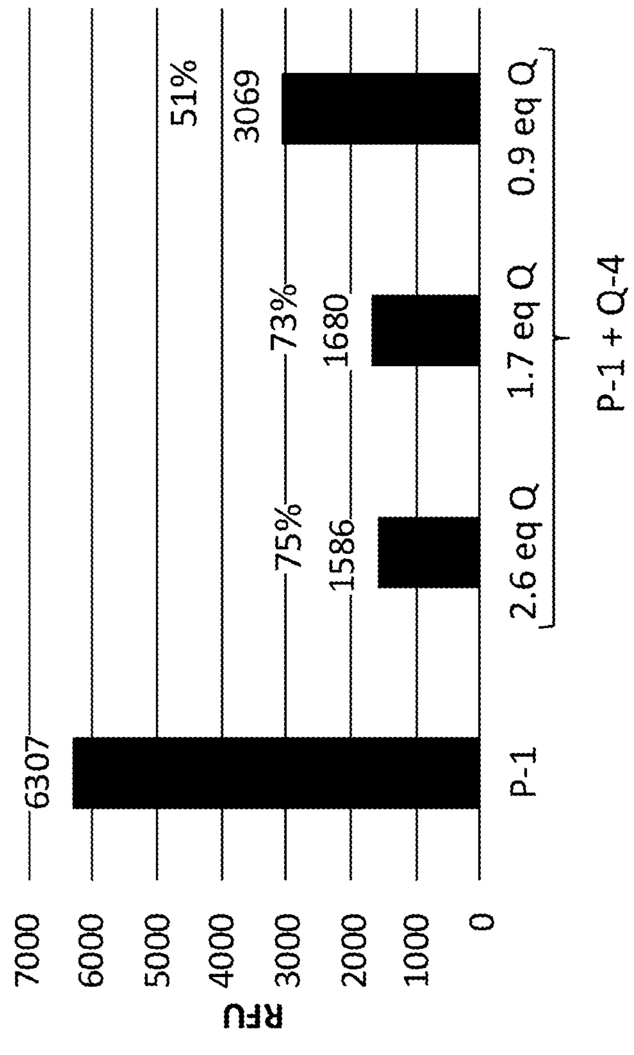
FIG. 12 illustrates the quenching efficiency of hybrid complexes containing one fluorescein moiety and one BHQ-1 moiety, at varying initial concentrations of quencher construct.

To investigate the effects of lower concentrations of quencher probe, Q-4, two additional tests were performed on solutions of P-1 with 0.85 μm and 0.45 uM of quencher probe, Q-4 (1.7 and 0.9 eq., respectively). FIG. 12 shows the results of this analysis, demonstrating that with less than 1 equivalent of quencher probe, fluorescent quenching can be approximately 50%, even with the less preferred mono-.

The various embodiments described above can be combined to provide further embodiments. All of the U.S.

patents, U.S. patent application publications, U.S. patent applications, foreign patents, foreign patent applications and non-patent publications referred to in this specification and/or listed in the Application Data Sheet, including U.S. Patent Application No. 62/908,509, filed Sep. 30, 2019, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the following structure (I):

(I)

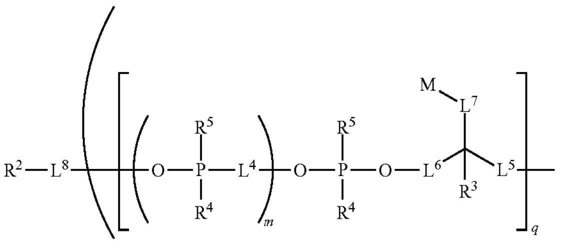

-continued

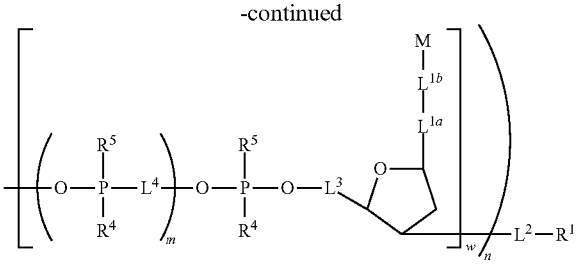

or a stereoisomer, salt or tautomer thereof, wherein:

M is, at each occurrence, independently either: a) the same or different fluorophore; or b) the same or different fluorophore quencher;

$L^{1a}$ is, at each occurrence, independently a heteroarylene linker;

$L^2$ and $L^8$ are independently linkers or absent;

$L^{1b}$, $L^3$, $L^5$, $L^6$ and $L^7$ are, at each occurrence, independently absent, or alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$R^1$ and $R^2$ each comprise a polynucleotide or —OP(=$R_a$)($R_b$)$R_c$, provided that at least one of $R^1$ and $R^2$ comprises a polynucleotide;

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

L' is, at each occurrence, independently a linker comprising a covalent bond to a solid support, a linker comprising a covalent bond to a solid support residue or a linker comprising a covalent bond to a nucleoside;

m is, at each occurrence, independently an integer of zero or greater;

n is an integer from 2 to 10; and q and w are, at each occurrence, independently 0 or 1, provided that at least one occurrence of either q or w is 1.

2. The compound of claim 1, wherein the compound has one of the following structures:

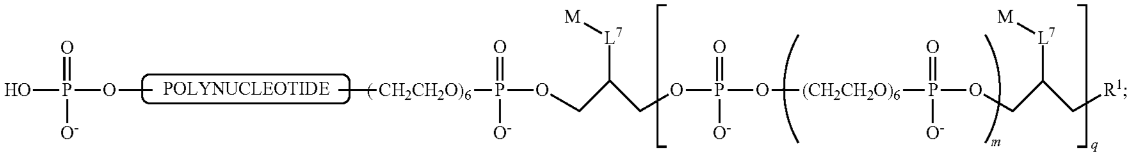

;

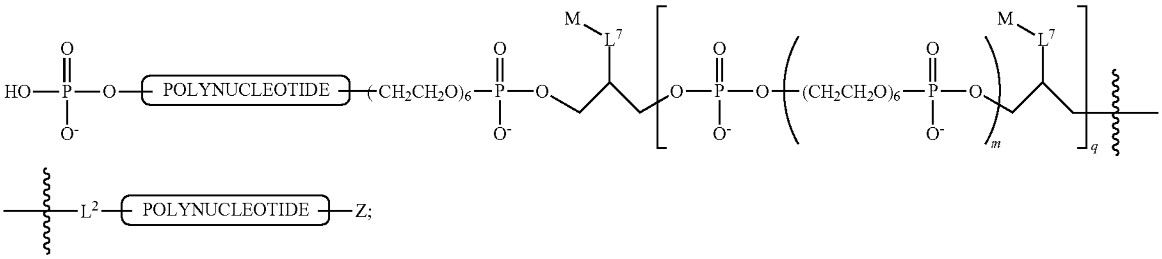

;

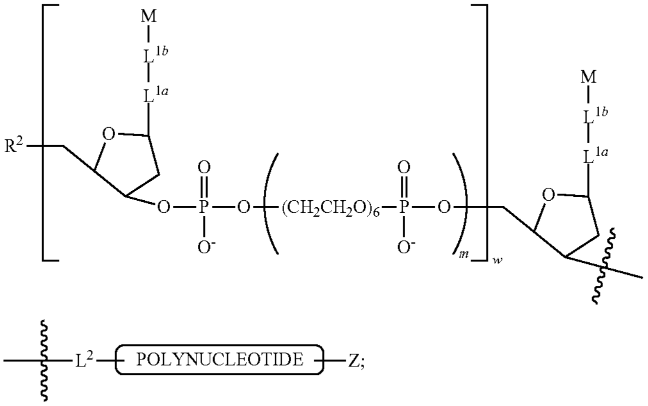

;

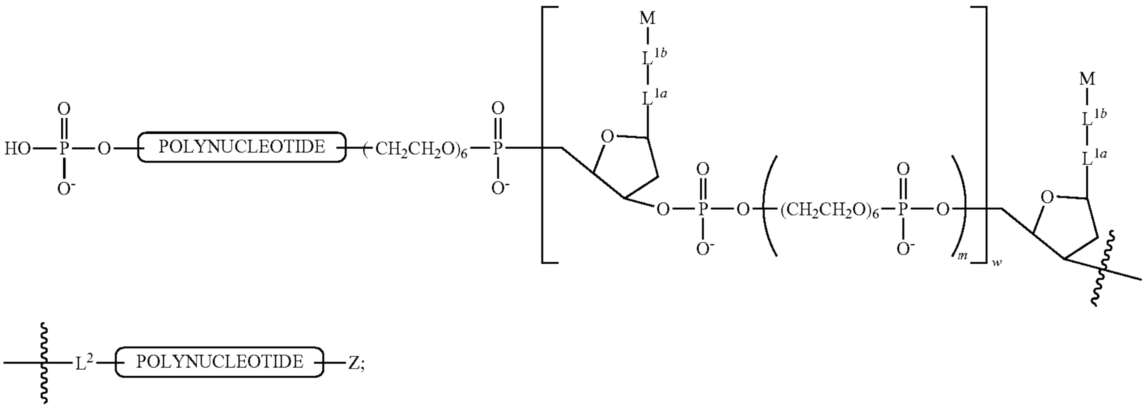

;

-continued
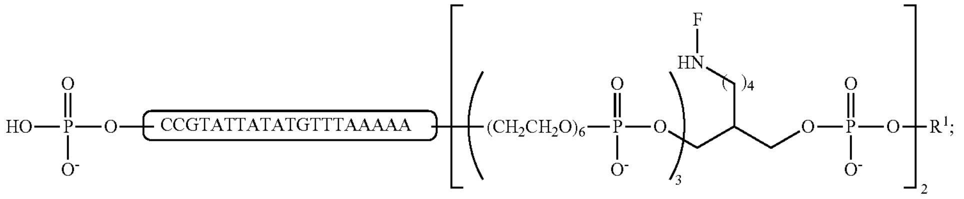
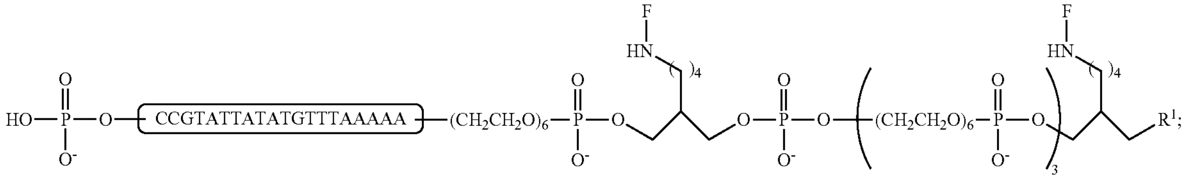
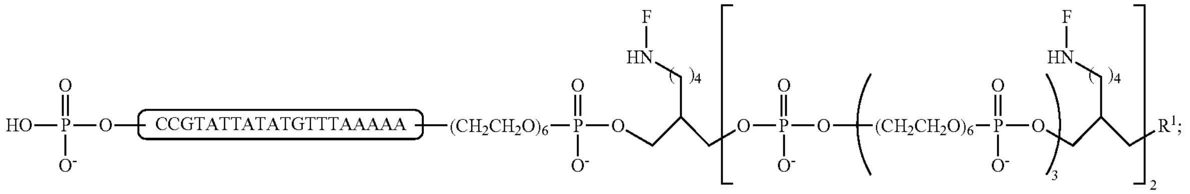
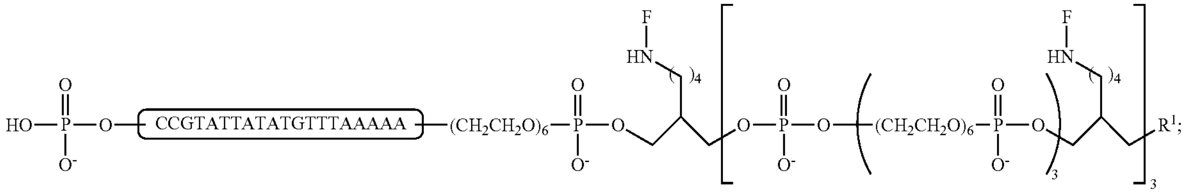
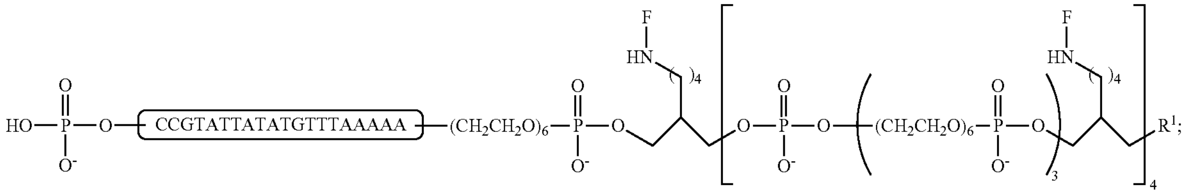
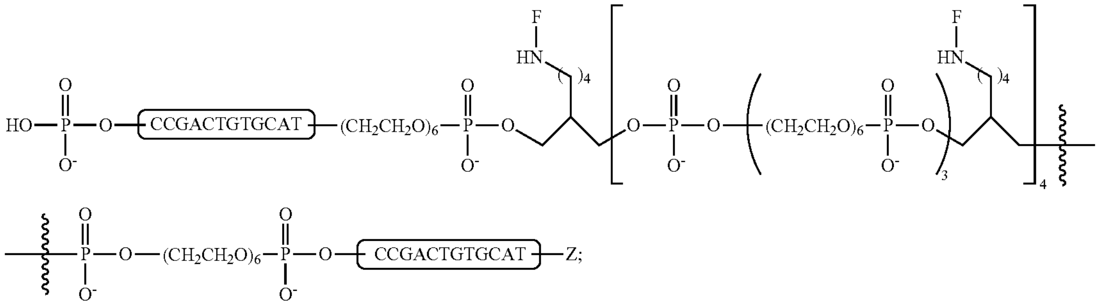
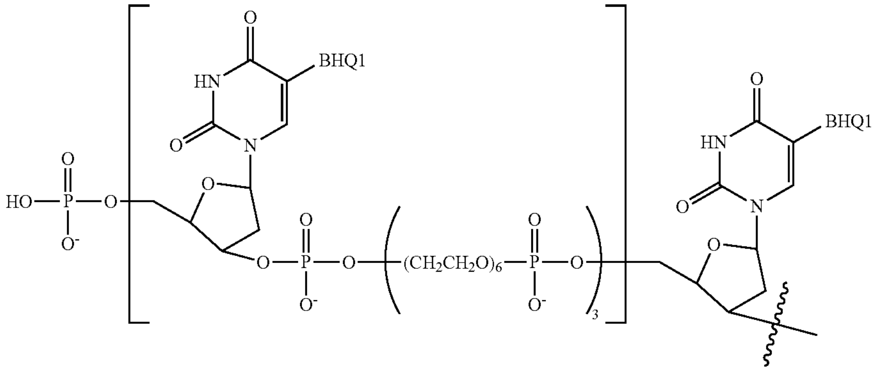

-continued
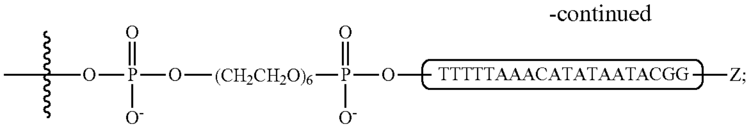
or
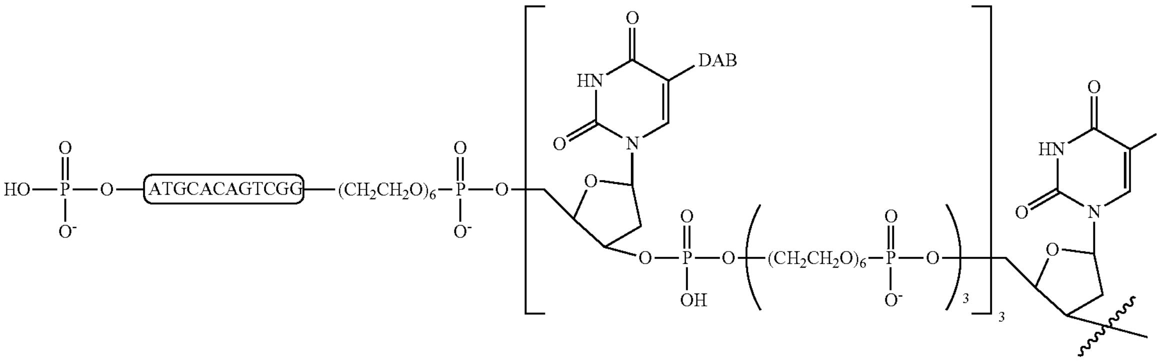
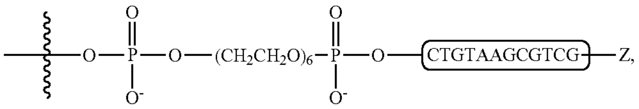
wherein:
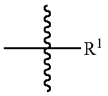
has the following structure
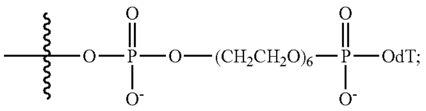
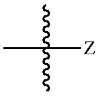
has the following structure
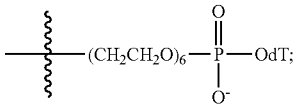
dT has the following structure
dT
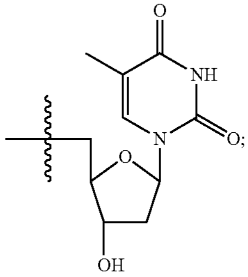
DAB has the following structure
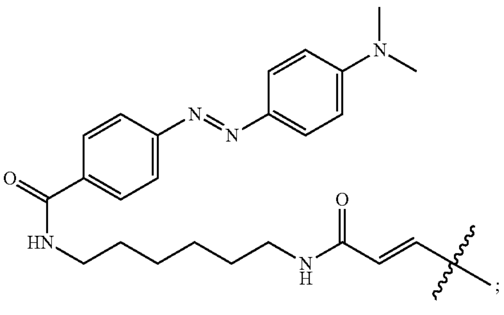 [SMILES: */C=C/C(=O)NCCCCCCNC(=O)c1ccc(/N=N/c2ccc(N(C)C)cc2)cc1]

F has the following structure
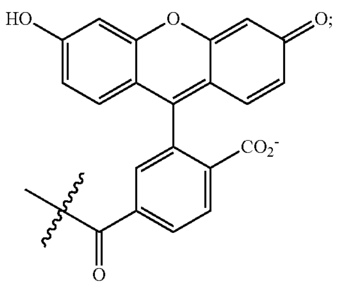
and
BHQ1 has the following structure
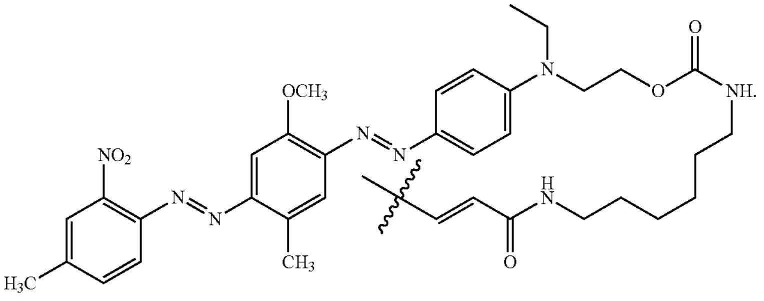 [SMILES: */C=C/C(=O)NCCCCCCNC(=O)OCCN(CC)c1ccc(/N=N/c2cc(C)c(/N=N/c3ccc(C)cc3[N+](=O)[O-])cc2OC)cc1]
* * * * *